(12) United States Patent
Papazoglou et al.

(10) Patent No.: US 9,551,710 B2
(45) Date of Patent: Jan. 24, 2017

(54) SIGNALING MOLECULE INVOLVED IN ULTRAVIOLET DAMAGE TO SKIN

(75) Inventors: Elisabeth S. Papazoglou, Yardley, PA (US); Zhenyu Huang, Voorhees, NJ (US); Constantinos Papathomas, legal representative, Yardley, PA (US)

(73) Assignee: Drexel University, Philadelphia, PA (US)

(*) Notice: Subject to any disclaimer, the term of this patent is extended or adjusted under 35 U.S.C. 154(b) by 160 days.

(21) Appl. No.: 13/575,559

(22) PCT Filed: Feb. 9, 2011
(Under 37 CFR 1.47)

(86) PCT No.: PCT/US2011/024212
§ 371 (c)(1),
(2), (4) Date: Nov. 15, 2012

(87) PCT Pub. No.: WO2011/100341
PCT Pub. Date: Aug. 18, 2011

(65) Prior Publication Data
US 2013/0072572 A1    Mar. 21, 2013

Related U.S. Application Data

(60) Provisional application No. 61/302,858, filed on Feb. 9, 2010.

(51) Int. Cl.
*G01N 33/53* (2006.01)
*G01N 33/573* (2006.01)
*C12Q 1/68* (2006.01)

(52) U.S. Cl.
CPC ............ *G01N 33/573* (2013.01); *C12Q 1/686* (2013.01); *G01N 2333/912* (2013.01); *G01N 2800/20* (2013.01); *G01N 2800/40* (2013.01)

(58) Field of Classification Search
CPC  G01N 33/53; G01N 33/573; G01N 2333/912; G01N 2800/20; G01N 2800/40; C12Q 1/686
See application file for complete search history.

(56) References Cited

U.S. PATENT DOCUMENTS

| | | | |
|---|---|---|---|
| 5,292,636 A * | 3/1994 | Kung et al. | 435/5 |
| 6,307,090 B1 | 10/2001 | Burke et al. | |
| 2002/0010217 A1 | 1/2002 | Uckun et al. | |
| 2006/0222671 A1 | 10/2006 | Weidner | |
| 2007/0219152 A1 | 9/2007 | Schreiber et al. | |
| 2009/0099197 A1 | 4/2009 | Lee | |
| 2011/0313143 A1 * | 12/2011 | Martin et al. | 536/23.1 |
| 2013/0310363 A1 * | 11/2013 | Mitchell et al. | 514/210.21 |

OTHER PUBLICATIONS

Benhamou et al., "Protein-tyrosine kinase p72syk in high affinity IgE receptor signaling. Identification as a component of pp72 and association with the receptor gamma chain after receptor aggregation." 1993, J. Biol. Chem. 268:23318-23324.
Chan et al., "Differential expression of ZAP-70 and Syk protein tyrosine kinases, and the role of this family of protein tyrosine kinases in TCR signaling." 1994, J. Immunol. 152:4758-4766.
Coopman et al., "The Syk tyrosine kinase suppresses malignant growth of human breast cancer cells." 2000, Nature 406:742-747.
de Gruijl & Forbes, "UV-induced skin cancer in a hairless mouse model." 1995, Bioessays 17:651-60.
de Gruijl, "Photocarcinogenesis: UVA vs UVB." 2000, Methods Enzymol. 319:359-366.
de Gruijl, "Skin cancer and solar UV radiation." 1999, Eur. J. Cancer 35:2003-2009.
Goodman et al., "Spleen tyrosine kinase (Syk) deficiency in childhood pro-B cell acute lymphoblastic leukemia." 2001, Oncogene 20:3969-3978.
Harrison et al., "Phosphorylation of human erythrocyte band 3 by endogenous p72syk."1994, J. Biol. Chem. 269:955-959.
Hoeller et al., "The non-receptor-associated tyrosine kinase Syk is a regulator of metastatic behavior in human melanoma cells." 2005, J. Invest. Dermatol. 124:1293-1299.
Inatome et al., "A critical role for Syk in endothelial cell proliferation and migration." 2001, Biochem. Biophys. Res. Commun. 286:195-199.
Kienle et al., "Evidence for distinct pathomechanisms in genetic subgroups of chronic lymphocytic leukemia revealed by quantitative expression analysis of cell cycle, activation, and apoptosis-associated genes." 2005, J. Clin. Oncol. 23:3780-3792.
Law et al., "Molecular cloning of human Syk. A B cell protein-tyrosine kinase associated with the surface immunoglobulin M-B cell receptor complex." 1994, J. Biol. Chem, 269:12310-12319.
Musch et al., "Volume expansion stimulates p72(syk) and p56(lyn) in skate erythrocytes." 1999, J. Biol. Chem. 274:7923-7928.
Ohta et al., "Protein-tyrosine kinase p72syk is activated by wheat germ agglutinin in platelets." 1992, Biochem. Biophys. Res. Commun. 185 :1128-1132.
Palmieri et al., "CD94/NKG2-A inhibitory complex blocks CD16-triggered Syk and extracellular regulated kinase activation, leading to cytotoxic function of human NK cells." 1999, J. Immunol. 162:7181-7188.
Papazoglou et al., "Noninvasive assessment of UV-induced skin damage: comparison of optical measurements to histology and MMP expression." 2010, Photochem Photobiol 86:138-45.

(Continued)

*Primary Examiner* — Gary W Counts
(74) *Attorney, Agent, or Firm* — Saul Ewing LLP; Kathryn Doyle; Brian R. Landry

(57) ABSTRACT

The present invention includes a method of detecting ultraviolet radiation (UVR)-induced skin damage in a mammal. The present invention also includes a method of identifying a mammal at risk of developing UVR-induced skin damage, photoaging, or photocarcinogenesis. The present invention further includes a method of inhibiting UVR-induced skin damage in a mammal at risk of developing UVR-induced skin damage. The present invention also includes a method of reducing the level of Syk kinase in the skin of a mammal. The present invention further includes methods of treating or diagnosing a disease associated with a change of Syk kinase expression in the skin in a mammal.

13 Claims, 31 Drawing Sheets

(56) References Cited

OTHER PUBLICATIONS

Qin et al., "Up-regulation of Syk activity during HL60 cell differentiation into granulocyte but not into monocyte/macrophage-lineage." 1997, Biochem. Biophys. Res. Commun. 236:697-701.
Schieven et al., "p72syk tyrosine kinase is activated by oxidizing conditions that induce lymphocyte tyrosine phosphorylation and Ca2+ signals." 1993, J. Biol. Chem. 268:16688-16692.
Taniguchi et al., "Molecular cloning of a porcine gene syk that encodes a 72-kDa protein-tyrosine kinase showing high susceptibility to proteolysis." 1991, J. Biol. Chem. 266:15790-15796.
Toyama et al., "Reduced expression of the Syk gene is correlated with poor prognosis in human breast cancer." 2003, Cancer Lett. 189:97-102.
Tsujimura et al., "Syk protein-tyrosine kinase is involved in neuron-like differentiation of embryonal carcinoma P19 cells." 2001, FEBS Lett. 489:129-133.
Ulanova et al., "Syk tyrosine kinase participates in betal-integrin signaling and inflammatory responses in airway epithelial cells." 2005, Am. J. Physiol. Lung Cell. Mol. Physiol. 288:L497-L507.
Wang et al., "G(s)alpha repression of adipogenesis via Syk." 1999, J. Biol. Chem. 274:32159-32166.
Wang et al., "Hypermethylation of Syk gene in promoter region associated with oncogenesis and metastasis of gastric carcinoma." 2004, World J. Gastroenterol. 10:1815-1818.
Woodhead et al., "Environmental factors in nonmelanoma and melanoma skin cancer." 1999, J. Epidemiol. 9:S102-S114.
Yamada et al., "Protein-tyrosine kinase Syk expressed in human nasal fibroblasts and its effect on RANTES production." 2001, J. Immunol. 166:538-543.
Yan et al., "Signaling by adhesion in human neutrophils: activation of the p72syk tyrosine kinase and formation of protein complexes containing p72syk and Src family kinases in neutrophils spreading over fibrinogen." 1997, J. Immunol. 158:1902-1910.
Yousefi et al., "Requirement of Lyn and Syk tyrosine kinases for the prevention of apoptosis by cytokines in human eosinophils," 1996, J. Exp. Med. 183:1407-1414.
Zhang et al., "Transfection of Syk protein tyrosine kinase reconstitutes high affinity IgE receptor-mediated degranulation in a Syk-negative variant of rat basophilic leukemia RBL-2H3 cells." 1996, J. Exp. Med. 184:71-79.
Zioncheck et al., "Generation of an active protein-tyrosine kinase from lymphocytes by proteolysis." 1988, J. Biol. Chem. 263:19195-19202.
Zioncheck et al., "Purification and characterization of a protein-tyrosine kinase from bovine thymus." 1986, J. Biol. Chem. 261:15637-15643.
Bhagwat, "Kinase inhibitors for the treatment of inflammatory and autoimmune disorders", Purinergic Signalling, 5:107-115 (2009).
Piskin et al., "Neutrophils infiltrating ultraviolet B-irradiated normal human skin display high IL-10 expression", Arch Dermatol. Res., 296:339-342 (2005).
Robert et al., "Blocking UV-Induced eIF2a Phosphorylation with Small Molecule Inhibitors of GCN2", Chem. Biol. Drug Des., 74:57-67 (2009).
Zhang et al., "Coactivation of Syk Kinase and MyD88 Adaptor Protein Pathways by Bacteria Promotes Regulatory Properties of Neutrophils", Immunity, 31:761-771 (2009).
Ichihashi, M., et al., "UV-induced skin damage", Toxicology 189, 21-39, 2003.
Qin, S., et al., "Distinctive Functions of Syk and Lyn in Mediating Osmotic Stress- and Ultraviolet C Irradiation-induced Apoptosis in Chicken B Cells", The Journal of Biological Chemistry, 272: 29, 17994-17999, Jul. 1997.

* cited by examiner

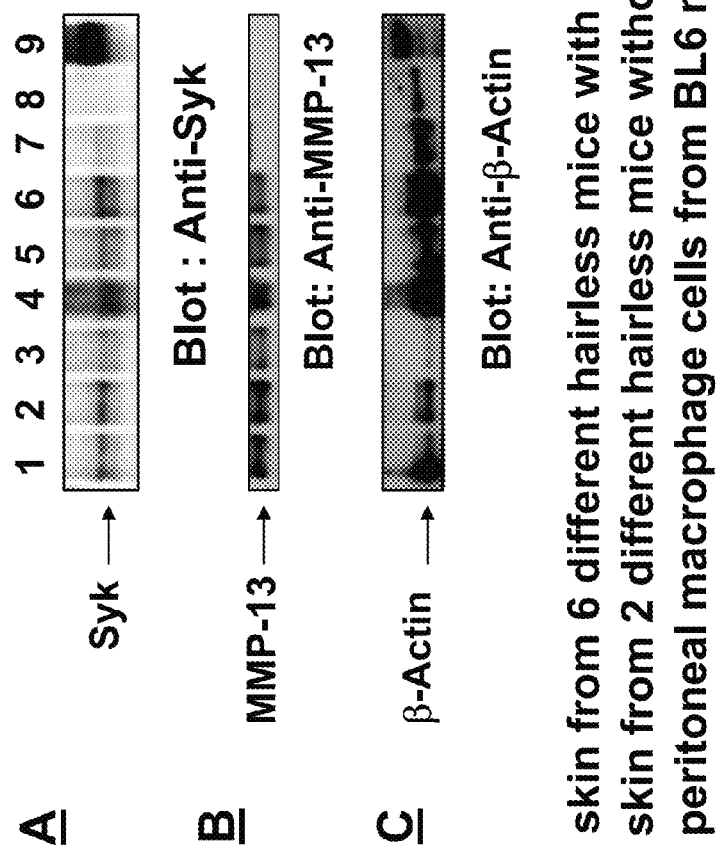

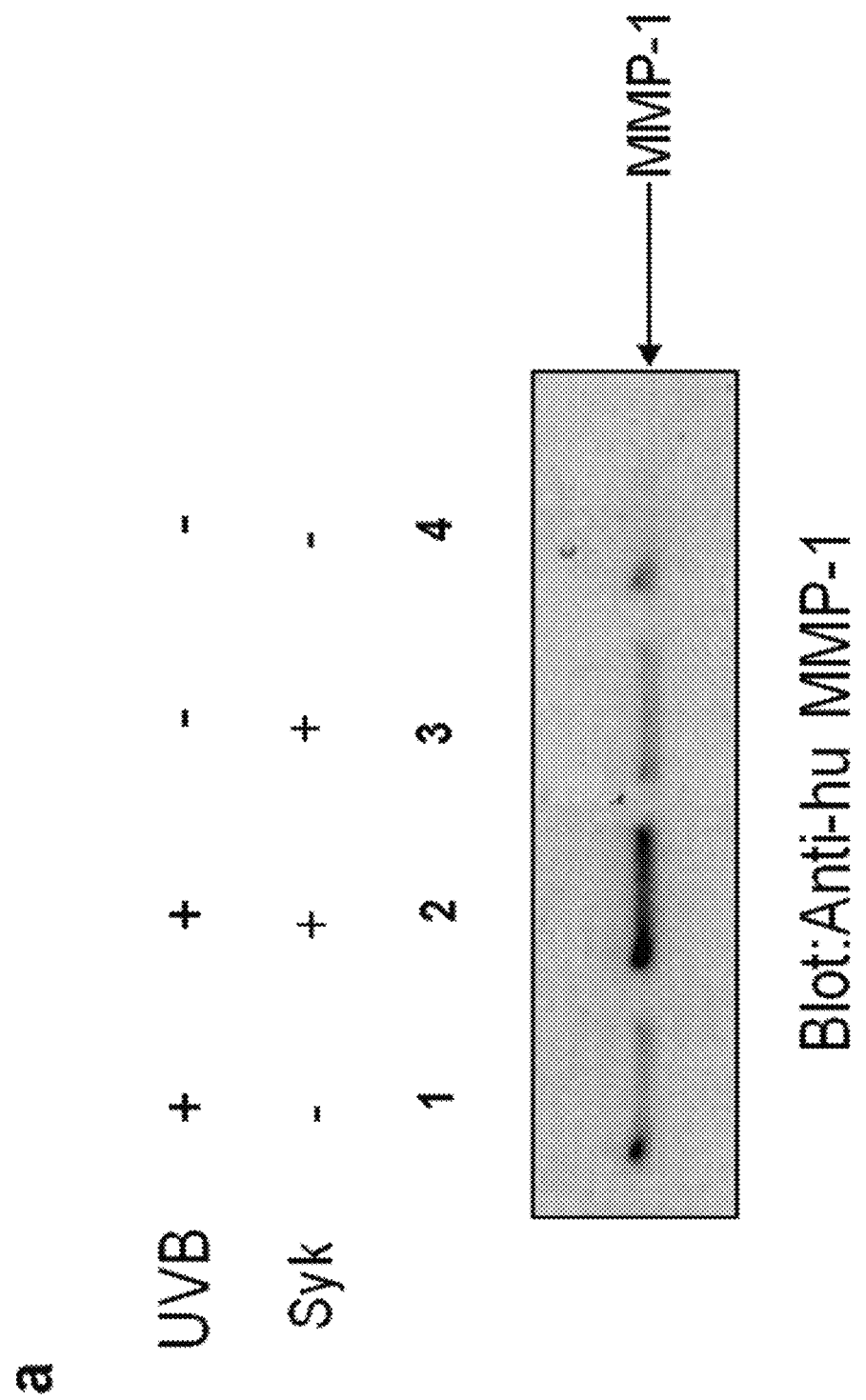

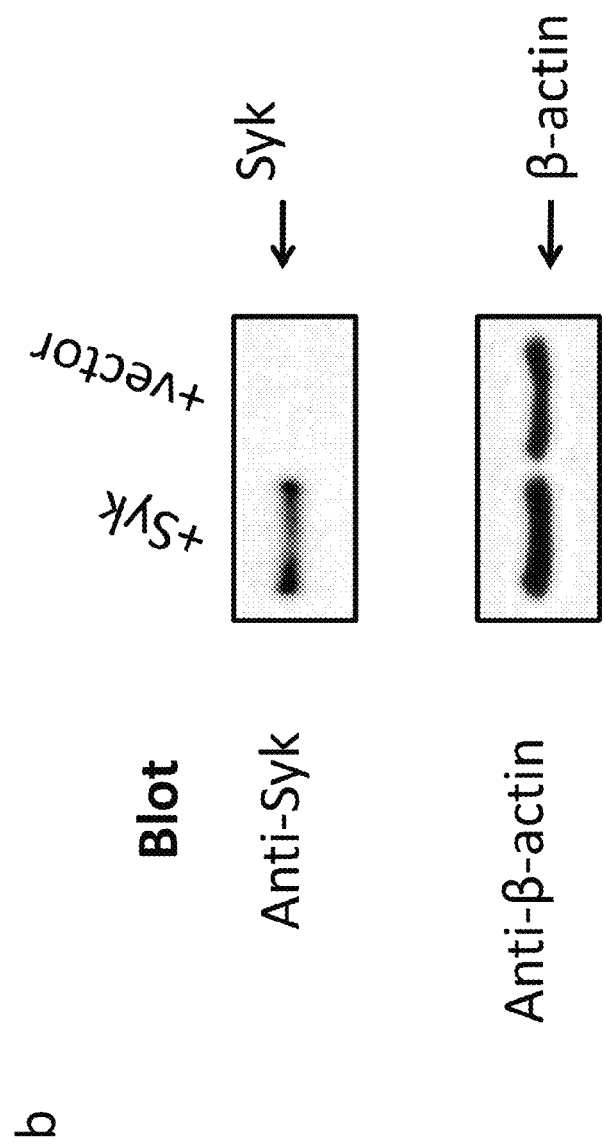

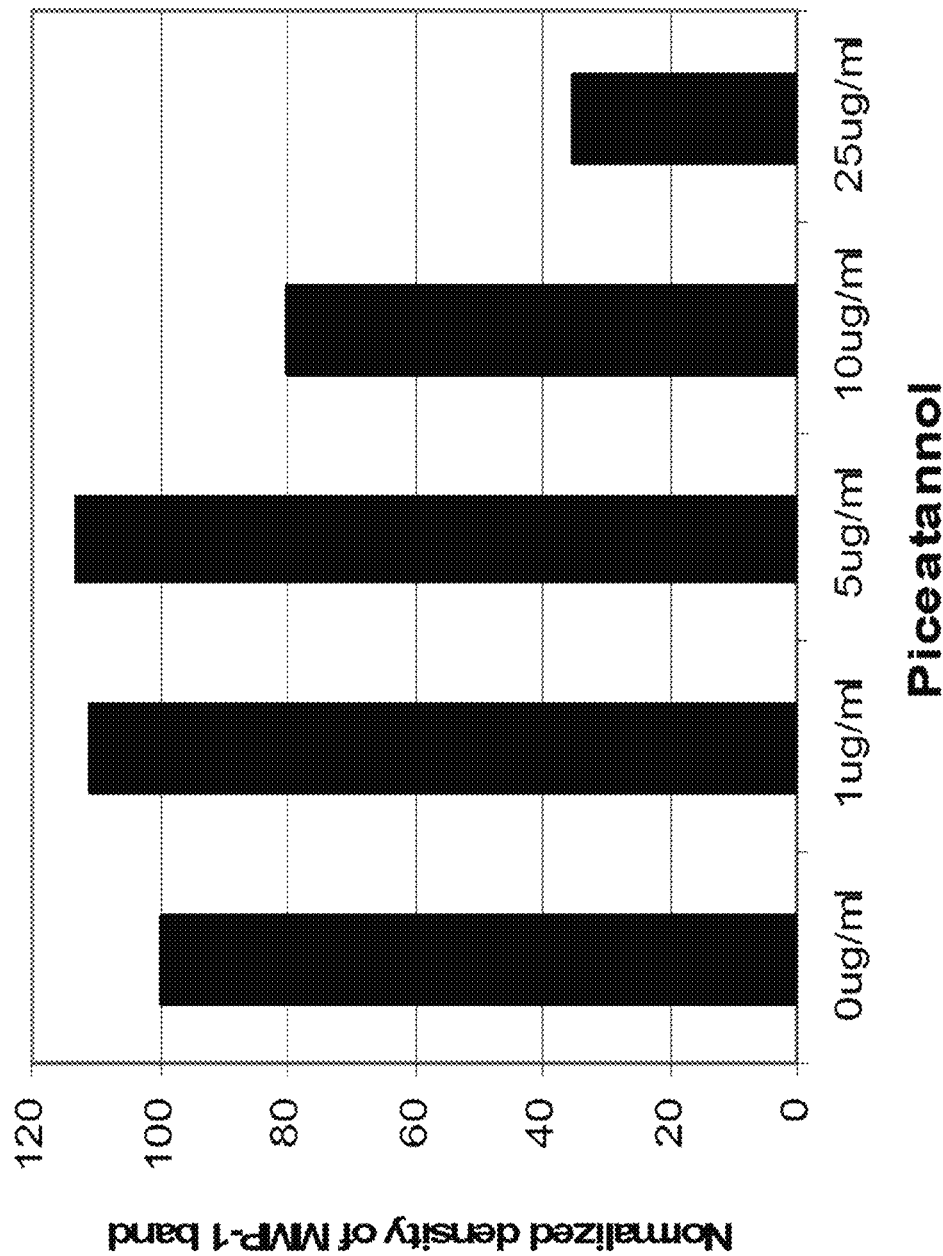

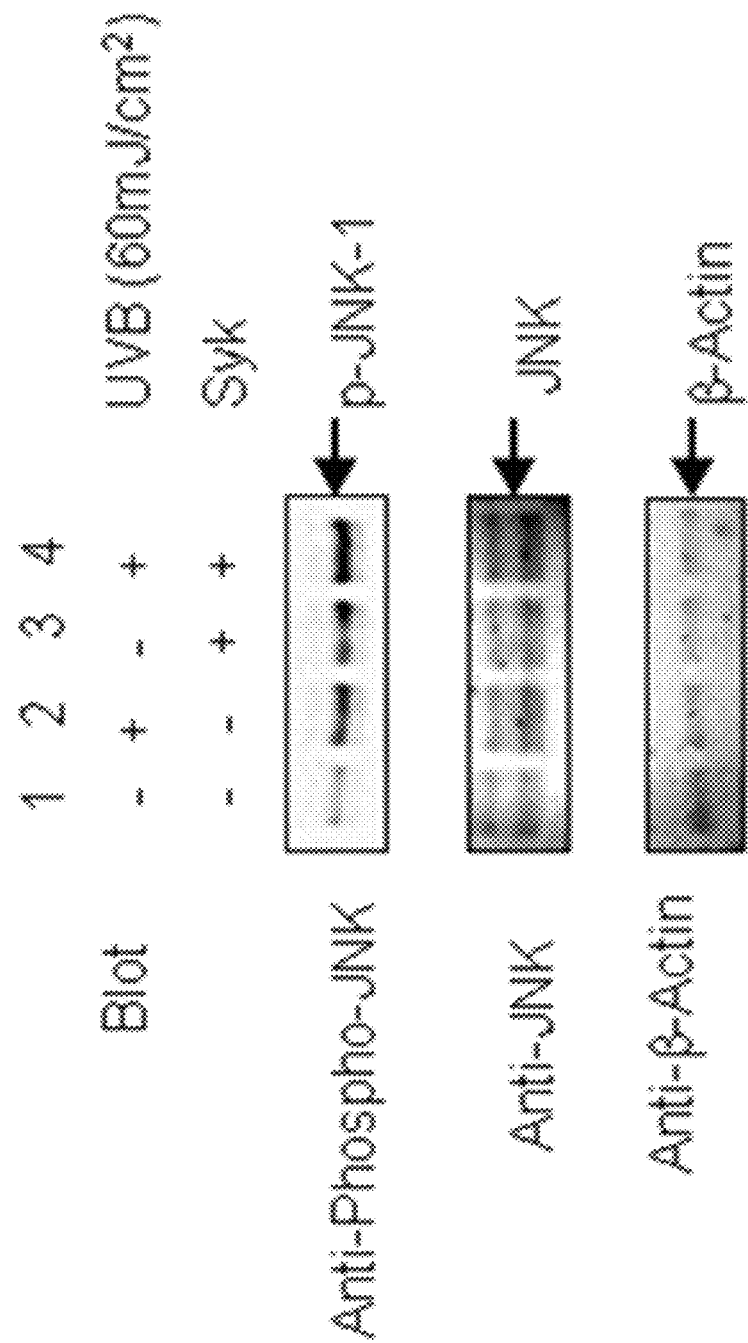

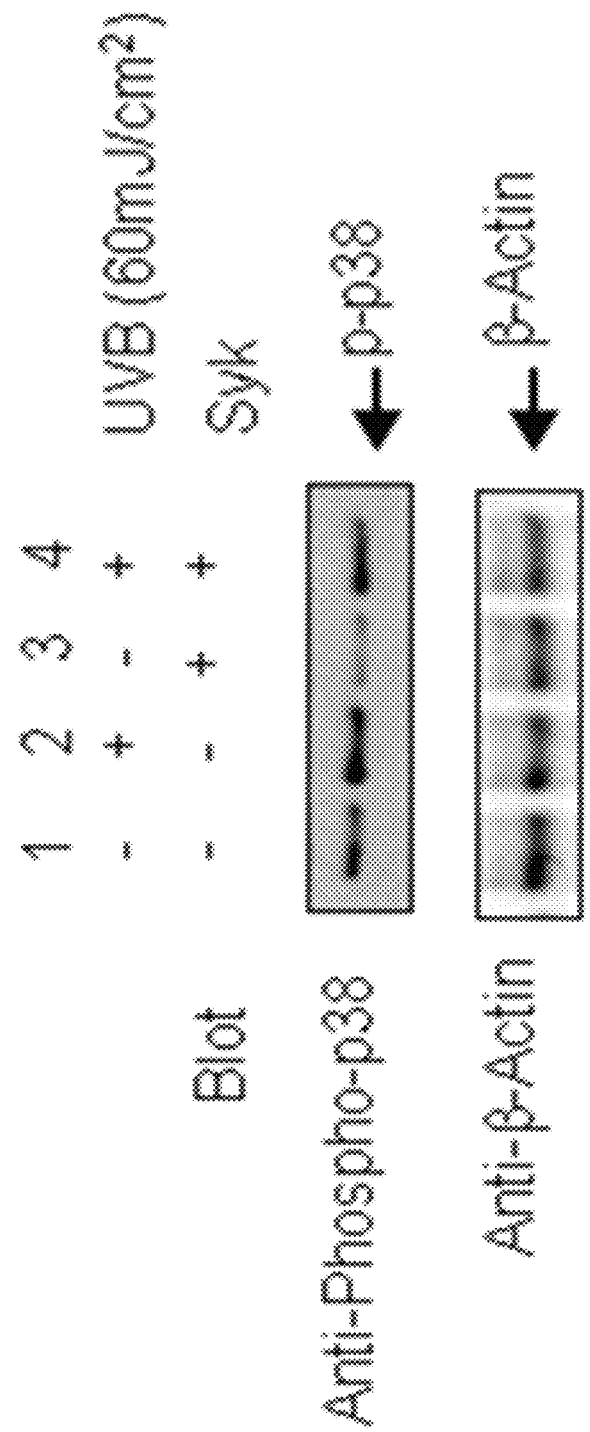

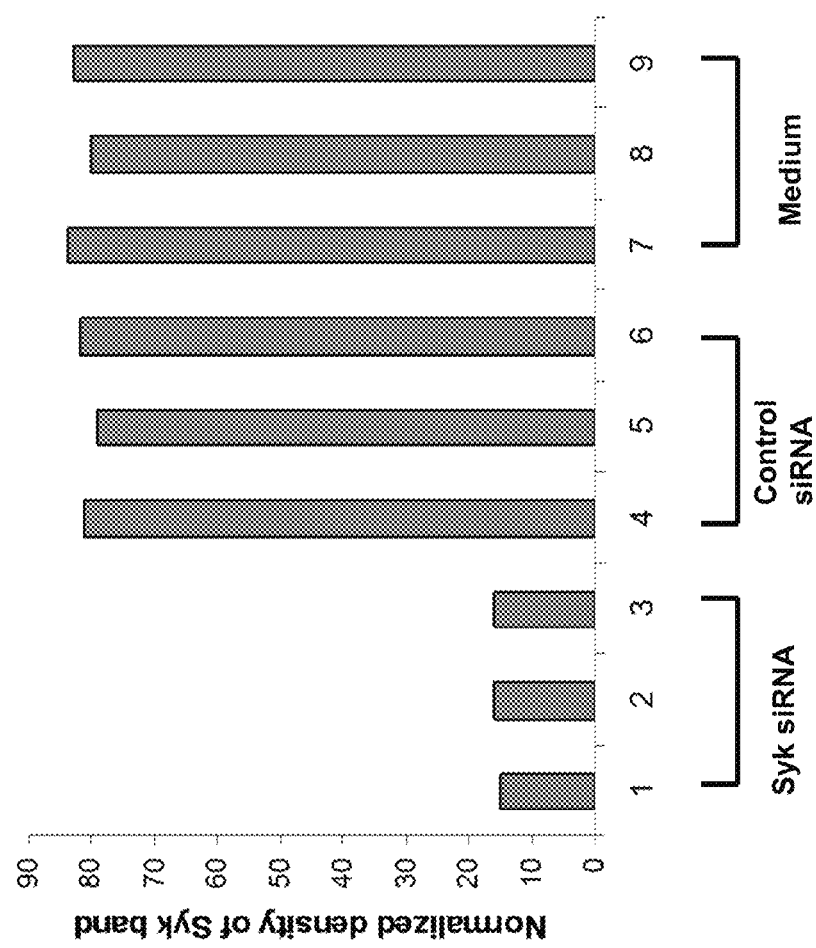

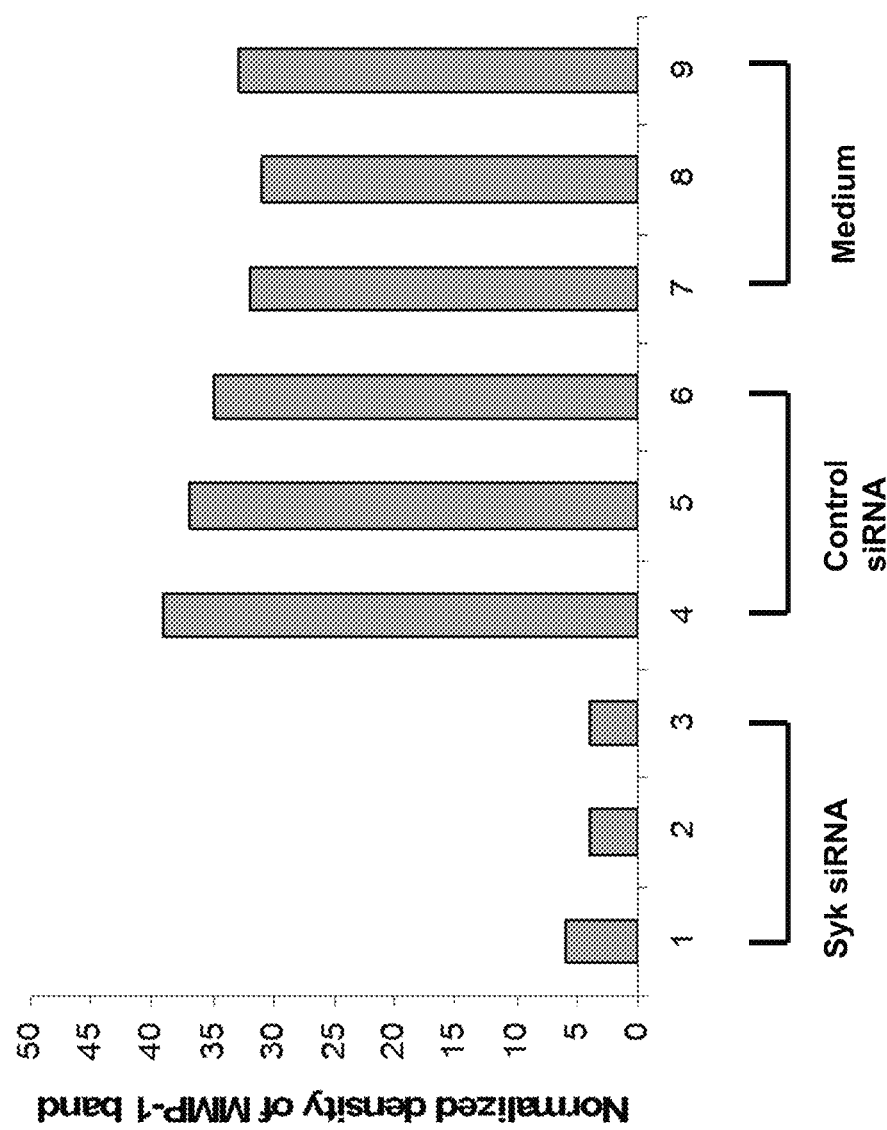

SEQUENCE LISTING

<160> NUMBER OF SEQ ID NOS: 10

<210> SEQ ID NO 1
<211> LENGTH: 2639
<212> TYPE: DNA
<213> ORGANISM: Homo sapiens

<400> SEQUENCE: 1

```
ctctaaaggc cgcgggccgg cggctgaggc caccccggcg gcggctggag agcgaggagg      60
agcgggtggc cccgcgctgc gcccgccctc gcctcacctg gcgcaggtgg acacctgccg     120
aggtgtgtgc cctccggccc ctgaagcatg gccagcagcg gcatggctga cagcgccaac     180
cacctgccct tcttttcgg caacatcacc cgggaggagg cagaagatta cctggtccag     240
gggggcatga gtgatgggct ttatttgctg cgccagagcc gcaactacct gggtggcttc     300
gccctgtccg tggcccacgg gaggaaggca caccactaca ccatcgagcg ggagctgaat     360
ggcacctacg ccatcgccgg tggcaggacc catgccagcc ccgccgacct ctgccactac     420
cactcccagg agtctgatgg cctggtctgc ctcctcaaga agcccttcaa ccggcccaa     480 ggggtgcagc ccaagactgg gcccttgag gatttgaagg aaaacctcat cagggaatat     540
gtgaagcaga catggaacct gcagggtcag gctctggagc aggccatcat cagtcagaag     600
cctcagctgg agaagctgat cgctaccaca gcccatgaaa aaatgccttg gttccatgga     660
aaaatctctc gggaagaatc tgagcaaatt gtcctgatag gatcaaagac aaatggaaag     720
ttcctgatcc gagccagaga caacaacggc tcctacgccc tgtgcctgct gcacgaaggg     780
aaggtgctgc actatcgcat cgacaaagac aagacaggga agctctccat ccccgaggga     840
aagaagttcg acacgctctg gcagctagtc gagcattatt cttataaagc agatggtttg     900
ttaagagttc ttactgtccc atgtcaaaaa atcggcacac agggaaatgt taattttgga     960
ggccgtccac aacttccagg ttcccatcct gcgacttggt cagcgggtgg aataatctca    1020
agaatcaaat catactcctt cccaaagcct ggccacagaa agtcctcccc tgcccaaggg    1080
aaccggcaag agagtactgt gtcattcaat ccgtatgagc cagaacttgc accctgggct    1140
gcagacaaag gcccccagag agaagcccta cccatggaca cagaggtgta cgagagcccc    1200
tacgcggacc ccgaggagat caggcccaag gaggtttacc tggaccgaaa gctgctgacg    1260
ctggaagaca aagaactggg ctctggtaat tttggaactg tgaaaaaggg ctactaccaa    1320
atgaaaaaag ttgtgaaaac cgtggctgtg aaaatactga aaaacgaggc caatgacccc    1380
gctcttaaag atgagttatt agcagaagca aatgtcatgc agcagctgga caacccgtac    1440
```

-continued

```
atcgtgcgga tgatcgggat atgcgaggcc gagtcctgga tgctggttat ggagatggca    1500
gaacttggtc ccctcaataa gtatttgcag cagaacagac atgtcaagga taagaacatc    1560
atagaactgg ttcatcaggt ttccatgggc atgaagtact tggaggagag caattttgtg    1620
cacagagatc tggctgcaag aaatgtgttg ctagttaccc aacattacgc caagatcagt    1680
gatttcggac tttccaaagc actgcgtgct gatgaaaact actacaaggc ccagacccat    1740
ggaaagtggc ctgtcaagtg gtacgctccg gaatgcatca actactacaa gttctccagc    1800
aaaagcgatg tctggagctt tggagtgttg atgtgggaag cattctccta tgggcagaag    1860
ccatatcgag ggatgaaagg aagtgaagtc accgctatgt tagagaaagg agagcggatg    1920
gggtgccctg cagggtgtcc aagagagatg tacgatctca tgaatctgtg ctggacatac    1980
gatgtggaaa acaggcccgg attcgcagca gtggaactgc ggctgcgcaa ttactactat    2040
gacgtggtga actaaccgct cccgcacctg tcggtggctg cctttgatca caggagcaat    2100
cacaggaaaa tgtatccaga ggaattgatt gtcagccacc tccctctgcc agtcgggaga    2160
gccaggcttg gatggaacat gcccacaact tgtcacccaa agcctgtccc aggactcacc    2220
ctccacaaag caaaggcagt cccggggaga aagacggatg caggatcca aggggctagc    2280 tggatttgtt tgttttcttg tctgtgtgat tttcatacag gttattttta cgatctgttt    2340
ccaaatccct ttcatgtctt tccacttctc tgggtcccgg ggtgcatttg ttactcatcg    2400
ggcccaggga cattgcagag tggcctagag cactctcacc ccaagcggcc ttttccaaat    2460
gcccaaggat gccttagcat gtgactcctg aaggaaggca aaggcagagg aatttggctg    2520
cttctacggc catgagactg atccctggcc actgaaaagc tttcctgaca ataaaaatgt    2580
tttgaggctt taaaagaaa aaaaaaaaa aaaaaaaaa aaaaaaactt tagagcaca    2639
```

<210> SEQ ID NO 2
<211> LENGTH: 635
<212> TYPE: PRT
<213> ORGANISM: Homo sapiens

<400> SEQUENCE: 2

```
Met Ala Ser Ser Gly Met Ala Asp Ser Ala Asn His Leu Pro Phe Phe
1               5                   10                  15

Phe Gly Asn Ile Thr Arg Glu Glu Ala Glu Asp Tyr Leu Val Gln Gly
            20                  25                  30

Gly Met Ser Asp Gly Leu Tyr Leu Leu Arg Gln Ser Arg Asn Tyr Leu
        35                  40                  45

Gly Gly Phe Ala Leu Ser Val Ala His Gly Arg Lys Ala His His Tyr
    50                  55                  60

Thr Ile Glu Arg Glu Leu Asn Gly Thr Tyr Ala Ile Ala Gly Gly Arg
65                  70                  75                  80

Thr His Ala Ser Pro Ala Asp Leu Cys His Tyr His Ser Gln Glu Ser
                85                  90                  95

Asp Gly Leu Val Cys Leu Leu Lys Lys Pro Phe Asn Arg Pro Gln Gly
            100                 105                 110

Val Gln Pro Lys Thr Gly Pro Phe Glu Asp Leu Lys Glu Asn Leu Ile
        115                 120                 125

Arg Glu Tyr Val Lys Gln Thr Trp Asn Leu Gln Gly Gln Ala Leu Glu
    130                 135                 140

Gln Ala Ile Ile Ser Gln Lys Pro Gln Leu Glu Lys Leu Ile Ala Thr
145                 150                 155                 160
```

```
Thr Ala His Glu Lys Met Pro Trp Phe His Gly Lys Ile Ser Arg Glu
                165                 170                 175
Glu Ser Glu Gln Ile Val Leu Ile Gly Ser Lys Thr Asn Gly Lys Phe
            180                 185                 190
Leu Ile Arg Ala Arg Asp Asn Asn Gly Ser Tyr Ala Leu Cys Leu Leu
        195                 200                 205
His Glu Gly Lys Val Leu His Tyr Arg Ile Asp Lys Asp Lys Thr Gly
    210                 215                 220
Lys Leu Ser Ile Pro Glu Gly Lys Lys Phe Asp Thr Leu Trp Gln Leu
225                 230                 235                 240
Val Glu His Tyr Ser Tyr Lys Ala Asp Gly Leu Leu Arg Val Leu Thr
                245                 250                 255
Val Pro Cys Gln Lys Ile Gly Thr Gln Gly Asn Val Asn Phe Gly Gly
            260                 265                 270
Arg Pro Gln Leu Pro Gly Ser His Pro Ala Thr Trp Ser Ala Gly Gly
        275                 280                 285
Ile Ile Ser Arg Ile Lys Ser Tyr Ser Phe Pro Lys Pro Gly His Arg
    290                 295                 300
Lys Ser Ser Pro Ala Gln Gly Asn Arg Gln Glu Ser Thr Val Ser Phe
305                 310                 315                 320
Asn Pro Tyr Glu Pro Glu Leu Ala Pro Trp Ala Ala Asp Lys Gly Pro
                325                 330                 335
Gln Arg Glu Ala Leu Pro Met Asp Thr Glu Val Tyr Glu Ser Pro Tyr
            340                 345                 350
Ala Asp Pro Glu Glu Ile Arg Pro Lys Glu Val Tyr Leu Asp Arg Lys
        355                 360                 365
Leu Leu Thr Leu Glu Asp Lys Glu Leu Gly Ser Gly Asn Phe Gly Thr
    370                 375                 380
Val Lys Lys Gly Tyr Tyr Gln Met Lys Lys Val Val Lys Thr Val Ala
385                 390                 395                 400
Val Lys Ile Leu Lys Asn Glu Ala Asn Asp Pro Ala Leu Lys Asp Glu
                405                 410                 415
Leu Leu Ala Glu Ala Asn Val Met Gln Gln Leu Asp Asn Pro Tyr Ile
            420                 425                 430
Val Arg Met Ile Gly Ile Cys Glu Ala Glu Ser Trp Met Leu Val Met
        435                 440                 445
Glu Met Ala Glu Leu Gly Pro Leu Asn Lys Tyr Leu Gln Gln Asn Arg
    450                 455                 460
His Val Lys Asp Lys Asn Ile Ile Glu Leu Val His Gln Val Ser Met
465                 470                 475                 480
Gly Met Lys Tyr Leu Glu Glu Ser Asn Phe Val His Arg Asp Leu Ala
                485                 490                 495
Ala Arg Asn Val Leu Leu Val Thr Gln His Tyr Ala Lys Ile Ser Asp
            500                 505                 510
Phe Gly Leu Ser Lys Ala Leu Arg Ala Asp Glu Asn Tyr Tyr Lys Ala
        515                 520                 525
Gln Thr His Gly Lys Trp Pro Val Lys Trp Tyr Ala Pro Glu Cys Ile
    530                 535                 540
Asn Tyr Tyr Lys Phe Ser Ser Lys Ser Asp Val Trp Ser Phe Gly Val
545                 550                 555                 560
Leu Met Trp Glu Ala Phe Ser Tyr Gly Gln Lys Pro Tyr Arg Gly Met
                565                 570                 575
Lys Gly Ser Glu Val Thr Ala Met Leu Glu Lys Gly Glu Arg Met Gly
```

```
                580             585             590
Cys Pro Ala Gly Cys Pro Arg Glu Met Tyr Asp Leu Met Asn Leu Cys
            595                 600             605

Trp Thr Tyr Asp Val Glu Asn Arg Pro Gly Phe Ala Ala Val Glu Leu
            610                 615             620

Arg Leu Arg Asn Tyr Tyr Asp Val Val Asn
625                 630             635
```

<210> SEQ ID NO 3
<211> LENGTH: 12
<212> TYPE: PRT
<213> ORGANISM: Artificial sequence
<220> FEATURE:
<223> OTHER INFORMATION: Chemically synthesized

<400> SEQUENCE: 3

```
Cys Met His Ile Glu Ser Leu Asp Ser Tyr Thr Cys
1               5                   10
```

<210> SEQ ID NO 4
<211> LENGTH: 12
<212> TYPE: PRT
<213> ORGANISM: Artificial sequence
<220> FEATURE:
<223> OTHER INFORMATION: Chemically synthesized

<400> SEQUENCE: 4

```
Cys Met Tyr Ile Glu Ala Leu Asp Lys Tyr Ala Cys
1               5                   10
```

<210> SEQ ID NO 5
<211> LENGTH: 8
<212> TYPE: PRT
<213> ORGANISM: Artificial sequence
<220> FEATURE:
<223> OTHER INFORMATION: Chemically synthesized

<400> SEQUENCE: 5

```
Gly Asn Ala Ala Ala Ala Arg Arg
1               5
```

<210> SEQ ID NO 6
<211> LENGTH: 10
<212> TYPE: PRT
<213> ORGANISM: Artificial sequence
<220> FEATURE:
<223> OTHER INFORMATION: Chemically synthesized

<400> SEQUENCE: 6

```
Cys Asp Pro Gly Tyr Ile Gly Ser Arg Cys
1               5                   10
```

<210> SEQ ID NO 7
<211> LENGTH: 20
<212> TYPE: DNA
<213> ORGANISM: Artificial sequence
<220> FEATURE:
<223> OTHER INFORMATION: Chemically synthesized

<400> SEQUENCE: 7
ttttggaggc cgtccacaac                                          20

<210> SEQ ID NO 8
<211> LENGTH: 24
<212> TYPE: DNA

```
<213> ORGANISM: Artificial sequence
<220> FEATURE:
<223> OTHER INFORMATION: Chemically synthesized

<400> SEQUENCE: 8
tgcatgacat tgcttctgc taat                                              24

<210> SEQ ID NO 9
<211> LENGTH: 16
<212> TYPE: DNA
<213> ORGANISM: Artificial sequence
<220> FEATURE:
<223> OTHER INFORMATION: Chemically synthesized

<400> SEQUENCE: 9
gctccggcat gtgcaa                                                      16

<210> SEQ ID NO 10
<211> LENGTH: 19
<212> TYPE: DNA
<213> ORGANISM: Artificial sequence
<220> FEATURE:
<223> OTHER INFORMATION: Chemically synthesized

<400> SEQUENCE: 10
aggatcttca tgaggtagt                                                   19
```

SIGNALING MOLECULE INVOLVED IN ULTRAVIOLET DAMAGE TO SKIN

CROSS-REFERENCE TO RELATED APPLICATION

This application is the U.S. national phase application filed under 35 U.S.C. §371 claiming benefit to International Application No. PCT/US2011/24212, filed on Feb. 9, 2011, which is entitled to priority under 35 U.S.C. §119(e) to U.S. Provisional Patent Application Ser. No. 61/302,858, filed Feb. 9, 2010, each of which is hereby incorporated herein by reference in its entirety.

STATEMENT REGARDING FEDERALLY SPONSORED RESEARCH OR DEVELOPMENT

This invention was made with government support under grant number AR050397 awarded by the National Institutes of Health. The U.S. Government has certain rights in this invention.

BACKGROUND OF THE INVENTION

Spleen tyrosine kinase (Syk) was originally cloned from porcine spleen (Taniguchi et al., 1991, J. Biol. Chem. 266:15790-15796). It was initially purified as a 40 kD protein-tyrosine kinase (PTK), but it was later found to be a major proteolytic product of a larger 72 kD mature protein (Taniguchi et al., 1991, J. Biol. Chem. 266:15790-15796; Law et al., 1994, J. Biol. Chem. 269:12310-12319; Zioncheck et al., 1986, J. Biol. Chem. 261:15637-15643; Zioncheck et al., 1988, J. Biol. Chem. 263:19195-19202) The human Syk locus has been mapped to chromosome 9 at band q22 (Law et al., 1994, J. Biol. Chem. 269:12310-12319).

Syk was long thought to be a hematopoietic cell-specific signaling molecule (Yan et al., 1997, J. Immunol. 158:1902-1910; Qin et al., 1997, Biochem. Biophys. Res. Commun. 236:697-701; Palmieri et al., 1999, J. Immunol. 162:7181-7188; Ohta et al., 1992, Biochem. Biophys. Res. Commun 185:1128-1132; Schieven et al., 1993, J. Biol. Chem. 268: 16688-16692; Chan et al., 1994, J. Immunol. 152:4758-4766; Yousefi et al., 1996, J. Exp. Med. 183:1407-1414; Benhamou et al., 1993, J. Biol. Chem. 268:23318-23324; Musch et al., 1999, J. Biol. Chem. 274:7923-7928; Harrison et al., 1994, J. Biol. Chem. 269:955-959; Zhang et al., 1996, J. Exp. Med. 184:71-79). Recent studies have demonstrated that Syk is expressed by many non-hematopoietic cells including normal and tumorigenic mammary epithelial cells (Coopman et al., 2000, Nature 406:742-747), airway epithelial cells, vascular endothelial cells, melanocytes, neuron-like cells (Ulanova et al., 2005, Am. J. Physiol. Lung Cell. Mol. Physiol. 288:L497-L507; Inatome et al., 2001, Biochem. Biophys. Res. Commun. 286:195-199; Tsujimura et al., 2001, Fed. Eur. Biochem. Soc. Lett. 489:129-133; Hoeller et al., 2005, J. Invest. Dermatol. 124:1293-1299), the mouse embryonic fibroblast cell line 3T3-L1 (where it plays a role in the differentiation of 3T3-L1 to adipocytes and adipogenesis (Wang et al., 1999, J. Biol. Chem. 274: 32159-32166), and human nasal fibroblasts (Yamada et al., 2001, J. Immunol. 166:538-543).

Some data suggest that Syk could be a potential marker for tumor formation and progression. A comparison of Syk mRNA levels between primary breast cancer tissue and adjacent non-cancerous breast tissue using real-time quantitative PCR demonstrated that patients with reduced Syk expression have increased risk for distant metastasis (Toyama et al., 2003, Cancer Lett. 189:97-102). Wang et al. (2004, World J. Gastroenterol. 10:1815-1818) demonstrated that Syk expression was lower in gastric cancer patients with lymph node metastasis than in patients without lymph node metastasis. Goodman et al. (2001, Oncogene 20:3969-3978) demonstrated that reduced Syk expression and activity is observed in the leukemic cells from acute lymphoblastic leukemia (ALL) patients. The Syk mRNA sequence in pro-B leukemia cells of ALL patients exhibited deletions or insertions that result in abnormal Syk proteins with a missing or truncated catalytic kinase domain (Goodman et al., 2001, Oncogene 20:3969-3978). Syk is also overexpressed in anaplastie large cell lymphoma (ALCL), a very aggressive large T- or null-cell lymphoma that usually expresses anaplastie lymphoma kinase (ALK) (Kienle et al., 2005, J. Clin. Oncol. 23:3780-3792).

Ultraviolet radiation (UVR) from sunlight is a major etiologic factor in human skin photoaging and photocarcinogenesis. The ozone layer blocks UVC (180-280 nm). It is generally thought that UVB (280-320 nm) and UVA (320-400 nm) are responsible for sunlight-induced skin photodiseases (de Gruijl, 1999, Eur. J. Cancer 35:2003-2009; de Gruijl, 2000, Methods Enzymol. 319:359-366). UVA comprises approximately 90% or more of the total solar UVR, while UVB comprises the remaining 1-10% of the total UVR (de Gruijl, 1999, Eur. J. Cancer 35:2003-2009; Woodhead et al., 1999, J. Epidemiol. 9:S102-S114).

The signal cascade for UVR effects in skin begin with the stimulation of cell surface receptors, like epidermal growth factor receptor (EGFR). Following the activation of cell surface receptors by UVR, subsequent activation of mitogen-activated protein kinases (MAPKs) occurs by dual phosphorylation on threonine and tyrosine at Threonine-X-Tyrosine motifs within the activation loop of MAPKs. MAPKs are a family of proteins that include the extracellular signal regulated kinases (ERKs), p38 kinase, and c-Jun $NH_2$-terminal kinase (JNKs) (Yousefi et al., 1996, J. Exp. Med. 183:1407-1414). ERK has two isoforms (1/2); p38 kinase has four isoforms ($\alpha/\beta/\delta/\gamma$); and JNKs has three isoforms (1/2/3) (Pearson et al., 2001, Endocr. Rev. 22:153-183; Tibbles et al., 1999, Cell. Mol. Life. Sci. 55:1230-1254).

One or more MAPK kinases (MAPKKs) catalyze this phosphorylation. MAPKKs themselves are activated by MAPKK kinases (MAPKKKs). Besides the cell surface receptor induced MAPKKK-MAPKK-MAPK pathway, MAPK can also be activated through the Ras family of G proteins. After Ras is activated, it will initially induce cell proliferation, targeting MEK1/2 MAPKK activation. Activated MAPKKs further activate ERK1/2 that can induce the AP-1 transcription factor that is related to cell proliferation. Ras-MEK-ERK also activates p38 and increases the expression of p53 and p16, which have anti-proliferation function (Iordanov et al., 2002, Mol. Cell. Biol. 22:5380-5394; Lin et al., 1998, Genes Dev. 12:3008-3019).

Normally, MAPKs mediate several cellular and organismal functions including proliferation, growth, differentiation, development, and apoptosis. MAPKs also play a significant role in mediating the UV induced biological effects, making the MAPK signaling cascade the key signal pathway triggered by UV (Bode et al., 2003, Sci. SETK 167:RE2; Kyriakis et al., 2001, Physiol. Rev. 81:807-869). Under stress conditions like UV stimulation, MAPK signaling is important for protecting the epidermis against UVR induced skin damage and carcinogenesis by activating cell cycle arrest, apoptosis, and inflammation in damaged tissues (Xia et al., 1995, Science 270:1326-1331; Chang et al., 2001, Nature 410:37-40).

Matrix metalloproteinases (MMPs) are thought to play an important role in the pathology of photoaging (Fisher et al., 1996, Nature 379:335-339; Scharffetter et al., 1991, Arch. Dermatol. Res. 283:506-511). Both UVA and UVB can induce MMP overexpression; however, several differences have been found between UVA and UVB induced signaling.

UVB is mostly absorbed by keratinocytes in the epidermis. After the transcription factors activator protein-1 (AP-1) and nuclear factor κB (NF-κB) are induced, they can further activate the gene expression of MMPs. In contrast to the UVA mediated signaling pathway, UVB may activate the MAPKs by stimulating the EGFR and/or PKC (a typical protein kinase C). UVB can also activate the PI3K (phosphatidylinositol 3-kinase) pathway, which can further activate many downstream molecules such as Akt (also called protein kinase B). In general terms, JNK and p38 MAPKs are activated by stress stimulations such as UVR while ERKs are activated by mitogenic stimuli (Xia et al., 1995, Science 270:1326-1331; Chang et al., 2001, Nature 410:37-40). However, there is significant cross talk among these three MAPKs p38 and ERKs).

In contrast, the longer wavelength UVA penetrates deeper into the skin and can affect both epidermal keratinocytes and dermal fibroblasts. UVA affects expression of MMPs mainly through the generation of reactive oxygen species (ROS) (Fisher et al., 1997, N. Engl. J. Med. 337; 1419-1428; Fisher et al., 1998, J. Clin. Invest. 101:1432-1440; Sato et al., 1993, Oncogene 8:395-405). It was first thought that UVA might phosphorylate EGFR, thus activating several downstream effector molecules, leading to the phosphorylation of $p70^{S6K}$ and $p90^{RSK}$. These two phosphorylated proteins could further phosphorylate the 40S ribosomal protein S6. UVA might also activate the JNKs, ATM (ataxia telangiectasia imitated) and SMase (sphingomyelinase) which lead to apoptosis (Zhang et al., 2001, DNA Cell Biol. 20; 769-779; Zhang et al., 2001, J. Biol. Chem. 276:14572-14580; Hamilton et al., 1998, J. Biol. Chem. 273:28155-28162).

UVB was thought to be the highly mutagenic agent responsible for skin cancer development, because DNA is a chromophore for UVB radiation (but not for UVA) (Rosenstein et al., 1987, Photochem. Photobiol. 45:775-780). However, the UVA and UVB generated free radicals such as OH radical, one-electron oxidation oxidants and single oxygen can still damage DNA and cause base pair loss, single strand breaks, and protein-DNA crosslinking (Ichibashi et al., 2003, Toxicology 189; 21-39; Peus et al., 1998, J. Invest. Dermatol. 110:966-971; Darr et al., 1994, J. Invest. Dermatol. 102:671-675).

In the skin, many studies have demonstrated that MAPKs play an important role in regulating several key oncogenes and tumor suppressors that are relevant to UV induced cancers including p53, p16, APC/β-catenin, and Ha-Ras. JNK and p38 are thought to block cell proliferation or promote cell apoptosis via modulation of p53, which can prevent the tumor growing. Apoptosis would be impaired in the absence of JNK and p38 (Wang et al., 2002, Mol. Cell. Biol. 22:3389-3403; She et al., 2000, Oncogene 21:1580-1589; Hildesheim et al., 2004, J. Invest. Dermatol. 122:497-502). For instance, it was found that p38 inhibitor SB202190 blocked the UV induced apoptosis in mouse skin. p38 could phosphorylate Ser33 and ser37 of p53, while the Ser15 of p53 could be phosphorylated by p38 and ERK, and JNK phosphorylated Ser20 of p53 (She et al., 2000, Oncogene 21:1580-1589; Hildesheim et al., 2004, J. Invest. Dermatol. 122; 497-502; She et al., 2000, J. Biol. Chem. 275:20444-20449; Shieh et al., 2000, Genes Dev. 14:289-300).

MAPKs involved apoptosis is an essential and effective way to protect and repair UV induced skin damage. MAPKs are not only involved in apoptosis but also required by the UV induced inflammation. Keratinocytes are the major cells that release cytokines in the epidermis. After UV radiation, they secrete many cytokines, such as granulocyte colony-stimulating factor (G-CSF), IL-3, IL-8, macrophage-CSF, transforming growth factor α/β (TGF α/β), platelet-derived growth factor (PDGF), GM-CSF, interferon gamma (INFγ). These cytokines can further attract Langerhan's cells and activate neutrophils, macrophages and fibroblasts. MAPKs have been shown to regulate expression of all these cytokines (Ansel et al., 1990, J. Invest. Dermatol. 94:101 S-107S; Luger et al., 1990, J. Invest, Dermatol. 95:100 S-104S; Beyaert et al., 1996, EMBO J. 15:1914-1923; Lee et al., 1996, J. Leukoc. Biol. 59:152-157; Wery-Zennaro et al., 2000, Oncogene 19:1596-1604).

There remains a need in the art to identify novel markers of UVR damage in skin as well as new therapeutic targets for the treatment and remediation of UVR damage. The present invention fills this need.

BRIEF SUMMARY OF THE INVENTION

The invention includes a method of detecting ultraviolet radiation (UVR)-induced skin damage in a mammal. The method comprises the step of obtaining a skin sample from the mammal. The method further comprises the step of measuring the level of Syk kinase in the skin sample, wherein, when the level of the Syk kinase in the sample is elevated compared to the level of Syk kinase in a control sample, the mammal is afflicted with UVR-induced skin damage.

In one embodiment, the mammal is selected from the group consisting of a mouse, rat, non-human primate, and human. In another embodiment, the mammal is a human. In yet another embodiment, the measuring of the Syk kinase comprises an immunoassay for assessing the level of the Syk kinase in the sample. In yet another embodiment, the immunoassay is selected from the group consisting of Western blot, ELISA, immunoprecipitation, immunohistochemistry, immunofluorescence, radioimmunoassay, dot blotting, and FACS. In yet another embodiment, the measuring of the Syk kinase comprises a nucleic acid assay for assessing the level of a nucleic acid encoding the Syk kinase in the sample. In yet another embodiment, the nucleic acid assay is selected from the group consisting of a Northern blot, Southern blot, in situ hybridization, PCR assay, RT-PCR assay, probe array, gene chip, and microarray. In yet another embodiment, the skin sample comprises skin tissue.

The invention also includes a method of identifying a mammal at risk of developing UVR-induced skin damage, photoaging, or photocarcinogenesis. The method comprises the step of obtaining a skin sample from the mammal. The method further comprises the step of measuring the level of Syk kinase in the skin sample, wherein, when the level of the Syk kinase in the sample is elevated compared to the level of Syk kinase in a control sample, the mammal is at risk of developing UVR-induced skin damage, photoaging, or photocarcinogenesis.

In one embodiment, the mammal is selected from the group consisting of a mouse, rat, non-human primate, and human. In another embodiment, the mammal is a human. In yet another embodiment, the measuring of the Syk kinase comprises an immunoassay for assessing the level of the Syk kinase in the sample. In yet another embodiment, the immunoassay is selected from the group consisting of Western blot, ELISA, immunoprecipitation, immunohistochemistry, immunofluorescence, radioimmunoassay, dot blotting, and FACS. In yet another embodiment, the measuring of the Syk kinase comprises a nucleic acid assay for assessing the level of a nucleic acid encoding the Syk kinase in the sample. In yet another embodiment, the nucleic acid assay is selected from the group consisting of a Northern blot, Southern blot, in situ hybridization, PCR assay, RT-PCR assay, probe array, gene chip, and microarray. In yet another embodiment, the skin sample comprises skin tissue.

The invention further includes a method of inhibiting UVR-induced skin damage in a mammal at risk of developing UVR-induced skin damage. The method comprises the step of topically administering a pharmaceutical composition comprising an effective amount of a Syk kinase inhibitor to the mammal, wherein the Syk kinase inhibitor inhibits the UVR-induced skin damage in the mammal.

In one embodiment, the mammal is selected from the group consisting of a mouse, rat, non-human primate, and human. In another embodiment, the mammal is a human. In yet another embodiment, the Syk kinase inhibitor comprises an inhibitor selected from the group consisting of antibody, intrabody, siRNA, ribozyme, antisense, aptamer, peptidomimetic, small molecule, vitamin, and any combination thereof. In yet another embodiment, the Syk kinase inhibitor is piceatannol or a salt thereof. In yet another embodiment, the vitamin is selected from the group consisting of vitamin A, Vitamin C, and vitamin E.

The invention also includes a method of reducing the level of Syk kinase in the skin of a mammal. The method comprises the step of contacting the skin of the mammal with a dermally-acting composition, wherein the composition comprises a delivery vehicle and an effective amount of a Syk kinase inhibitor, thereby reducing the level of the Syk kinase in the skin of the mammal.

In one embodiment, the delivery vehicle comprises a lipid component. In another embodiment, the delivery vehicle comprises a liposome. In yet another embodiment, the Syk kinase inhibitor comprises an inhibitor selected from the group consisting of antibody, intrabody, siRNA, ribozyme, antisense, aptamer, peptidomimetic, small molecule, and any combination thereof. In yet another embodiment, the Syk kinase inhibitor is piceatannol or a salt thereof.

The invention further includes a method of treating a disease or disorder associated with a change of Syk kinase expression in the skin in a mammal. The method comprises the step of topically administering to the skin of the mammal a pharmaceutical composition comprising a therapeutically effective amount of at least one Syk kinase inhibitor, thereby reducing the Syk kinase expression in the skin of the mammal and treating the disease or disorder.

In one embodiment, the Syk kinase inhibitor comprises an inhibitor selected from the group consisting of antibody, intrabody, siRNA, ribozyme, antisense, aptamer, peptidomimetic, small molecule, and any combination thereof. In another embodiment, the Syk kinase inhibitor is piceatannol or a salt thereof. In yet another embodiment, the mammal is a human. In yet another embodiment, the disease or disorder is selected from the group consisting of UVR-induced skin damage, UVR-induced photoaging, and UVR-induced photocarginogenesis.

The invention also includes a method of diagnosing a disease or disorder associated with a change of Syk kinase expression in the skin of a mammal. The method comprises the step of topically administering to the skin of the mammal a pharmaceutical composition comprising a therapeutically effective amount of at least one Syk kinase inhibitor, thereby reducing the Syk kinase expression in the skin of the mammal and treating the disease or disorder.

In one embodiment, the Syk kinase inhibitor comprises an inhibitor selected from the group consisting of antibody, intrabody, siRNA, ribozyme, antisense, aptamer, peptidomimetic, small molecule, and any combination thereof. In another embodiment, the Syk kinase inhibitor is piceatannol or a salt thereof. In yet another embodiment, the mammal is a human. In yet another embodiment, the disease or disorder is selected from the group consisting of UVR-induced skin damage, UVR-induced photoaging, and UVR-induced photocarginogenesis.

The invention further includes a kit comprising a Syk kinase inhibitor and instructional material for the use thereof.

In one embodiment, the Syk kinase inhibitor is an inhibitor selected from the group consisting of an antibody, intrabody, siRNA, ribozyme, antisense, aptamer, peptidomimetic, small molecule, vitamin, and any combination thereof. In another embodiment, the Syk kinase inhibitor is piceatannol or a salt thereof. In yet another embodiment, the vitamin is selected from the group consisting of vitamin A, Vitamin C, and vitamin E.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 7, comprising FIGS. 7A-7C, is a series of images illustrating the effect of UV exposure on Syk and MMP-13 expression in skin. FIG. 7A depicts Western blot analysis of mouse skin samples blotted for Syk using anti-Syk antibody. FIG. 7B depicts the same membrane as in FIG. 7A that has been stripped and reblotted for MMP-13 expression using an anti MMP-13 antibody. FIG. 7C depicts the same membrane as shown in FIG. 7A and FIG. 7B that has been stripped and blotted for β-actin. Lanes 1-6 depict results obtained from skin samples obtained from six different hairless mice with UV exposure; lanes 7 and 8 depict results obtained from skin samples from two different hairless mice without UV exposure. Lane 9 depicts results obtained from peritoneal macrophage cells from BL6 mice.

FIG. 8, comprising FIGS. 8A-8B, illustrates the finding that overexpression of Syk enhances MMP-1 expression in human dermal fibroblasts (HDFs). FIG. 8A: HDFs were transfected with either Syk cDNA (lanes 2 and 3) or vector (lanes 1 and 4) before UVB exposure (60 mJ/cm$^2$). Syk enhances MMP-1 expression upon exposure to UVB (lane 2 vs. lane 1). Lanes 3 and 4 are the negative controls. FIG. 8B: Overexpression of Syk in HDFs transfected with Syk cDNA as shown by immunoblotting with anti-Syk antibody (upper panel). The same membrane was reblotted with anti-β-actin antibody (lower panel).

FIG. 9, comprising FIGS. 9A-9C, illustrates the finding that MMP-1 expression is decreased by piceatannol (Syk inhibitor) in human dermal fibroblasts (HDFs). FIG. 9A: Syk inhibitor piceatannol inhibits the expression of MMP-1 (lane 3). HDFs were pretreated with kinase inhibitors before UV exposure, lane 1 (control), lane 2 (SRTK inhibitor), lane 3 (Syk inhibitor), lane 4 (PI3 kinase inhibitor), and lane 5 (PKC4 inhibitor). 24 hours after UV exposure, cell culture supernatants were collected for western blot assay. Loading amount for each sample is based on the absorbance at $O.D._{280}$. FIG. 9B: Dose-dependent test for piceatannol in HDFs. HDFs were pre-incubated with different concentrations of piceatannol: 1 μg/ml, 5 μg/ml, 10 μg/ml, and 25 μg/ml respectively. 24 hours after UVB (60 mJ/cm$^2$) exposure, culture media were collected for MMP-1 assays. FIG. 9C: Western blot results in FIG. 9B were quantitated by image-density analysis.

FIG. 11, comprising As illustrated in FIG. 11A, HDFs were transiently transfected with Syk cDNA, and 48 hours after transfection exposed to UVB (60 mJ/cm$^2$). Cells were lysed at 5, 10, 25 and 45 min, post UV exposure. Cell lysates were immunoprecipitated with anti-Syk antibody, blotted with anti-tyrosine phosphorylation antibody and the membrane was stripped and reblotted with an anti-Syk antibody. FIG. 11B is a graph illustrating the activation curve of Syk in HDFs after UV exposure. Western blot results were quantitated by image-density analysis, and phospho-Syk bands were normalized by Syk protein expression.

FIG. 12, comprising FIGS. 12A-12C, illustrates the effect of Syk on MAPK activity in human dermal fibroblasts upon UV exposure. As illustrated in FIG. 12A, JNK activation was enhanced by UV exposure and Syk kinase, HDFs were transiently transfected with Syk (lanes 3 and 4) or vector control (lanes 1 and 2). 48 his after transfection cells were exposed to UVB (60 mJ/cm$^2$—Lanes 2 and 4). Cell lysates were blotted with anti-phospho-JNK antibody (upper panel), then the membrane was stripped and reblotted with anti-JNK antibody (middle panel), and with anti-β-actin antibody (lower panel). As illustrated in FIG. 12B, p38 MAPK activation was enhanced by UV exposure but not by Syk kinase transfection. Cell treatment was identical to FIG. 12A. As illustrated in FIG. 12C, Erk1/2 activation was independent of UV exposure. Cell treatment remained the same as in FIGS. 12A and 12B.

FIG. 13, comprising FIG. 13A illustrates skin samples with and without UV exposure (Panels A, B). H&E stained images before and after UV exposure (Panel C). Stratum corneum showed pronounced orthokeratosis. As illustrated in FIG. 13B, 10 week UV exposure enhanced Syk and MMP-13 expression in hairless mouse skin. Lanes 1-6: Samples (6 mice) after UV exposure. Lanes 7, 8: Samples (2 mice) without UV exposure. Lane 9: Peritoneal macrophages (BL-6 mice) over-expressing Syk (positive control) without UV exposure. FIG. 13C illustrates the image density analysis of FIG. 13B results. FIG. 13D illustrates the effect of UV exposure (5 weeks) on Syk and MMP-13 Lanes 1-7: Samples (7 mice) with UV exposure. Lanes 8-9: Samples (2 mice) without UV exposure. FIG. 13E illustrates the image density analysis of FIG. 13D results.

FIG. 16, comprising FIGS. 16A-16B, is a set of graphs illustrating the finding that Syk siRNA inhibits Syk (FIG. 16A) and MMP-1 (FIG. 16B) expression in human dermal fibroblasts.

DETAILED DESCRIPTION OF THE INVENTION

Figure 1:
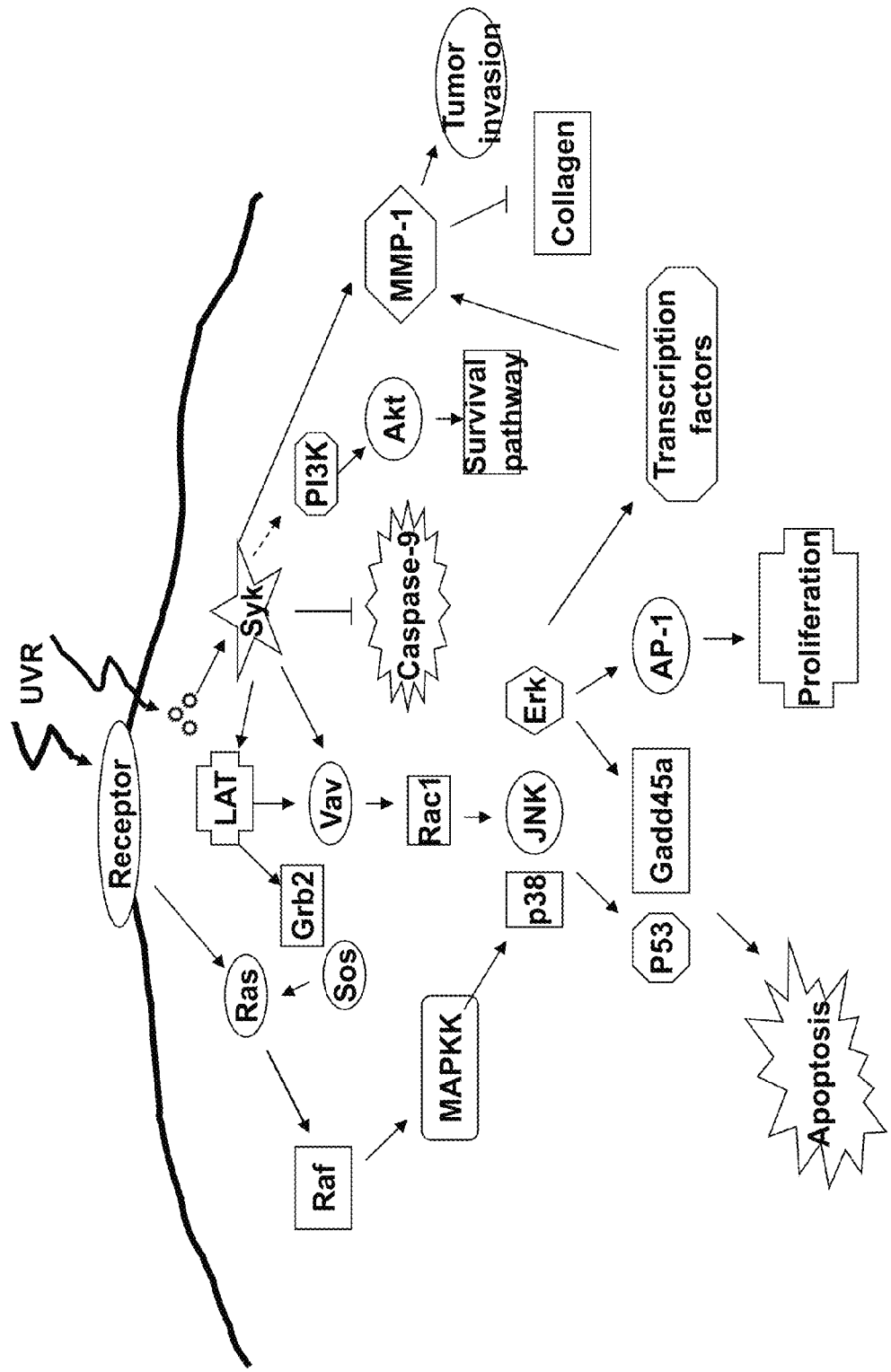
FIG. 1 is a schematic illustration depicting the ultraviolet (UV) induced signal cascade in skin, including the activation of Sky kinase by UVR.

The present invention is based on the discovery that expression of Syk kinase in skin of a subject is modulated by exposure to ultraviolet radiation (UVR). Accordingly, in one embodiment of the invention, Syk kinase is a biomarker for UVR-induced skin damage, photoaging, and photocarcinogenesis.

Accordingly, the present invention provides methods for the examination of skin cells and skin tissues, collectively known as skin samples, for the diagnosis or prognosis of UVR-induced skin damage, photoaging, or photocarcinogenesis in a subject. The invention describes a method of identifying a subject at risk of developing or afflicted with UVR induced skin damage, photoaging, or photocarcinogenesis. The method comprises obtaining a skin sample from a subject, measuring the level of Syk kinase in the skin sample, and comparing the level of Syk kinase in the sample to a control sample. Increased expression of Syk kinase in the skin sample relative to a control sample identifies the subject that the sample was obtained from as being afflicted with or at risk of developing UVR-induced skin damage, photoaging, or photocarcinogenesis. Expression of Syk kinase in a body sample is assessed at the protein or nucleic acid level.

The present invention includes a method for preventing UVR-induced skin damage, photoaging, or photocarcinogenesis in a subject where the method comprises topically administering a Syk kinase inhibitor to the skin. The present invention also further includes a method of treating UVR-induced skin damage, photoaging, or photocarcinogenesis comprising administering an effective amount of a Syk kinase inhibitor to a subject afflicted with UVR-induced skin damage.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, analytical chemistry, organic chemistry, and nucleic acid chemistry and hybridization are those well known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

Standard techniques are used for nucleic acid and peptide synthesis. The techniques and procedures are generally performed according to conventional methods in the art and various general references (e.g., Sambrook & Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

As used herein, the term "MMP" refers to matrix metalloproteinases.

As used herein, the term "UVR" refers to ultraviolet radiation.

As used herein, the term "HDFs" refers to human dermal fibroblasts.

As used herein, the term "MAPK" refers to mitogen-activated protein kinases.

As used herein, the term "pTyr" refers to phosphor-tyrosine.

As used herein, the term "ERK" refers to extracellular signal regulated kinases.

As used herein, the term "JNK" refers to c-Jun NH2-terminal kinase.

As used herein, the term "RT-PCR" refers to reverse transcription-polymerase chain reaction.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein "endogenous" refers to any material from or produced inside an organism, cell, tissue or system.

As used herein, the term "exogenous" refers to any material introduced from or produced outside an organism, cell, tissue or system.

An "amino acid" as used herein is meant to include both natural and synthetic amino acids, and both D and L amino acids, "Standard amino acid" means any of the twenty L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half life without adversely affecting activity of the peptide. Additionally, a disulfide linkage may be present or absent in the peptides.

As used herein, the terms "protein", "peptide" and "polypeptide" are used interchangeably, and refer to a compound comprised of amino acid residues covalently linked by peptide bonds. The term "peptide bond" means a covalent amide linkage formed by loss of a molecule of water between the carboxyl group of one amino acid and the amino group of a second amino acid. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Proteins" include, for example, biologically active fragments, substantially homologous proteins, oligopeptides, homodimers, heterodimers, variants of proteins, modified proteins, derivatives, analogs, and fusion proteins, among others. The proteins include natural proteins, recombinant proteins, synthetic proteins, or a combination thereof. A protein may be a receptor or a non-receptor.

As used herein, the term "fragment," as applied to a protein or peptide, refers to a subsequence of a larger protein or peptide. A "fragment" of a protein or peptide can be at least about 20 amino acids in length; for example at least about 50 amino acids in length; at least about 100 amino acids in length, at least about 200 amino acids in length, at least about 300 amino acids in length, and at least about 400 amino acids in length (and any integer value in between).

The term "recombinant polypeptide" as used herein is defined as a polypeptide produced by using recombinant DNA methods.

As used herein, a "peptidomimetic" is a compound containing non-peptidic structural elements that is capable of mimicking the biological action of a parent peptide. A peptidomimetic may or may not comprise peptide bonds.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad, Sci, USA 85:5879-5883; Bird et al., 1988, Science 242:423-426). As used herein, a "neutralizing antibody" is an immunoglobulin molecule that binds to and blocks the biological activity of the antigen.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

The term "DNA" as used herein is defined as deoxyribonucleic acid.

The term "RNA" as used herein is defined as ribonucleic acid.

The term "recombinant DNA" as used herein is defined as DNA produced by joining pieces of DNA from different sources.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anti-codon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "heterologous" as used herein is defined as DNA or RNA sequences or proteins that are derived from the different species.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. By way of example, the DNA sequences 3'ATTGCC5' and 3'TATGGC are 50% homologous.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

As used herein, "aptamer" refers to a small molecule that can bind specifically to another molecule. Aptamers are typically either polynucleotide- or peptide-based molecules.

A polynucleotidal aptamer is a DNA or RNA molecule, usually comprising several strands of nucleic acids, that adopt highly specific three-dimensional conformation designed to have appropriate binding affinities and specificities towards specific target molecules, such as peptides, proteins, drugs, vitamins, among other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

A "biomarker" of the invention is any gene or gene product that is modulated in skin in response to UVR exposure. Accordingly, using an assay to measure the level of the expression, function, or activity of a biomarker in skin is diagnostic and prognostic of UVR-induced skin damage, photoaging, or photocarcinogenesis. A biomarker may be detected at either the nucleic acid or protein level. In one embodiment, Syk kinase is a biomarker of the invention.

"Ribozymes" as used herein are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules. Ribozymes and their use for inhibiting gene expression are also well known in the art (see, e.g., Cech et al., 1992, J. Biol. Chem., 267:17479-17482; Hampel et al., 1989, Biochemistry 28:4929-4933; Eckstein et al., International Publication No. WO 92/07065; Altman et al., U.S. Pat. No. 5,168,053).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like.

The term "delivery vehicle" is used herein as a generic reference to any delivery vehicle capable of delivering a compound to a subject, including, but not limited to, dermal delivery vehicles and transdermal delivery vehicles.

As used herein, the term "dermal" refers to the skin, and in particular, the thickness of the skin from outer, dead layer, down to the bottom of the skin in direct contact with the inside of the body.

"Dermal delivery" of a substance refers to delivery of that substance into the skin, and preferably, at least into the outer, epidermal layer of skin, and more preferably, into the lower, dermal layer of skin. Therefore, "dermal delivery" of a substance refers to contacting the skin with the substance, wherein the substance penetrates at least the outermost layer of the skin. The term also refers to the delivery of the substance to additional layers of the skin, including, but not limited to, delivery of the substance all of the way down to the bottom layer in the skin in direct contact with the inside of the body.

A substance is said to be "dermally-acting" when the substance acts either on or within the skin, or both. A dermally-acting substance is not precluded from crossing the skin (i.e., "transdermal delivery") and entering the inside of the body (eg., the systemic blood circulation), although the substance may or may not enter the inside of the body.

As used herein, the term, "transdermal delivery vehicle" indicates a composition comprising at least one first compound that can facilitate transdermal delivery of at least one second compound associated with, or in close physical proximity to, the composition comprising the first compound.

Similarly, a "dermal delivery vehicle" refers to a composition comprising at least one first compound that can facilitate dermal delivery of at least one second compound associated with, or in close physical proximity to, the composition comprising the first compound.

The phrase "skin sample" as used herein, is intended to mean any sample comprising a skin cell or skin tissue in which expression of a Syk kinase gene or gene product can be detected. Skin samples may be obtained from a patient by a variety of techniques including, for example, by scraping or swabbing an areas. Methods for collecting skin samples are well known in the art.

The phrase "control sample" or "control skin sample" as used herein is used to describe a skin sample where Syk kinase expression, function, or activity has not been modulated by exposure to UVR. A control sample may be obtained from one or more normal, not-at-risk subjects, or from a skin sample obtained from the same subject at a different time or from a different location.

The term "overexpression of Syk kinase" as used herein is used describes an over-expression of Syk kinase present and detected in a skin sample obtained from a putative at-risk subject, as compared with expression of Syk kinase in a control sample obtained from one or normal, not-at-risk subjects, or from a control skin sample obtained from the same subject that has not been exposed to ultraviolet radiation. In some instances, the level of Syk kinase expression is compared with an average value obtained from more than one not-at-risk subjects. In other instances, the level of Syk kinase expression is compared with a Syk kinase level assessed in a sample obtained from one normal, not-at-risk subject. In yet another instance, the level of Syk kinase expression in the putative at-risk subject is compared with the level of Syk kinase expression in a sample obtained from the same subject at a different time or from a different location.

The phrase "at-risk" as used herein refers to a subject with a greater than average likelihood of developing UVR-induced skin damage, photoaging, or photocarcinogenesis.

A "putative at-risk subject" is a mammal, preferably a human, who is thought to be at risk of developing UVR-induced skin damage.

"Effective amount" or "therapeutically effective amount" are used interchangeably herein, and refer to an amount of a compound, formulation, material, or composition, as described herein effective to achieve a particular biological result. Such results may include, but are not limited to, the treatment of a disease or condition as determined by any means suitable in the art.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

An "individual", "patient" or "subject", as that term is used herein, includes a member of any animal species including, but are not limited to, birds, humans and other primates, and other mammals including commercially relevant mammals such as cattle, pigs, horses, sheep, cats, and dogs. Preferably, the subject is a human.

By the term "specifically binds," as used herein, is meant a molecule, such as an antibody, which recognizes and binds to another molecule or feature, but does not substantially recognize or bind other molecules or features in a sample.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

The term to "treat," as used herein, means reducing the frequency with which symptoms are experienced by a subject or administering an agent or compound to reduce the frequency and/or severity with which symptoms are experienced. As used herein, "alleviate" is used interchangeably with the term "treat." The term "therapeutic" as used herein means a treatment and/or prophylaxis. A therapeutic effect is obtained by suppression, remission, or eradication of UVR-induced skin damage.

As used herein, "treating a disease, disorder or condition" means reducing the frequency or severity with which a symptom of the disease, disorder or condition is experienced by a subject. Treating a disease, disorder or condition may or may not include complete eradication or elimination of the symptom.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the term "liposome" refers to a microscopic, fluid-filled structure, with walls comprising one or more layers of phospholipids and molecules similar in physical and/or chemical properties to those that make up mammalian cell membranes, such as, but not limited to, cholesterol, stearylamine, or phosphatidylcholine. Liposomes can be formulated to incorporate a wide range of materials as a payload either in the aqueous or in the lipid compartments.

The term "phospholipids" refers to any member of a large class of fatlike organic compounds that in their molecular structure resemble the triglycerides, except for the replacement of a fatty acid with a phosphate-containing polar group. One end of the molecule is soluble in water (hydrophilic) and water solutions. The other, fatty acid, end is soluble in fats (hydrophobic). In watery environments, phospholipids naturally combine to form a two-layer structure (lipid bilayer) with the fat-soluble ends sandwiched in the middle and the water-soluble ends sticking out. Such lipid bilayers are the structural basis of cell membranes and liposomes.

The term "sonophoresis" refers to the use of ultrasound to permeabilize skin for a prolonged period of time for the purpose of delivering compounds through the skin into the body or to allow for the sampling of interstitial fluid or its components.

The term "electroporation" refers to the transitory structural perturbation of lipid bilayer membranes due to the application of short duration, high voltage pulses for the purpose of enhancing the delivery of compounds through the skin in to the body.

The term "iontophoresis" refers to the use of a long duration low-density electrical current that attracts the ions in the compound to be delivered drives them through the skin.

The terms "permeation enhancement" and "permeation enhancers" as used herein relate to the process and added materials which bring about an increase in the permeability of skin to a poorly skin permeating pharmacologically active agent, i.e., so as to increase the rate at which the drug permeates through the skin and enters the bloodstream. "Permeation enhancer" is used interchangeably with "penetration enhancer."

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 17, 3, 4, 5, 5.3, and 6. This applies regardless of the breadth of the range.

DESCRIPTION

The present invention comprises compositions and methods useful in identifying a subject at-risk of developing UVR-induced skin damage, photoaging, or photocarcinogenesis. The method comprises using an assay to measure the level of Syk kinase expression, function, or activity in a skin sample obtained from the subject. When the level of Syk kinase expression, function, or activity is elevated in a skin sample obtained from a subject compared to the level of Syk kinase expression, function, or activity in a control skin sample, the subject is at risk of developing UVR-induced skin damage. The level of Syk kinase expression, function, or activity may be measured at either the nucleic acid (SEQ ID NO:1) or protein (SEQ ID NO:2) level. It will be understood that either the whole or a part of a Syk kinase sequence may be detected.

In another embodiment, the present invention provides compositions and methods for identifying a subject afflicted with UVR-induced skin damage, photoaging, or photocarcinogenesis. Accordingly, the present invention provides a method of detecting ultraviolet radiation (UVR)-induced skin damage in a subject, where the method comprises using an assay to measure the level of Syk kinase expression, function, or activity in a skin sample obtained from the subject. When the level of Syk kinase expression, function, or activity in a skin sample is elevated compared to the level of Syk kinase expression, function, or activity in a control skin sample, the subject is identified as being afflicted with UVR-induced skin damage.

The subject is a mammal, preferably a mouse, a rat, a non-human primate, or more preferably, a human.

The present invention also provides compositions and methods of inhibiting UVR-induced skin damage or photocarcinogenesis in a subject at risk of developing UVR-induced skin damage or photocarcinogenesis. In still another embodiment, the invention provides a method of treating a disease associated with elevated levels of Syk kinase expression, function, or activity in skin. The method comprises administering a therapeutically effective amount of a pharmaceutical composition comprising at least one Syk kinase inhibitor to a mammal having a disease associated with elevated levels of Syk kinase expression, function, or activity in skin, where a Syk kinase inhibitor attenuates, prevents, or halts the Syk kinase expression, function, or activity in the skin of said subject thereby and treating the disease associated with elevated Syk kinase expression, function, or activity in skin.

Inhibiting Syk kinase expression or activity may be accomplished using any method known to the skilled artisan. Examples of methods to inhibit Syk kinase expression or activity include, but are not limited to decreasing expression of an endogenous Syk kinase gene, decreasing expression of Syk kinase mRNA, and inhibiting activity of Syk kinase protein. Decreasing expression of an endogenous Syk kinase gene includes providing a specific inhibitor of Syk kinase gene expression. Decreasing expression of Syk kinase mRNA or Syk kinase protein includes decreasing the half-life or stability of Syk kinase mRNA or decreasing expression of Syk kinase mRNA. A Syk kinase inhibitor may therefore be a compound or composition that decreases expression of a Syk kinase gene, a compound or composition that decreases Syk kinase mRNA half-life, stability and/or expression, or a compound or composition that inhibits Syk kinase protein function. Examples of a Syk kinase inhibitor include, but are not limited to, any type of compound, including a polypeptide, a peptide, a peptidometic, a nucleic acid, an siRNA, a microRNA, an antisense nucleic acid, aptamer, a small molecule, an antibody, a ribozyme, an expression vector encoding a transdominant negative mutant, and combinations thereof. In one embodiment, the inhibitory effect of a therapeutic agent on Syk kinase expression, function, or activity is indirect. Examples of therapeutic agents that indirectly inhibit Syk kinase include a vitamin, such as vitamin A, vitamin C, and vitamin E. Accordingly, in one embodiment, a method of the invention comprises administering a therapeutically effective amount of a pharmaceutical composition comprising a vitamin to a subject, either alone or in combination with a Syk kinase inhibitor, to inhibit UVR-induced skin damage or photocarcinogenesis or treat a subject with a disease associated with elevated levels of Syk kinase expression, function, or activity in skin.

Compositions of the Invention

Syk Kinase Inhibitors: Antibodies and Intrabodies

Antibodies and intrabodies directed against Syk kinase are not just useful as inhibitors, but also are useful in the detection of Syk kinase in a skin sample, as described elsewhere, herein. It will be appreciated by one skilled in the art that an antibody comprises any immunoglobulin molecule, whether derived from natural sources or from recombinant or synthetic sources, which is able to specifically bind to an epitope present on a target molecule. In the present invention, the target molecule may be Syk kinase or fragments thereof. In one aspect of the invention, Syk kinase is directly inhibited by an antibody that specifically binds to an epitope on Syk kinase.

In certain embodiments of the invention, an antibody specific for Syk Kinase may be an antibody that is expressed as an intracellular protein. Such intracellular antibodies are also referred to as intrabodies and may comprise an Fab fragment, or preferably comprise a scFv fragment (see, e.g., Lecerf et al., Proc. Natl. Acad. Sci. USA 98:4764-49 (2001). The framework regions flanking the complementarity-determining region (CDR) regions can be modified to improve expression levels and solubility of an intrabody in an intracellular reducing environment (see, e.g., Worn et al., 2000, J. Biol. Chem. 275:2795-803). An intrabody may be directed to a particular cellular location or organelle, for example by constructing a vector that comprises a polynucleotide sequence encoding the variable regions of an intrabody that may be operatively fused to a polynucleotide sequence that encodes a particular target antigen within the cell (see, e.g., Graus-Porta et al., 1995, Mol. Cell. Biol. 15:1182-91; Lener et al., 2000, Eur. J. Biochem. 267:1196-205). An intrabody may be introduced into a cell by a variety of techniques available to the skilled artisan including via a gene therapy vector, or a lipid mixture (e.g., Provectin™, manufactured by Imgenex Corporation, San Diego, Calif.), or according to photochemical internalization methods.

When the Syk kinase inhibitor used in the compositions and methods of the invention is a polyclonal antibody (IgG), the antibody is generated by inoculating a suitable animal with a peptide comprising full length Syk kinase. These polypeptides, or fragments thereof, may be obtained by any method known in the art, including chemical synthesis and biological synthesis, as described elsewhere herein. Antibodies produced in the inoculated animal which specifically bind to Syk kinase or fragments thereof, are then isolated from fluid obtained from the animal. Antibodies may be generated in this manner in several non-human mammals such as, but not limited to goat, sheep, horse, camel, rabbit, and donkey. Methods for generating polyclonal antibodies are well known in the art and are described, for example in Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.

Monoclonal antibodies directed against a full length Syk kinase or fragment thereof, may be prepared using any well known monoclonal antibody preparation procedures, such as those described, for example, in Harlow et al., 1999, Using Antibodies: A Laboratory Manual, Cold Spring Harbor Laboratory Press, NY; Harlow et al., 1989, Antibodies: A Laboratory Manual, Cold Spring Harbor, New York and in Tuszynski et al. (1988, Blood, 72:109-115). Human monoclonal antibodies may be prepared by the method described in U.S. patent publication 2003/0224490. Monoclonal antibodies directed against an antigen are generated from mice immunized with the antigen using standard procedures as referenced herein. Nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein.

When the antibody used in the methods of the invention is a biologically active antibody fragment or a synthetic antibody corresponding to antibody to a full length Syk kinase or fragments thereof, the antibody is prepared as follows: a nucleic acid encoding the desired antibody or fragment thereof is cloned into a suitable vector. The vector is transfected into cells suitable for the generation of large quantities of the antibody or fragment thereof. DNA encoding the desired antibody is then expressed in the cell thereby producing the antibody. The nucleic acid encoding the desired peptide may be cloned and sequenced using technology which is available in the art, and described, for example, in Wright et al. (1992, Critical Rev. in Immunol. 12(3,4):125-168) and the references cited therein. Alternatively, quantities of the desired antibody or fragment thereof may also be synthesized using chemical synthesis technology. If the amino acid sequence of the antibody is known, the desired antibody can be chemically synthesized using methods known in the art as described elsewhere herein.

The present invention also includes the use of humanized antibodies specifically reactive with an epitope present on a target molecule. These antibodies are capable of binding to the target molecule. The humanized antibodies useful in the invention have a human framework and have one or more complementarity determining regions (CDRs) from an antibody, typically a mouse antibody, specifically reactive with a targeted cell surface molecule.

When the antibody used in the invention is humanized, the antibody can be generated as described in Queen, et al. (U.S. Pat. No. 6,180,370), Wright et al., (supra) and in the references cited therein, or in Gu et al. (1997, Thrombosis and Hematocyst 77(4):755-759), or using other methods of generating a humanized antibody known in the art. The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to humanized immunoglobulin coding sequences, including naturally-associated or heterologous promoter regions. The expression control sequences can be eukaryotic promoter systems in vectors capable of transforming or transfecting eukaryotic host cells, or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dialers or intact antibodies, binding fragments or other immunoglobulin forms may follow (Beychok, Cells of Immunoglobulin Synthesis, Academic Press, New York, (1979), which is incorporated herein by reference).

Human constant region (CDR) DNA sequences from a variety of human cells can be isolated in accordance with well known procedures. Preferably, the human constant region DNA sequences are isolated from immortalized B-cells as described in WO 87/02671. CDRs useful in producing the antibodies of the present invention may be similarly derived from DNA encoding monoclonal antibodies capable of binding to the target molecule. Such humanized antibodies may be generated using well known methods in any convenient mammalian source capable of producing antibodies, including, but not limited to, mice, rats, camels, llamas, rabbits, or other vertebrates. Suitable cells for constant region and framework DNA sequences and host cells in which the antibodies are expressed and secreted, can be obtained from a number of sources, such as the American Type Culture Collection, Manassas, Va.

One of skill in the art will further appreciate that the present invention encompasses the use of antibodies derived from camelid species. That is, the present invention includes, but is not limited to, the use of antibodies derived from species of the camelid family. As is well known in the art, camelid antibodies differ from those of most other mammals in that they lack a light chain, and thus comprise only heavy chains with complete and diverse antigen binding capabilities (Hamers-Casterman et al., 1993, Nature, 363:446-448). Such heavy-chain antibodies are useful in that they are smaller than conventional mammalian antibodies, they are more soluble than conventional antibodies, and further demonstrate an increased stability compared to some other antibodies. Camelid species include, but are not limited to Old World camelids, such as two-humped camels (*C. bactrianus*) and one humped camels (*C. dromedarius*). The camelid family further comprises New World camelids including, but not limited to llamas, alpacas, vicuna and guanaco. The production of polyclonal sera from camelid species is substantively similar to the production of polyclonal sera from other animals such as sheep, donkeys, goats, horses, mice, chickens, rats, and the like. The skilled artisan, when equipped with the present disclosure and the methods detailed herein, can prepare high-titers of antibodies from a camelid species.

$V_H$ proteins isolated from other sources, such as animals with heavy chain disease (Seligmann et al., 1979, immunological Rev. 48:145-167, incorporated herein by reference in its entirety), are also useful in the compositions and methods of the invention. The present invention further comprises variable heavy chain immunoglobulins produced from mice and other mammals, as detailed in Ward et al. (1989, Nature 341:544-546, incorporated herein by reference in its entirety). Briefly, $V_H$ genes are isolated from mouse splenic preparations and expressed in *E. coli*. The present invention encompasses the use of such heavy chain immunoglobulins in the compositions and methods detailed herein.

Antibodies useful as Syk kinase inhibitors in the invention may also be obtained from phage antibody libraries. To generate a phage antibody library, a cDNA library is first obtained from mRNA which is isolated from cells, e.g., the hybridoma, which express the desired protein to be expressed on the phage surface, e.g., the desired antibody. cDNA copies of the in RNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (2001, Molecular Cloning: A Laboratory Manual, Cold Spring Harbor Laboratory Press, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising say DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al., 1995, J. Mol. Biol. 248:97-105).

Once expressed, whole antibodies, dimers derived therefrom, individual light and heavy chains, or other forms of antibodies can be purified according to standard procedures known in the art. Such procedures include, but are not limited to, ammonium sulfate precipitation, the use of affinity columns, routine column chromatography, gel electrophoresis, and the like (see, generally, R. Scopes, "Protein Purification", Springer-Verlag, N.Y. (1982)). Substantially pure antibodies of at least about 90% to 95% homogeneity are preferred, and antibodies having 98% to 99% or more homogeneity most preferred for pharmaceutical uses. Once purified, the antibodies may then be used to practice the method of the invention, or to prepare a pharmaceutical composition useful in practicing the method of the invention.

The antibodies of the present invention can be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g, Current Protocols in Molecular Biology, (Ausubel et al., eds., 2002, Greene Publishing Associates and Wiley-Interscience, New York). Exemplary immunoassays are described briefly below (but are not intended to be in any way limiting).

Immunoprecipitation protocols generally comprise lysing a population cells in a lysis buffer such as RIPA buffer (1% NP-40 or TRITON™ X-100 detergent, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 14 hours) at 4° C., adding protein A and/or protein G sepharose beads to the cell lysate, incubating for about an hour of more at 4° C., washing the beads in a lysis buffer and resuspending the beads in SDS/sample buffer. The ability of the antibody of interest to immunoprecipitate a particular antigen can be assessed by, e.g., western blot analysis. Those of ordinary skill in the art will be knowledgeable as to the parameters that can be modified to increase the binding of the antibody to an antigen and decrease the background (e.g., pre-clearing the cell lysate with sepharose beads), upon consideration of the present disclosure. Additional immunoprecipitation protocols are presented Current Protocols in Molecular Biology, (Ausubel et al., 2002 Greene Publishing Associates and Wiley-Interscience, New York).

Western blot analysis generally comprises preparing protein samples, electrophoresis of the protein samples in a polyacrylamide gel (e.g., about 4-20% SDS-PAGE depending on the molecular weight of the antigen), transferring the protein sample from the polyacrylamide gel to membrane such as nitrocellulose, PVDF or nylon, blocking the membrane in blocking solution (e.g., PBS with about 5% BSA or non-fat milk), wishing the membrane in washing buffer (e.g., a solution of PBS and TWEEN®20 polysorbate detergent), blotting the membrane with primary antibody (the antibody of interest) diluted in blocking buffer, washing the membrane in washing buffer, blotting the membrane with a secondary antibody (which recognizes the primary antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. Those of ordinary skill in the art will be knowledgeable as to the parameters that can be modified to increase the signal detected and to reduce the background noise, upon consideration of the present disclosure. Additional western blot protocols are presented in Current Protocols in Molecular Biology, (Ansubel et al., 2002, Greene Publishing Associates and Wiley-Interscience, New York).

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. When performing an ELISA, the antibody of interest does not need to be conjugated to a detectable compound; instead, a second antibody (which recognizes the antibody of interest) conjugated to a detectable compound can be added to the well. Further, instead of coating the well with the antigen, the antibody may be coated to the well. In this case, a second antibody conjugated to a detectable compound can be added following the addition of the antigen of interest to the coated well. One of ordinary skill in the art will be knowledgeable as to the parameters that can be modified to increase the signal detected as well as other variations of ELISA protocols known in the art. For further discussion regarding ELISA protocols see, e.g., Current Protocols in Molecular Biology, (Ausubel et al., 2002, Greene Publishing Associates and Wiley-Interscience, New York).

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by Scatchard plot analysis. Competition with a second antibody can also be determined using radioimmunoassays. In this case, the antigen is incubated with antibody of interest conjugated to a labeled compound (e.g., $^3$H or $^{125}$I) in the presence of increasing amounts of an unlabeled second antibody.

Syk Kinase Inhibitors: siRNA

In one embodiment, siRNA is used to decrease the level of Syk kinase protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19): 306-31; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, Pa. (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of Syk kinase protein using RNAi technology.

Following the generation of the siRNA polynucleotide of the present invention, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987 Tetrahedron Lett. 28:3539-3542; Stec et al., 1985 Tetrahedron Lett. 26:2191-2194; Moody et al., 1989 Nucleic Acids Res, 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide of the invention may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl- methyl-, thio- and other modified forms of adenine, cytidine, guanine, thymine, and uridine.

Syk Kinase Inhibitors: Antisense Nucleic Acids

In one embodiment of the invention, an antisense nucleic acid sequence which is expressed by a plasmid vector is used to inhibit Syk kinase expression. The antisense expressing vector is used to transfect a mammalian cell or the mammal itself, thereby causing reduced endogenous expression of Syk kinase.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Syk Kinase Inhibitors: Ribozymes

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

In one embodiment of the invention, a ribozyme is used to inhibit Syk kinase expression. Ribozymes useful for inhibiting the expression of a target molecule may be designed by incorporating target sequences into the basic ribozyme structure which are complementary, for example, to the mRNA sequence of Syk kinase of the present invention. Ribozymes targeting Syk kinase may be synthesized using commercially available reagents (Applied Biosystems, Inc., Foster City, Calif.) or they may be genetically expressed from DNA encoding them.

Syk Kinase Inhibitors: Peptides

When the Syk kinase inhibitor is a peptide, the peptide may be chemically synthesized by Merrifield-type solid phase peptide synthesis. This method may be routinely performed to yield peptides up to about 60-70 residues in length, and may, in some cases, be utilized to make peptides up to about 100 amino acids long. Larger peptides may also be generated synthetically via fragment condensation or native chemical ligation (Dawson et al., 2000, Ann. Rev. Biochem. 69:923-960). An advantage to the utilization of a synthetic peptide route is the ability to produce large amounts of peptides, even those that rarely occur naturally, with relatively high purifies, i.e., purities sufficient for research, diagnostic or therapeutic purposes.

Solid phase peptide synthesis is described by Stewart et al. in Solid Phase Peptide Synthesis, 2nd Edition, 1984, Pierce Chemical Company, Rockford, Ill.; and Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and coupling thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group, such as formation into a carbodiimide, a symmetric acid anhydride, or an "active ester" group, such as hydroxybenzotriazole or pentafluorophenyl esters.

Examples of solid phase peptide synthesis methods include the BOC method, which utilizes tert-butyloxcarbonyl as the α-amino protecting group, and the FMOC method, which utilizes 9-fluorenylmethyloxcarbonyl to protect the α-amino of the amino acid residues. Both methods are well-known by those of skill in the art.

Incorporation of N— and/or C— blocking groups may also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin, so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB (divinylbenzene), resin, which upon hydrofluoric acid (HF) treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by trifluoroacetic acid (TFA) in dicholoromethane. Esterification of the suitably activated carboxyl function, e.g. with dicyclohexylcarbodiimide (DCC), can then proceed by addition of the desired alcohol, followed by de-protection and isolation of the esterified peptide product.

Incorporation of N-terminal blocking groups may be achieved while the synthesized peptide is still attached to the resin, for instance by treatment with a suitable anhydride and nitrite. To incorporate an acetyl blocking group at the N-terminus, for instance, the resin-coupled peptide can be treated with 20% acetic anhydride in acetonitrile. The N-blocked peptide product may then be cleaved from the resin, de-protected and subsequently isolated.

Prior to its use as a Syk kinase inhibitor in accordance with the invention, a peptide is purified to remove contaminants. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate polypeptides based on their charge. Affinity chromatography is also useful in purification procedures.

Peptides may be modified using ordinary molecular biological techniques to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The polypeptides useful in the invention may further be conjugated to non-amino acid moieties that are useful in their application. In particular, moieties that improve the stability, biological half-life, water solubility, and immunologic characteristics of the peptide are useful. A non-limiting example of such a moiety is polyethylene glycol (PEG).

Syk Kinase Inhibitors: Small Molecules

When the Syk kinase inhibitor is a small molecule, a small molecule inhibitor may be obtained using standard methods known to the skilled artisan. Such methods include chemical organic synthesis or biological means. Biological means include purification from a biological source, recombinant synthesis and in vitro translation systems, using methods well known in the art.

Combinatorial libraries of molecularly diverse chemical compounds potentially useful in treating a variety of diseases and conditions are well known in the art as are method of making said libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

Methods of the Invention

Method of Detecting UVR-Modulated Biomarkers in the Skin

The present invention relates to the use of Syk kinase as a diagnostic or prognostic biomarker to identify a subject at risk for developing or afflicted with UVR-induced skin damage, photoaging, or photocarcinogenesis.

In one embodiment, the diagnostic method of the invention comprises collecting a skin sample from a subject and analyzing the sample to measure levels of Syk kinase expression, function, or activity at the nucleic acid level or protein level.

Any method available in the art for detecting Syk kinase expression, function, or activity at the nucleic acid level or protein level is encompassed herein. The invention should not be limited to those methods for detecting Syk kinase expression, function, or activity recited herein, but rather should encompasses all known or heretofore unknown methods for detection as are, or become, known in the art.

Methods for detecting Syk kinase expression, function, or activity at the nucleic acid or protein level are well known in the art and include, but are not limited to, nucleic acid hybridization techniques, nucleic acid reverse transcription methods, and nucleic acid amplification methods, western blots, northern blots, southern blots, ELISA, immunoprecipitation, immunofluorescence, flow cytometry, immunocytochemistry. In particular embodiments, Syk kinase is detected on a protein level using, for example, antibodies that are directed against Syk kinase protein or fragments thereof. These antibodies can be used in various methods such as Western blot, ELISA, immunoprecipitation, or immunocytochemistry techniques. A description of such antibodies is disclosed elsewhere, herein.

In order to determine if Syk kinase expression, function, or activity is elevated in a skin sample, the level of Syk kinase expression, function, or activity is measured in a skin sample obtained from a subject and is compared with the level of Syk kinase measured in a control skin sample.

Protein-Based Assays for Detection of Syk Kinase

A subject may be diagnosed as being at risk for developing UVR-induced skin damage, photoaging, or photocarcinogenesis by detecting the level of expression, function, or activity of Syk kinase in a skin sample obtained from the subject. In another embodiment, a subject may be diagnosed as being afflicted with UVR-induced skin damage or photocarcinogenesis by detecting the level of expression, function, or activity of Syk kinase in a skin sample obtained from the subject.

In one embodiment, antibodies specific for a Syk kinase protein, as described elsewhere herein, are used to detect elevated levels of Syk kinase protein in a skin sample. In this method, a skin sample is obtained from a subject, the skin sample is contacted with at least one antibody directed against Syk kinase. When the level of Syk kinase is elevated in a skin sample relative to a corresponding control skin sample, the subject that the sample was obtained from is identified as being at risk for or afflicted with UVR induced skin damage, photoaging, or photocarcinogenesis. One of skill in the art will recognize that the immunocytochemistry method described herein below is performed manually or hi an automated fashion.

Samples may need to be modified in order to render the Syk kinase protein accessible to antibody binding. In a particular aspect of the immunocytochemistry methods, slides are transferred to a pretreatment buffer, for example phosphate buffered saline containing Triton-X. Incubating the sample in the pretreatment buffer rapidly disrupts the lipid bilayer of the cells and renders the antigens (i.e., Syk kinase proteins) more accessible for antibody binding. The pretreatment buffer may comprise a polymer, a detergent, or a nonionic or anionic surfactant such as, for example, an ethyloxylated anionic or nonionic surfactant, an alkanoate or an alkoxylate or even blends of these surfactants or even the use of a bile salt. The pretreatment buffers of the invention are used in methods for making antigens more accessible for antibody binding in an immunoassay, such as, for example, an immunocytochemistry method or an immunohistochemistry method.

Any method for making antigens more accessible for antibody binding may be used in the practice of the invention, including antigen retrieval methods known in the art. See, for example, Bibbo, 2002, Acta, Cytol. 46:25 29; Saqi, 2003, Diagn. Cytopathol, 27:365 370; Bibbo, 2003, Anal, Quant. Cytol. Histol. 25:8 11. In some embodiments, antigen retrieval comprises storing the slides in 95% ethanol for at least 24 hours, immersing the slides one time in Target Retrieval Solution pH 6.0 (DAKO S1699)/dH2O bath preheated to 95° C., and placing the slides in a steamer for 25 minutes.

Following pretreatment or antigen retrieval to increase antigen accessibility, samples are blocked using an appropriate blocking agent, e.g., a peroxidase blocking reagent such as hydrogen peroxide. In some embodiments, the samples are blocked using a protein blocking reagent to prevent non-specific binding of the antibody. The protein blocking reagent may comprise, for example, purified casein, serum or solution of milk proteins. An antibody directed to a biomarker of interest is then incubated with the sample.

Techniques for detecting antibody binding are well known in the art. Antibody binding to a biomarker of interest may be detected through the use of chemical reagents that generate a detectable signal that corresponds to the level of antibody binding and, accordingly, to the level of biomarker protein expression. In one of the preferred immunocytochemistry methods of the invention, antibody binding is detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell staining that corresponds to expression level of the biomarker of interest. Enzymes of particular interest include horseradish peroxidase (HRP) and alkaline phosphatase (AP). Commercial antibody detection systems, such as, for example the Dako Envision+ system (Dako North America, Inc., Carpinteria, Calif.) and Mach 3 system (Biocare Medical, Walnut Creek, Calif.), may be used to practice the present invention.

In one particular immunocytochemistry method of the invention, antibody binding to a biomarker is detected through the use of an HRP-labeled polymer that is conjugated to a secondary antibody. Antibody binding can also be detected through the use of a mouse probe reagent, which binds to mouse monoclonal antibodies, and a polymer conjugated to HRP, which binds to the mouse probe reagent. Slides are stained for antibody binding using the chromogen 3,3-diaminobenzidine (DAB) and then counterstained with hematoxylin and, optionally, a bluing agent such as ammonium hydroxide or TBS/Tween-20. In some aspects of the invention, slides are reviewed microscopically by a cytotechnologist and/or a pathologist to assess cell staining (i.e., biomarker overexpression). Alternatively, samples may be reviewed via automated microscopy or by personnel with the assistance of computer software that facilitates the identification of positive staining cells.

Detection of antibody binding can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

In regard to detection of antibody staining in the immunocytochemistry methods of the invention, there also exist in the art video-microscopy and software methods for the quantitative determination of an amount of multiple molecular species (e.g., biomarker proteins) in a biological sample, wherein each molecular species present is indicated by a representative dye marker having a specific color. Such methods are also known in the art as calorimetric analysis methods. In these methods, video-microscopy is used to provide an image of the biological sample after it has been stained to visually indicate the presence of a particular biomarker of interest. Some of these methods, such as those disclosed in U.S. Pat. No. 7,065,236 and U.S. Pat. No. 7,133,547 to Marcelpoil, incorporated herein by reference, disclose the use of an imaging system and associated software to determine the relative amounts of each molecular species present based on the presence of representative color dye markers as indicated by the color dye marker optical density or transmittance value, respectively, as determined by an imaging system and associated software. These techniques provide quantitative determinations of the relative amounts of each molecular species in a stained biological sample using a single video image that is "deconstructed" into its component color parts.

The antibodies used to practice the invention are selected to have high specificity for the biomarker proteins of interest. Methods for making antibodies and for selecting appropriate antibodies are known in the art. See, for example, Celis, J. E, ed., 2005, Cell Biology & Laboratory Handbook, 3rd edition (Academic Press, New York), which is herein incorporated in its entirety by reference. In some embodiments, commercial antibodies directed to specific biomarker proteins may be used to practice the invention. The antibodies of the invention may be selected on the basis of desirable staining of cytological, rather than histological, samples. That is, in particular embodiments the antibodies are selected with the end sample type (i.e., cytology preparations) in mind and for binding specificity.

One of skill in the art will recognize that optimization of antibody titer and detection chemistry is needed to maximize the signal to noise ratio for a particular antibody, Antibody concentrations that maximize specific binding to the biomarkers of the invention and minimize non-specific binding (or "background") will be determined in reference to the type of biological sample being tested. In particular embodiments, appropriate antibody titers for use cytology preparations are determined by initially testing various antibody dilutions on formalin-fixed paraffin-embedded normal tissue samples. Optimal antibody concentrations and detection chemistry conditions are first determined for formalin-fixed paraffin-embedded tissue samples. The design of assays to optimize antibody titer and detection conditions is standard and well within the routine capabilities of those of ordinary skill in the art. After the optimal conditions for fixed tissue samples are determined, each antibody is then used in cytology preparations under the same conditions. Some antibodies require additional optimization to reduce background staining and/or to increase specificity and sensitivity of staining in the cytology samples.

Furthermore, one of skill in the art will recognize that the concentration of a particular antibody used to practice the methods of the invention will vary depending on such factors as time for binding, level of specificity of the antibody for the biomarker protein, and method of body sample preparation. Moreover, when multiple antibodies are used, the required concentration may be affected by the order in which the antibodies are applied to the sample, i.e., simultaneously as a cocktail or sequentially as individual antibody reagents. Furthermore, the detection chemistry used to visualize antibody binding to a biomarker of interest must also be optimized to produce the desired signal to noise ratio.

As noted, it is contemplated that the biomarkers of the invention will find utility as immunogens, e.g., in immunohistochemistry and in ELISA assays. One evident utility of the encoded antigens and corresponding antibodies is in immunoassays for the detection of biomarker proteins, as needed in diagnosis and prognostic monitoring.

Immunoassays

Immunoassays, in their simplest and most direct sense, are binding assays. Certain preferred immunoassays are the various types of enzyme linked immunosorbent assays (ELISA) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, antibodies binding to the biomarker protein of the invention are immobilized onto a selected surface exhibiting protein affinity, such as a well in a polystyrene microliter plate. Then, a test composition suspected of containing the biomarker antigen, such as a clinical sample, is added to the wells. After binding and washing to remove non-specifically bound immunecomplexes, the bound antibody may be detected. Detection is generally achieved by the addition of a second antibody specific for the target protein, that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the biomarker antigen are immobilized onto the well surface and then contacted with the antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the proteins or peptides are immobilized, involves the use of antibody competition in the detection. In this ELISA, labeled antibodies are added to the wells, allowed to bind to the biomarker protein, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, the wells of the plate are incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating of nonspecific adsorption sites on the immobilizing surface reduces the background caused by nonspecific binding of antisera to the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control and/or clinical or biological sample to be tested under conditions effective to allow immunecomplex (antigen/antibody) formation. Detection of the immuneeomplex then requires a labeled secondary binding ligand or antibody, or a secondary binding ligand or antibody in conjunction with a labeled tertiary antibody or third binding ligand.

"Under conditions effective to allow immunecomplex (antigen/antibody) formation" means that the conditions preferably include diluting the antigens and antibodies with solutions such as, but not limited to, BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this label is an enzyme that generates a color or other detectable signal upon incubating with an appropriate chromogenic or other substrate. Thus, for example, the first or second immunecomplex can be detected with a urease, glucose oxidase, alkaline phosphatase or hydrogen peroxidase-conjugated antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

Nucleic Acid-Based Assays for Detection of Syk Kinase

In other embodiments, the expression of a biomarker of interest is detected at the nucleic acid level. Nucleic acid-based techniques for assessing expression are well known in the art and include, for example, determining the level of biomarker mRNA in a body sample. Many expression detection methods use isolated RNA. Any RNA isolation technique that does not select against the isolation of mRNA can be utilized for the purification of RNA from body samples (see, e.g., Ausubel et al., 2002, Current Protocols in Molecular Biology, John Wiley & Sons, NY). Additionally, large numbers of tissue samples can readily be processed using techniques well known to those of skill in the art, such as, for example, the single-step RNA isolation process of Chomczynski, 1989, U.S. Pat. No. 4,843,155).

The term "probe" refers to any molecule that is capable of selectively binding to a specifically intended target biomolecule, for example, a nucleotide transcript or a protein encoded by or corresponding to a biomarker. Probes can be synthesized by one of skill in the art, or derived from appropriate biological preparations. Probes may be specifically designed to be labeled with a detectable label. Examples of molecules that can be used as probes include, but are not limited to, RNA, DNA, proteins, antibodies, and organic molecules.

Isolated mRNA as a biomarker can be detected in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker of the present invention. Hybridization of an mRNA with the probe indicates that the biomarker in question is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array (Santa Clara, Calif.). A skilled artisan can readily adapt known mRNA detection methods for use in detecting the level of mRNA encoded by the biomarkers of the present invention.

An alternative method for determining the level of biomarker mRNA in a sample involves the process of nucleic acid amplification, e.g., by RT-PCR (the experimental embodiment set forth in Mullis, 1987, U.S. Pat. No. 4,683, 202), ligase chain reaction (Barany, 1991, Proc. Natl. Acad. Sci. USA, 88:189 193), self sustained sequence replication (Guatelli, 1990, Proc. Natl. Acad. Sci. USA, 87:1874 1878), transcriptional amplification system (Kwoh, 1989, Proc. Natl. Acad. Sci. USA, 86:1173 1177), Q-Beta Replicase (Lizardi, 1988, Bio/Technology, 6:1197), rolling circle replication (Lizardi, U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, biomarker expression is assessed by quantitative fluorogenic RT-PCR (i.e., the TaqMan™ System). Such methods typically use pairs of oligonucleotide primers that are specific for the biomarker of interest. Methods for designing oligonucleotide primers specific for a known sequence are well known in the art.

Syk kinase expression levels of RNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of biomarker expression may also comprise using nucleic acid probes in solution.

Preparation of Nucleic Acid Probes

Nucleic acid probes may be synthesized according to a number of standard methods known in the art. Oligonucleotide synthesis, is carried out on commercially available solid phase oligonucleotide synthesis machines or manually synthesized using the solid phase phosphoramidite triester method described by Beaucage, 1981, Tetrahedron Letters, 22: 1859-1862.

Once a nucleic acid encoding a biomarker is synthesized, it may be amplified and/or cloned according to standard methods in order to produce recombinant polypeptides. Molecular cloning techniques to achieve these ends are known in the art. A wide variety of cloning and in vitro amplification methods suitable for the construction of recombinant nucleic acids are known to those skilled in the art.

Examples of techniques sufficient to direct persons of skill through in vitro amplification methods, including the polymerase chain reaction (PCR), the ligase chain reaction (LCR), and other DNA or RNA polymerase-mediated techniques are found in Sambrook, 2001, Molecular Cloning: A Laboratory Manuel, $3^{rd}$ ed. (Cold Spring Harbor Laboratory Press, Cold Spring Harbor, N.Y.

Once the nucleic acid for a biomarker is cloned, a skilled artisan may express the recombinant gene(s) in a variety of engineered cells. Examples of such cells include bacteria, yeast, filamentous fungi, insect (especially employing baculoviral vectors), and mammalian cells. It is expected that those of skill in the art are knowledgeable in the numerous expression systems available for expressing the biomarker proteins of the invention.

Methods of Preventing and Treating UVR-Induced Skin Damage, Photoaging, and Photocarcinogenesis In one embodiment, the invention describes a method for the dermal delivery of a Syk kinase inhibitor for the treatment or prevention of UVR-induced skin damage. The invention further encompasses methods using delivery vehicles to deliver a Syk kinase inhibitor, alone or in combination with other compounds, to the skin in order to treat or prevent UVR-induced skin damage.

Inhibiting Syk kinase expression, function, or activity can be accomplished using any method known to the skilled artisan, as described elsewhere herein. Decreasing expression of an endogenous Syk kinase gene includes providing a specific inhibitor of Syk kinase gene expression. Syk kinase inhibition may be accomplished either directly or indirectly. For example, Syk kinase may be directly inhibited by compounds or compositions that directly interact with Syk kinase protein, such as antibodies. Alternatively, Syk kinase may be inhibited indirectly by compounds or compositions that inhibit Syk kinase downstream effectors, or upstream regulators which up-regulate Syk kinase expression.

Methods of Delivering a Syk Inhibitor to a Cell

The present invention comprises a method for treating or preventing UVR-induced skin damage or photocarcinogenesis in the skin in a mammal, said method comprising administering a therapeutic amount of a Syk kinase inhibitor.

Isolated nucleic acid-based Syk kinase inhibitors can be delivered to a cell in vitro or in vivo using viral vectors comprising one or more isolated Syk kinase inhibitor sequences. Generally, the nucleic acid sequence has been incorporated into the genome of the viral vector. The viral vector comprising an isolated Syk kinase inhibitor nucleic acid described herein can be contacted with a cell in vitro or in vivo and infection can occur. The cell can then be used experimentally to study, for example, the effect of an isolated Syk kinase inhibitor in vitro, or the cells can be implanted into a subject for therapeutic use. The cell can be migratory, such as a hematopoietic cell, or non-migratory. The cell can be present in a biological sample obtained from the subject (e.g., blood, bone marrow, tissue, fluids, organs, etc.) and used in the treatment of disease, or can be obtained from cell culture.

After contact with the viral vector comprising an isolated Syk kinase inhibitor nucleic acid sequence, the sample can be returned to the subject or re-administered to a culture of subject cells according to methods known to those practiced in the art. In the case of delivery to a subject or experimental animal model (e.g., rat, mouse, monkey, chimpanzee), such a treatment procedure is sometimes referred to as ex vivo treatment or therapy. Frequently, the cell is removed from the subject or animal and returned to the subject or animal once contacted with the viral vector comprising the isolated inhibitor nucleic acid of the present invention. Ex vivo gene therapy has been described, for example, in Kasid et al., Proc. Natl. Acad. Sci. USA 87:473 (1990); Rosenberg et al, New Engl. J. Med. 323:570 (1990); Williams et al., Nature 310476 (1984); Dick et al., Cell 42:71 (1985); Keller et al., Nature 318:149 (1985) and Anderson et al., U.S. Pat. No. 5,399,346 (1994).

Where a cell is contacted in vitro, the cell incorporating the viral vector comprising an isolated Syk kinase inhibitor nucleic acid can be implanted into a subject or experimental animal model for delivery or used in in vitro experimentation to study cellular events mediated by Syk kinase inhibitor activity.

Various viral vectors can be used to introduce an isolated Syk kinase inhibitor nucleic acid into mammalian cells. Viral vectors include retrovirus, adenovirus, parvovirus adeno-associated viruses), coronavirus, negative-strand RNA viruses such as orthomyxovirus (e.g., influenza virus), rhabdovirus (e.g., rabies and vesicular stomatitis virus), paramyxovirus (e.g., measles and Sendai), positive-strand RNA viruses such as picornavirus and alphavirus, and double stranded DNA viruses including adenovirus, herpesvirus (e.g., herpes simplex virus types 1 and 2, Epstein-Barr virus, cytomegalovirus), and poxvirus (e.g. vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus, lentiviruses and baculoviruses.

In addition, an engineered viral vector can be used to deliver an isolated Syk kinase inhibitor nucleic acid of the present invention. These vectors provide a means to introduce nucleic acids into cycling and quiescent cells, and have been modified to reduce cytotoxicity and to improve genetic stability. The preparation and use of engineered Herpes simplex virus type 1 (Krisky et al., 1997, Gene Therapy 4:1120-1125), adenoviral (Amalfitanl et al., 1998, Journal of Virology 72:926-933) attenuated lentiviral (Zufferey et al., 1997, Nature Biotechnology 15:871-875) and adenoviral/retroviral chimeric (Feng et al., 1997, Nature Biotechnology 15:866-870) vectors are known to the skilled artisan. In addition to delivery through the use of vectors, an isolated Syk kinase inhibitor nucleic acid can be delivered to cells without vectors, e.g. as "naked" nucleic acid delivery using methods known to those of skill in the art. See, for example, U.S. Pat. Nos. 5,350,674 and 5,585,362.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al., 2002, Current Protocols in Molecular Biology, John Wiley & Sons, NY).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Various forms of an isolated Syk kinase inhibitor nucleic acid, as described herein, can be administered or delivered to a mammalian cell (e.g., by virus, direct injection, or liposomes, or by any other suitable methods known in the art or later developed). The methods of delivery can be modified to target certain cells, and in particular, cell surface receptor molecules. As an example, the use of cationic lipids as a carrier for nucleic acid constructs provides an efficient means of delivering the isolated TLR agonist nucleic acid of the present invention.

Various formulations of cationic lipids have been used to deliver nucleic acids to cells (WO 91/17424; WO 91/16024; U.S. Pat. Nos. 4,897,355; 4,946,787; 5,049,386; and 5,208,036). Cationic lipids have also been used to introduce foreign polynucleotides into frog and rat cells in vivo (Holt et al., Neuron 4:203-214 (1990); Hazinski et al., *Am. J. Respr, Cell. Mol. Biol.* 4:206-209 (1991)). Therefore, cationic lipids may be used, generally, as pharmaceutical carriers to provide biologically active substances (for example, see WO 91/17424; WO 91/16024; and WO 93/03709). Thus, cationic liposomes can provide an efficient carrier for the introduction of polynucleotides into a cell.

Further, liposomes can be used as carriers to deliver a nucleic acid to a cell, tissue or organ. Liposomes comprising neutral or anionic lipids do not generally fuse with the target cell surface, but are taken up phagocytically, and the polynucleotides are subsequently subjected to the degradative enzymes of the lysosomal compartment (Straubinger et al., 1983, *Methods Enzymol.* 101:512-527; Mannino et al., 1988, *Biotechniques* 6:682-690). Methods of delivering a nucleic acid to a cell, tissue or organism, including liposome-mediated delivery, are known in the art and are described in, for example, Felgner (*Gene Transfer and Expression Protocols Vol.* 7, Murray, E. J. Ed., Humana Press, New Jersey, (1991)).

In other related aspects, the invention includes an isolated Syk kinase inhibitor nucleic acid operably linked to a nucleic acid comprising a promoter/regulatory sequence such that the nucleic acid is preferably capable of delivering an isolated Syk kinase inhibitor nucleic acid. Thus, the invention encompasses expression vectors and methods for the introduction of an isolated Syk kinase inhibitor nucleic acid into or to cells.

Such delivery can be accomplished by generating a plasmid, viral, or other type of vector comprising an isolated Syk kinase inhibitor nucleic acid operably linked to a promoter/regulatory sequence which serves to introduce the Syk kinase inhibitor into cells in which the vector is introduced. Many promoter/regulatory sequences useful for the methods of the present invention are available in the art and include, but are not limited to, for example, the cytomegalovirus immediate early promoter enhancer sequence, the SV40 early promoter, as well as the Rous sarcoma virus promoter, and the like. Moreover, inducible and tissue specific expression of an isolated Syk kinase inhibitor nucleic acid may be accomplished by placing an isolated Syk kinase inhibitor nucleic acid, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Selection of any particular plasmid vector or other vector is not a limiting factor in this invention and a wide plethora of vectors are well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (2001, Molecular Cloning: A Laboratory Manual, Cold Spring Harbor Laboratory, New York), and in Ausubel et al., 2002, Current Protocols in Molecular Biology, John Wiley & Sons, NY and elsewhere herein.

A Syk kinase inhibitor that is a peptide, polypeptide or protein can be supplied to cells. Protein can be produced by expression of the cDNA sequence in bacteria, for example, using known expression vectors. Alternatively, a Syk kinase inhibitor polypeptide can be extracted from Syk kinase inhibitor-producing mammalian cells. In addition, the techniques of synthetic chemistry can be employed to synthesize Syk kinase inhibitor protein. Any of such techniques can provide the preparation of the present invention which comprises the Syk kinase inhibitor protein. The preparation is substantially free of other human proteins. This is most readily accomplished by synthesis in a microorganism or in vitro.

Active Syk kinase inhibitor protein can be introduced into cells by microinjection or by use of liposomes, for example. Alternatively, some active molecules may be taken up by cells, actively or by diffusion. Modified polypeptides having substantially similar function are also used for peptide therapy.

Combined with certain formulations, a peptide or protein, such as an antibody, which has Syk kinase inhibitor activity can be effective intracellular agents if provided as a fusion protein along with a second peptide that promotes "transcytosis", e.g., uptake of the peptide by epithelial cells. To illustrate, an antibody that inhibits Syk kinase activity can be provided as part of a fusion polypeptide with all or a fragment of the N-terminal domain of the HIV protein Tat, e.g., residues 1-72 of Tat or a smaller fragment thereof which can promote transcytosis. In other embodiments, an antibody that inhibits Syk kinase activity can be provided a fusion polypeptide with all or a portion of the antenopedia III protein.

To further illustrate, a Syk kinase inhibitor peptide, polypeptide, or protein (or peptidomimetic) can be provided as a chimeric peptide which includes a heterologous peptide sequence ("internalizing peptide") which drives the translocation of an extracellular form of a peptide with Syk kinase inhibitory activity across a cell membrane in order to facilitate intracellular localization of the peptide with Syk kinase inhibitory activity. In this regard, the therapeutic peptide with Syk kinase inhibitory activity binding sequence is one which is active intracellularly. The internalizing peptide, by itself, is capable of crossing a cellular membrane by, e.g., transcytosis, at a relatively high rate. The internalizing peptide is conjugated, e.g., as a fusion protein, to the peptide or protein with Syk kinase inhibitory activity. The resulting chimeric peptide is transported into cells at a higher rate relative to the activator polypeptide alone to thereby provide a means for enhancing its introduction into cells to which it is applied.

In one embodiment, the internalizing peptide is derived from the *Drosophila* antennapedia protein, or homologs thereof. The 60 amino acid long homeodomain of the homeo-protein antennapedia has been demonstrated to translocate through biological membranes and can facilitate the translocation of heterologous polypeptides to which it is couples. See for example Derossi et al. (1994) J Biol Chem 269:10444-10450; and Perez et al. (1992) J Cell Sci 102: 717-722. Recently, it has been demonstrated that fragments as small as 16 amino acids long of this protein are sufficient to drive internalization. See Derossi et al. (1996) J Biol Chem 271:18188-18193.

The present invention contemplates a peptide or protein, such as an antibody, with Syk kinase inhibitory activity or peptidomimetic sequence as described herein, and at least a portion of the Antennapedia protein (or homolog thereof) sufficient to increase the transmembrane transport of the chimeric protein, relative to the peptide with Syk kinase inhibitory activity or peptidomimetic, by a statistically significant amount.

Another example of an internalizing peptide is the HIV transactivator (TAT) protein. This protein appears to be divided into four domains (Kuppuswamy et al. (1989) Nucl. Acids Res. 17:3551-3561). Purified TAT protein is taken up by cells in tissue culture (Frankel and Pabo, (1989) Cell, 55:1189-1193), and peptides, such as the fragment corresponding to residues 37-62 of TAT, are rapidly taken up by cell in vitro (Green and Loewenstein, (1989) Cell 55:1179-1188). The highly basic region mediates internalization and targeting of the internalizing moiety to the nucleus (Ruben et al., (1989) J. Virol. 63:1-8).

Another exemplary transcellular polypeptide can be generated to include a sufficient portion of mastoparan (T. Higashijima et al., (1990) J. Biol. Chem. 265:14176) to increase the transmembrane transport of the chimeric protein.

While not wishing to be bound by any particular theory, it is noted that hydrophilic polypeptides may be also be physiologically transported across the membrane barriers by coupling or conjugating the polypeptide to a transportable peptide which is capable of crossing the membrane by receptor-mediated transcytosis. Suitable internalizing peptides of this type can be generated using all or a portion of, e.g., a histone, insulin, transferrin, basic albumin, prolactin and insulin-like growth factor I (IGF-I), insulin-like growth factor II (IGF-II) or other growth factors. For instance, it has been found that an insulin fragment, showing affinity for the insulin receptor on capillary cells, and being less effective than insulin in blood sugar reduction, is capable of transmembrane transport by receptor-mediated transcytosis and can therefore serve as an internalizing peptide for the subject transcellular peptides and peptidomimetics. Preferred growth factor-derived internalizing peptides include EGF (epidermal growth factor)-derived peptides, such as CMHIESLDSYTC (SEQ ID NO:3) and CMYIEALDKYAC (SEQ ID NO:4); TGF-beta (transforming growth factor beta)-derived peptides; peptides derived from PDGF (platelet-derived growth factor) or PDGF-2; peptides derived from IGF-I (insulin-like growth factor) or IGF-II; and FGF (fibroblast growth factor)-derived peptides.

Another class of translocating/internalizing peptides exhibits pH-dependent membrane binding. For an internalizing peptide that assumes a helical conformation at an acidic pH, the internalizing peptide acquires the property of amphiphilicity, e.g., it has both hydrophobic and hydrophilic interfaces. More specifically, within a pH range of approximately 5.0-5.5, an internalizing peptide forms an alpha-helical, amphiphilic structure that facilitates insertion of the moiety into a target membrane. An alpha-helix-inducing acidic pH environment may be found, for example, in the low pH environment present within cellular endosomes. Such internalizing peptides can be used to facilitate transport of peptide with Syk kinase inhibitory activity and peptidomimetics, taken up by an endocytic mechanism, from endosomal compartments to the cytoplasm.

A preferred pH-dependent membrane-binding internalizing peptide includes a high percentage of helix-forming residues, such as glutamate, methionine, alanine and leucine. In addition, a preferred internalizing peptide sequence includes ionizable residues having pKa's within the range of pH 5-7, so that a sufficient uncharged membrane-binding domain will be present within the peptide at pH 5 to allow insertion into the target cell membrane.

A particularly preferred pH-dependent membrane-binding internalizing peptide in this regard is aa1-aa2-aa3-EAALA(EALA)4-EALEALAA-amide, which represents a modification of the peptide sequence of Subbarao et al. (Biochemistry 26:2964, 1987). Within this peptide sequence, the first amino acid residue (aa1) is preferably a unique residue, such as cysteine or lysine, that facilitates chemical conjugation of the internalizing peptide to a targeting protein conjugate. Amino acid residues 2-3 may be selected to modulate the affinity of the internalizing peptide for different membranes. For instance, if both residues 2 and 3 are lys or arg, the internalizing peptide will have the capacity to bind to membranes or patches of lipids having a negative surface charge. If residues 2-3 are neutral amino acids, the internalizing peptide will insert into neutral membranes.

Yet other preferred internalizing peptides include peptides of apo-lipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention include hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of the covalently linked polypeptide into the cell cytoplasm. Such internalizing peptides may be modeled after sequences identified in, e.g., *Pseudomonas* exotoxin A, clathrin, or Diphtheria toxin.

Pore-forming proteins or peptides may also serve as internalizing peptides herein. Pore-forming proteins or peptides may be obtained or derived from, for example, C9 complement protein, cytolytic T-cell molecules or NK-cell molecules. These moieties are capable of forming ring-like structures in membranes, thereby allowing transport of attached polypeptide through the membrane and into the cell interior.

Mere membrane intercalation of an internalizing peptide may be sufficient for translocation of the peptide with Syk kinase inhibitory activity or peptidomimetic, across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a translocating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

An exemplary accessory moiety in this regard would be a peptide substrate for N-myristoyl transferase, such as GNAAAARR (SEQ ID NO:5) (Eubanks et al., in: Peptides, Chemistry and Biology, Garland Marshall (ed.), ESCOM, Leiden, 1988, pp. 566-69) In this construct, an internalizing peptide would be attached to the C-terminus of the accessory peptide, since the N-terminal glycine is critical for the accessory moiety's activity. This hybrid peptide, upon attachment to an E2 peptide or peptidomimetic at its C-terminus, is N-myristylated and further anchored to the target cell membrane, e.g., it serves to increase the local concentration of the peptide at the cell membrane.

To further illustrate use of an accessory peptide, a phosphorylatable accessory peptide is first covalently attached to the C-terminus of an internalizing peptide and then incorporated into a fusion protein with a peptide with Syk kinase inhibitory activity or peptidomimetic. The peptide component of the fusion protein intercalates into the target cell plasma membrane and, as a result, the accessory peptide is translocated across the membrane and protrudes into the cytoplasm of the target cell. On the cytoplasmic side of the plasma membrane, the accessory peptide is phosphorylated by cellular kinases at neutral pH. Once phosphorylated, the accessory peptide acts to irreversibly anchor the fusion protein into the membrane. Localization to the cell surface membrane can enhance the translocation of the polypeptide into the cell cytoplasm.

Suitable accessory peptides include peptides that are kinase substrates, peptides that possess a single positive charge, and peptides that contain sequences which are glycosylated by membrane-bound glycotransferases. Accessory peptides that are glycosylated by membrane-bound glycotransferases may include the sequence x-NLT-x, where "x" may be another peptide, an amino acid, coupling agent or hydrophobic molecule, for example. When this hydrophobic tripeptide is incubated with microsomal vesicles, it crosses vesicular membranes, is glycosylated on the luminal side, and is entrapped within the vesicles due to its hydrophilicity (C. Hirschberg et al., (1987) Ann. Rev. Biochem. 56:63-87). Accessory peptides that contain the sequence x-NLT-x thus will enhance target cell retention of corresponding polypeptide.

In another embodiment of this aspect of the invention, an accessory peptide can be used to enhance interaction of the peptide with Syk kinase inhibitory activity or peptidomimetic with the target cell. Exemplary accessory peptides in this regard include peptides derived from cell adhesion proteins containing the sequence "RGD", or peptides derived from laminin containing the sequence CDPGYIG-SRC (SEQ ID NO:6). Extracellular matrix glycoproteins, such as fibronectin and laminin, bind to cell surfaces through receptor-mediated processes. A tripeptide sequence, RGD, has been identified as necessary for binding to cell surface receptors. This sequence is present in fibronectin, vitronectin, C3bl of complement, von-Willebrand factor, EGF receptor, transforming growth factor beta, collagen type 1, lambda receptor of *E. Coli*, fibrinogen and Sindbis coat protein (E. Ruoslahti, Ann. Rev. Biochem. 57:375413, 1988). Cell surface receptors that recognize RGD sequences have been grouped into a superfamily of related proteins designated "integrins". Binding of "RGD peptides" to cell surface integrins will promote cell-surface retention, and ultimately translocation, of the polypeptide.

As described above, the internalizing and accessory peptides can each, independently, be added to the peptide or protein with Syk kinase inhibitory activity or peptidomimetic by either chemical cross-linking or in the form of a fusion protein. In the instance of fusion proteins, unstructured polypeptide linkers can be included between each of the peptide moieties.

In general, the internalization peptide will be sufficient to also direct export of the polypeptide. However, where an accessory peptide is provided, such as an RGD sequence, it may be necessary to include a secretion signal sequence to direct export of the fusion protein from its host cell. In preferred embodiments, the secretion signal sequence is located at the extreme N-terminus, and is (optionally) flanked by a proteolytic site between the secretion signal and the rest of the fusion protein.

In the generation of fusion polypeptides including a peptide with Syk kinase inhibitory activity, it may be necessary to include unstructured linkers in order to ensure proper folding of the various peptide domains. Many synthetic and natural linkers are known in the art and can be adapted for use in the present invention, including the $(Gly_3Ser)_4$ linker.

Pharmaceutical Compositions and Therapies

Administration of a Syk kinase inhibitor comprising one or more peptides, small molecules, antisense nucleic acids, or antibodies of the invention in a method of treatment may be achieved in a number of different ways, using methods known in the art. Such methods include, but are not limited to, providing an exogenous peptide inhibitor, small molecule, or antibody to a subject or expressing a recombinant peptide inhibitor, small molecule, soluble receptor, or antibody expression cassette.

The therapeutic and prophylactic methods of the invention thus encompass the use of pharmaceutical compositions comprising Syk kinase inhibitor peptide, fusion protein, small molecule, or antibody of the invention and/or an isolated nucleic acid encoding a Syk kinase inhibitory peptide, fusion protein small molecule, or antibody of the invention to practice the methods of the invention. The pharmaceutical compositions useful for practicing the invention may be administered to deliver a dose of 1 ng/kg/day to 100 mg/kg/day. In one embodiment, the invention envisions administration of a dose that results in a concentration of the compound of the present invention between 1 μM and 10 μM in a mammal, preferably a human.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Typically, dosages which may be administered in a method of the invention to an animal, preferably a human, range in amount from 0.5 μg to about 50 mg per kilogram of body weight of the animal. While the precise dosage administered will vary depending upon any number of factors, including but not limited to, the type of animal and type of disease state being treated, the age of the animal and the route of administration, the dosage of the compound will preferably vary from about 1 μg to about 10 mg per kilogram of body weight of the animal. More preferably, the dosage will vary from about 3 μg to about 1 mg per kilogram of body weight of the animal.

Pharmaceutical compositions that are useful in the methods of the invention may be prepared, packaged, or sold in formulations suitable for oral, parenteral, topical, buccal, or another route of administration. Other contemplated formulations include projected nanoparticles, liposomal preparations, resealed erythrocytes containing the active ingredient, and immunologically-based formulations.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxyeetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Controlled- or sustained-release formulations of a composition of the invention may be made using conventional technology, in addition to the disclosure set forth elsewhere herein. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the compositions of the invention.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, nanoparticles, or microspheres or a combination thereof that facilitates the controlled-release of the active ingredient.

Administration/Dosing

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a composition of the invention, alone or in combination with a second pharmaceutical agent; and instructions for using the composition to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject.

Routes of Administration

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

A pharmaceutical composition of the invention may be prepared, packaged, or sold in a formulation suitable for topical administration. There are several advantages to delivering compounds, including drugs or other therapeutic agents, into the skin (dermal drug delivery) or into the body through the skin (transdermal drug delivery). Transdermal compound delivery offers an attractive alternative to injections and oral medications. Dermal compound delivery offers an efficient way to deliver a compound to the skin of a mammal, and preferably a human, and provides a method of treatment of the skin, or otherwise provides a method of affecting the skin, without the need to break or damage the outer layer of the skin. In the present invention, dermal delivery, by way of a dermally-acting compound of the invention, provides these advantages for treatment of a skin-related condition, disorder or disease.

A number of compounds, including some drugs, will penetrate the skin effectively simply because the molecules are relatively small and potent at small doses of 0.1 mg to 15 mg/day (Kanikkannan et al., 2000, Curr. Med. Chem. 7:593-608). Many other compounds and drugs can be delivered only when an additional enhancement system is provided to "force" them to pass through the skin. Among several methods of transdermal drug delivery are electroporation, sonophoresis, iontophoresis, permeation enhancers (cyclodextrins), and liposomes. While the aforementioned methods are also included in the present invention for dermal delivery of the compounds of the invention, liposomes represent a preferred dermal delivery method.

In one aspect of the invention, a dermally-acting composition is provided for treatment or prevention of UVR-induced skin damage, wherein the composition comprises a Syk kinase inhibitor and a delivery vehicle. In one aspect, a dermally-acting composition is provided for treatment or prevention of UVR-induced skin damage, wherein the composition comprises a Syk kinase inhibitor as an active ingredient and a liposome component. In one embodiment, a Syk kinase inhibitor is piceatannol or a salt thereof.

The invention encompasses the preparation and use of a dermally-acting composition comprising a compound useful for the treatment or prevention of UVR-induced skin damage. Such a composition may consist of the active ingredient alone, in a form suitable for administration to a subject, or the composition may comprise at least one active ingredient and one or more pharmaceutically acceptable carriers, one or more additional ingredients, or some combination of these. The active ingredient may be present in the composition in the form of a physiologically acceptable ester or salt, such as in combination with a physiologically acceptable cation or anion, as is well known in the art. Compositions of the invention will also be understood to encompass pharmaceutical compositions useful for treatment of other conditions, disorders and diseases associated with the skin.

In one aspect, a dermal delivery vehicle of the invention is a composition comprising at least one first compound that can facilitate dermal delivery of at least one second compound associated with, or in close physical proximity to, the composition comprising the first compound. As will be understood by the skilled artisan, when armed with the disclosure set forth herein, such delivery vehicles include, but should not be limited to, liposomes, nanosomes, phosopholipid-based non-liposome compositions (eg., selected cochleates), among others.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 0.001% to about 90% (w/w) active ingredient, although the concentration of the active ingredient may be as high as the solubility limit of the active ingredient in the solvent. Formulations for topical administration may further comprise one or more of the additional ingredients described herein.

In one aspect of the invention, a dermal delivery system includes a liposome delivery system, and that the present invention should not be construed to be limited to any particular liposome delivery system. Based on the disclosure set forth herein, the skilled artisan will understand how to identify a liposome delivery system as being useful in the present invention.

The present invention also encompasses the improvement of dermal and transdermal drug delivery through the use of penetration enhancers (also called sorption promoters or accelerants), which penetrate into skin to reversibly decrease the barrier resistance. Many compounds are known in the art for penetration enhancing activity, including sulphoxides (such as dimethylsulphoxide, DMSO), azones (e.g. laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and terpenes. Other enhancers include oleic acid, oleyl alcohol, ethoxydiglycol, laurocapram, alkanecarboxylic acids, dimethylsulfoxide, polar lipids, or N-methyl-2-pyrrolidone.

In alternative embodiments, the topically active pharmaceutical or cosmetic composition may be optionally combined with other ingredients such as moisturizers, cosmetic adjuvants, anti-oxidants, chelating agents, surfactants, foaming agents, conditioners, humectants, wetting agents, emulsifying agents, fragrances, viscosifiers, buffering agents, preservatives, sunscreens and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art.

In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art. The compositions of this invention may also contain active amounts of retinoids (i.e., compounds that bind to any members of the family of retinoid receptors), including, for example, tretinoin, retinol, esters of tretinoin and/or retinol and the like.

The composition of the invention may comprise a preservative from about 0.005% to 2.0% by total weight of the composition. The preservative is used to prevent spoilage in the case of an aqueous gel because of repeated patient use when it is exposed to contaminants in the environment from, for example, exposure to air or the patient's skin, including contact with the fingers used for applying a composition of the invention such as a therapeutic gel or cream. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound for use in the invention in the aqueous gel formulation. Preferred antioxidants for some compounds are BHT, BHA, alpha-tocopherol and ascorbic acid in the preferred range of about 0.01% to 5% and BHT in the range of 0.01% to 1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Additional components may include, but should not be limited to those including water, oil (eg., olive oil/PEG7), biovera oil, wax (eg., jojoba wax), squalene, myristate (eg., isopropyl myristate), triglycerides (eg., caprylie triglyceride), Solulan 98, cocoa butter, shea butter, alcohol (eg., behenyl alcohol), stearate (eg., glycerolmonostearate), chelating agents (eg., EDTA), propylene glycol, SEPIGEL (Seppic, Inc., Fairfield, N.J.), silicone and silicone derivatives (eg., dimethicone, cyclomethicone), vitamins (eg., vitamin E), among others.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Buccal Administration

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Vaginal Administration

A pharmaceutical composition of the invention may be prepared, packaged, or sold in a formulation suitable for vaginal administration. With respect to the vaginal or perivaginal administration of the compounds of the invention, dosage forms may include vaginal suppositories, creams, ointments, liquid formulations, pessaries, tampons, gels, pastes, foams or sprays. The suppository, solution, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909), The vaginal or perivaginal dosage unit may be fabricated to disintegrate rapidly or over a period of several hours. The time period for complete disintegration may be in the range of from about 10 minutes to about 6 hours, e.g., less than about 3 hours.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives.

Additional Administration Forms

Additional dosage forms of this invention include dosage forms as described in U.S. Pat. Nos. 6,340,475; 6,488,962; 6,451,808; 5,972,389; 5,582,837 and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Kits of the Invention

The invention also includes a kit comprising a Syk kinase inhibitor and an instructional material that describes, for instance, administering the Syk kinase inhibitor to a subject as a prophylactic or therapeutic treatment or a non-treatment use as described elsewhere herein. In an embodiment, the kit further comprises a (preferably sterile) pharmaceutically acceptable carrier suitable for dissolving or suspending the therapeutic composition, comprising a Syk kinase inhibitor, for instance, prior to administering the molecule to a subject. Optionally, the kit comprises an applicator for administering the inhibitor.

In another embodiment, the kit comprises compositions required for the detection of Syk kinase expression, function, or activity in a skin sample invention and an instructional material which describes, for instance, the method for detecting Syk kinase expression, function, or activity in skin as described elsewhere herein.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in the experiments and the results of the experiments presented in this Example are now described, Antibodies:

The following antibodies were used in this study: MMP-1 and MMP-13 antibodies (Calbiochem, UK), Syk and β-actin (Santa Cruz Biotechnology Inc., Santa Cruz, Calif.), phospho-JNK, phsopho-p38, phospho-Erk1/2 and JNK (Cell Signaling Technology, Danvers, Mass.), phosphotyrosine (Millipore, Billerica, Mass.).

Cell Culture, Transfection and UVR Treatment:

Human dermal fibroblasts AG04058 (Coriell Institute for Medical Research, Camden, N.J.) were cultured and maintained in MEM containing glucose (4.5 mg/ml), glutamine (2 mM), streptomycin (100 U/ml), penicillin (100 µg/ml), and 10% heat-inactivated fetal bovine serum. For cell transfection, Fugene 6 transfection kit (Roche, Germany) was used to deliver Syk cDNA and the Saint-Red siRNA delivery system (Synvolux Therapeutics B.V., The Netherlands) was chosen to transfect Syk siRNA and control siRNA (Santa Cruz Biotechnology Inc., Santa Cruz, Calif.) into the cells. Cells were exposed to UVB (312 nm) (60 mJ/cm$^2$) by a Stratalinker UV Crosslinker (Stratagene, La Jolla, Calif.). Cell supernatants were collected 24 hrs after UV exposure, and prepared for MMP-1 expression assay.

Animal Experiments and UVR Treatment:

The SKH1 hairless mouse is a well-established animal model to study UV-induced damage in skin (Gruijl & Forbes, 1995, Bioessays 17:651-60). SKH1 female albino hairless mice were obtained from Charles River Laboratory, allowed to acclimatize for a week before the start of the experiments, then randomly separated into two groups. Animals in the UV treated group were exposed to UVR three times a week at the dosages shown in Table 1. The Solar Simulator used has a spectral output of 97% UVA and 3% UVB (Papazoglou et al., 2010, Photochem Photobiol 86:138-45), which is similar to that of solar UV radiation. At the end of 5 and 10 weeks, animals were sacrificed, and UV exposed and unexposed skin samples were removed and subjected to flash-freezing in liquid nitrogen. The samples were used for further western blot assays.

Syk mRNA Assay by RT-PC:

For the mRNA assay, cells were treated with 300 µl Trizol solution (Invitrogen, Carlsbad, Calif.) for 7 min. After 250 µl chloroform addition, samples were centrifuged at 12,000 rpm for 20 minutes at 4° C. The upper phase was transferred into a new RNase free tube and RNA was precipitated by isopropanol for 10 min. After centrifugation at 12,000 rpm for 15 min, the pellets were washed once with 75% ethanol. The RNA pellets were dissolved into DSPC-treated water for further experiments. The RT-PCR (reverse transcription DNA polymerase chain reaction) assays were performed by the Superscript one-step RT-PCR with Platinum Taq kit (Invitrogen, Carlsbad, Calif.). Results were imaged in 1% agarose gel (electrophoresis). The primers used for this experiment are as follows:

```
Syk forward primer:
5'-TTTTGGAGGCCGTCCACAAC-3';      (SEQ ID NO: 7)

Syk reverse primer:
5'-TGCATGACATTTGCTTCTGCTAAT-3';  (SEQ ID NO: 8)

Actin forward primer:
5'-GCTCCGGCATGTGCAA-3';          (SEQ ID NO: 9)

Actin reverse primer:
5'-AGGATCTTCATGAGGTAGT-3.        (SEQ ID NO: 10)
```

Immunoprecipitation and Western Blot:

Twenty-four hours after UV exposure, the culture media of HDFs were collected for MMP-1 assay. Based on $OD_{280}$ measurement, equal amounts of proteins from the supernatants were mixed with 2× sample buffer, boiled for 5 min and chilled on ice. Samples were then subjected to 4-1% SDS-PAGE and electrophoretically transferred to nitrocellulose membrane. The membrane was blocked with 5% dry milk in washing buffer. MMP-1 was detected with anti-MMP-1 antibody, and the results were visualized by an ECL detection system. For Syk protein and MAPK activation western blot assays, cell pellets were lysed in 1× Triton X-100 lysis buffer (1% Triton X-100, 5 mmol/L Hepes—KOH, pH 7.4) in the presence of protease and phosphatase inhibitors containing 5 mM EGTA, 3 mM Na orthovanadate, 2 mM phenylmethylsulfonyl fluoride, and 10 µg/L aprotinin and leupeptin (Sigma Chemical Co., St. Louis, Mo.). Following centrifugation at 12,000 rpm for 30 min at 4° C., the cleared lysates were subjected to the same procedure as that followed for MMP-1 assay. Syk protein and MAPK activation were detected with anti-Syk antibody and anti-phospho-MAPK antibodies, respectively, by western blot. For the activation of Syk kinase assay, briefly, cell lysates were precleared by incubation with protein G plus agarose (Santa Cruz Biotechnology, Inc.), and then incubated overnight at 4° C. with anti-Syk antibody. Immune complexes would bind to protein G plus agarose in the lysis buffer. The agarose beads were washed three times with lysis buffer and the adsorbed proteins were eluted into the sample buffer. Tyrosine phosphorylation of Syk kinase (Syk activation) was determined with anti-phosphotyrosine antibody by western blot.

Experimental Example 1

Determination of UVA/UVB Dosage for Fibroblast Cells

Mouse fibroblast cells NIH3T3 (CRL-1658, ATCC) and Monkey kidney fibroblast cells COS-1 (CRL-1650, ATCC) were seeded into 4 cm tissue culture dishes in provided DMEM medium one day prior to UVR treatment. The cells were exposed to different dosages of UVR, provided by a Solar Stimulator (Abbott Laboratories, North Chicago, Ill.).

Figure 2:
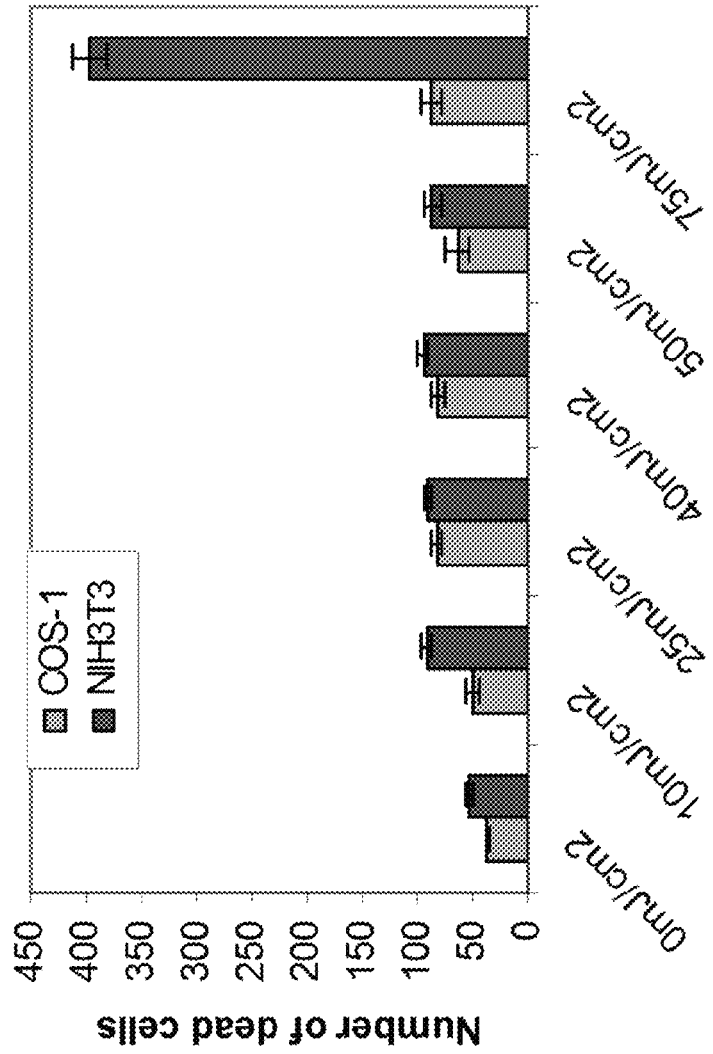
FIG. 2 is a bar graph illustrating the effect of UV dosage on fibroblast cell viability in COS-1 (light gray) and NIH3T3 (dark gray) cells.

The UVR dosages tested in these experiments were: 10 mJ/cm², 25 mJ/cm², 40 mJ/cm², 50 mJ/cm², and 75 mJ/cm² (FIG. 2).

Fibroblast cell viability was evaluated 24 hours after UVR treatment using the trypan blue cell death assay. The data indicated that cell viability was significantly attenuated when the UVR dosage was increased from 50 mJ/cm² to 75 mJ/cm². Based on these data, a dosage of 60 mJ/cm² for the UV radiation was selected for further study using Western blot assay analysis.

Experimental Example 2

Effects of UVA/UVB on the Expression of MMP-1 in Human Fibroblast

Human fibroblast cells (AG04058, Coriell) were grown in MEM completed medium. The fibroblast cells were plated into 4 cm tissue culture dishes the day before the assay. The fibroblast cells were treated with UVA or UVB at a dosage of 60 mJ/cm² using a Stratalinker UV Crosslinker (Stratagene, La Jolla, Calif.). The supernatants from the cultures were collected at 6 hours and 24 hours after UV treatment. Cell viability was evaluated by trypan blue assay and found to be >95% at every indicated UV radiation dosage.

For the western blot, equal amounts of proteins were mixed with 2× sample buffer, boiled for 5 minutes, and chilled on ice. The samples were subjected to 4%-15% SDS-PAGE, and electrophoretically transferred to a nitrocellulose membrane. The membrane was blocked with 5% dry milk in washing buffer.

Figure 3:
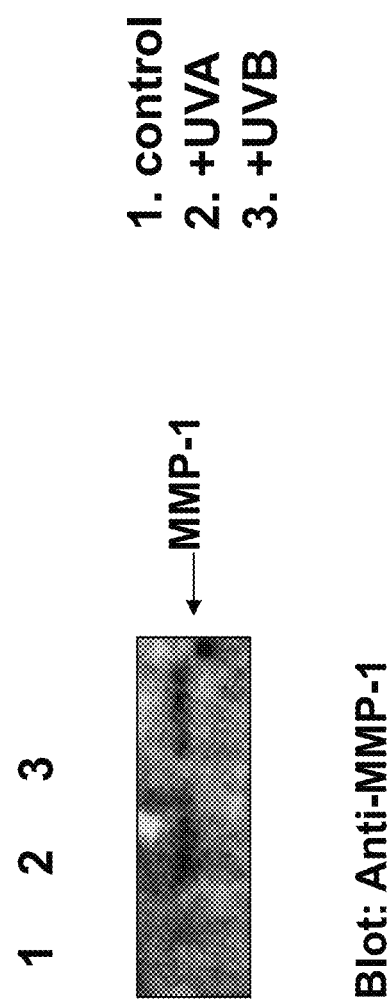
FIG. 3 is an image of a Western blot illustrating the effect of UVA and UVB exposure on MMP-1 expression in human fibroblast cells. Lane 1 is control; lane 2 are cells stimulated with UVA radiation; lane 3 are cells stimulated with UVB radiation.

MMP-1 protein was detected with anti-MMP-1 antibody (Calbiochem). The result was visualized using the ECL detection system. In contrast to the control, a clear band of MMP-1 was evident in the samples treated with either UVB or UVA. This result confirmed that human fibroblast MMP-1 was enhanced in the presence of UVA/UVB (FIG. 3).

Experimental Example 3

Figure 4:
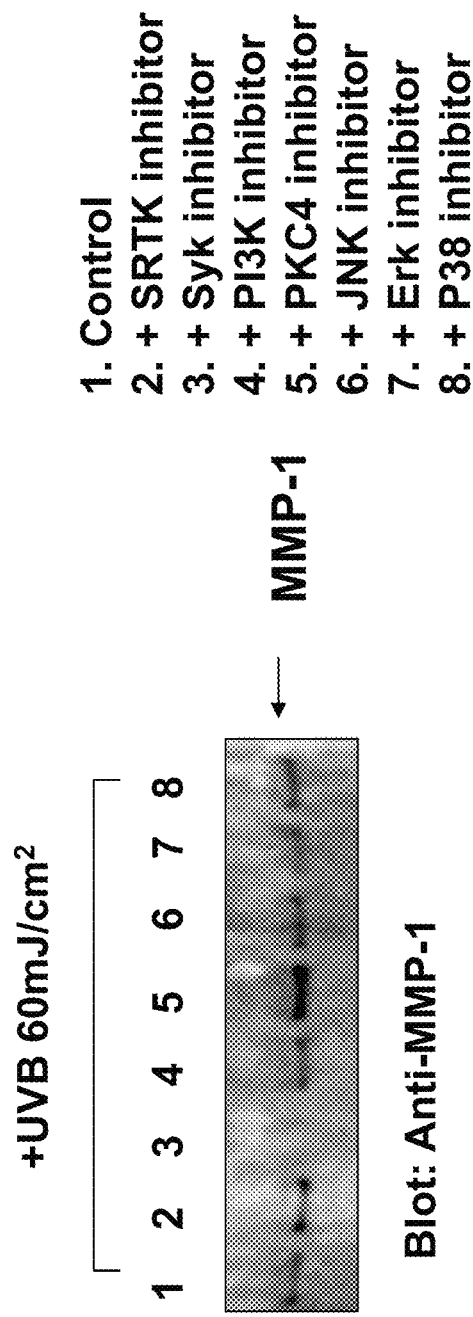
FIG. 4 is an image of a Western blot illustrating the effect of various kinase inhibitors on and UVB-induced MMP-1 expression in human fibroblast cells. Lane 1 is control; lane 2 comprises a SRTK inhibitor; lane 3 comprises a Syk inhibitor; lane 4 comprises a PI3K inhibitor; lane 5 comprises a PKC4 inhibitor; lane 6 comprises a JNK inhibitor; lane 7 comprises an Erk inhibitor; and lane 8 comprises a P38 inhibitor.

Identification of Kinases Which Activity is Important for UV Induced Skin Damage Human fibroblast cells (AG04058) were seeded into 24-well tissue culture dishes with MEM medium one day before the assay. Specific inhibitors for each kinase were added into each different well as indicated (FIG. 4). The supernatants were collected at 24 hours after UV treatment.

Protein samples from the cell supernatants were evaluated by western blot assay. The band of MMP-1 was observed in each treatment condition except in the presence of Syk kinase inhibitor. These data suggested that suppressing Syk with specific inhibitors suppressed MMP-1 expression (FIG. 4).

Experimental Example 4

Increase of MMP-1 Expression by Syk Kinase in Human Fibroblast Cells

Human fibroblast cells were transiently transfected with human Syk kinase cDNA by Fugene 6 transfection reagent. Forty eight hours after transfection, the cells were further exposed to either UVA or UVB at a dosage of 60 mJ/cm². Supernatants from the cell cultures were harvested for western blot assay 24 hours after UV treatment. In the anti-human MMP-1 western blot (FIG. 5), more MMP-1 was found in the Syk transfected cells. The results indicated that Syk kinase enhanced the MMP-1 expression in the human fibroblast cells treated with either UVA or UVB.

Figure 5:
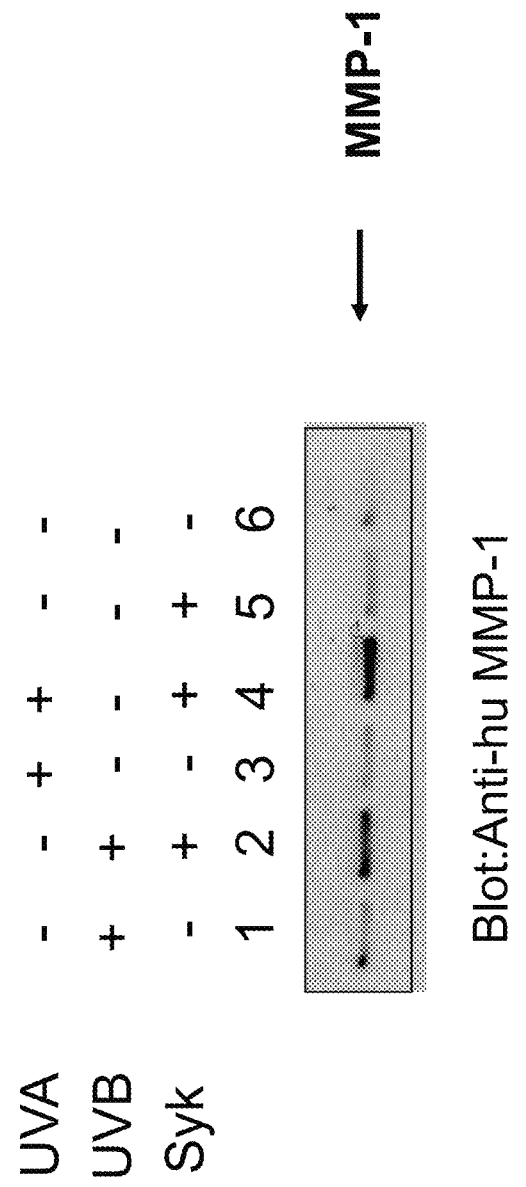
FIG. 5 is an image illustrating the effect of Syk kinase on MMP-1 expression in human fibroblast cells. Lanes 5 and 6 are negative controls.

Thus, transfection of extra Syk enhanced MMP-1 expression (FIG. 5). As demonstrated elsewhere herein, expression of MMP-1 was dramatically inhibited by piceatannol, a specific inhibitor for Syk kinase. Therefore, these data suggest that Syk kinase plays an important role in UV induced photo-damage by modulating MMP-1 expression in human fibroblast cells.

Experimental Example 5

Figure 9A:
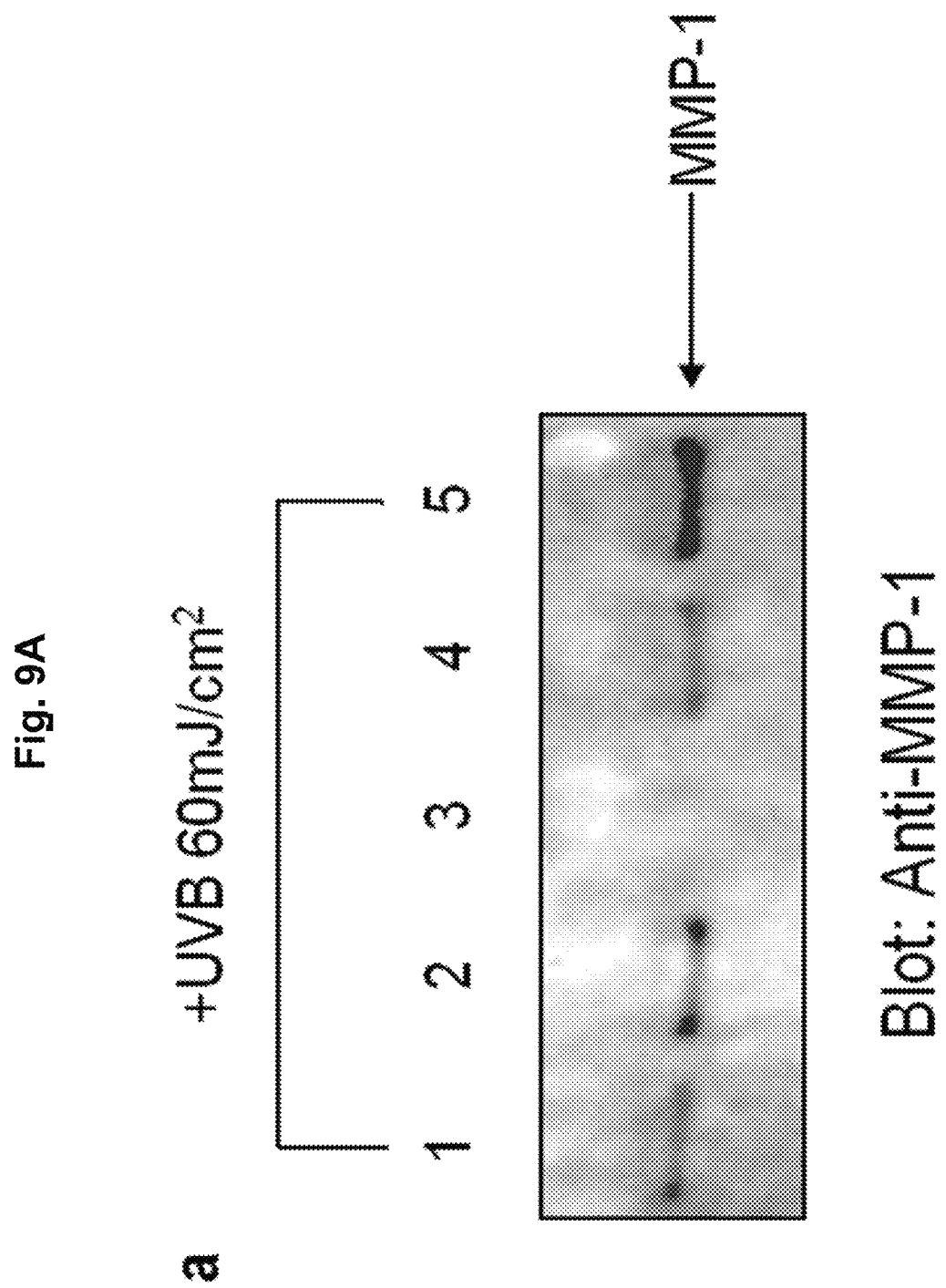
Figure 9B:
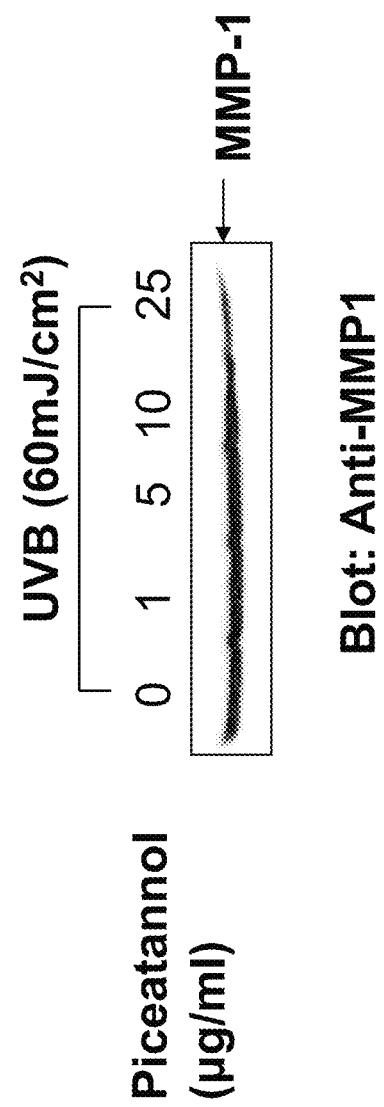

Decrease of MMP-1 Expression by Syk Inhibitor Piceatannol in Human Dermal Fibroblasts HDFs were pre-treated (before UV exposure) with different kinase inhibitors, as indicated in FIG. 8. MMP-1 expression was significantly inhibited by the Syk inhibitor piceatannol (25 µg/ml) (lane 3 in FIG. 9A) (Speich et al., 2008, Am Physiol Cell Physiol 295:C1045-54; Sulimenko et al., 2006, J Immunol 176:7243-53). The dose-response of piceatannol inhibition was assessed in HDFs exposed to UVB (60 mJ/cm²) (FIG. 9B). The western blot data indicated that MMP-1 expression was dramatically (63%) inhibited by piceatannol at a concentration of 25 µg/ml, while only 20% inhibition was found at a 10 µg/ml piceatannol. There was no inhibition of MMP-1 expression by lower concentrations of piceatannol such as 1 µg/ml and 5 µg/ml, as demonstrated by the density analysis in FIG. 9C.

Experimental Example 6

Decrease of MMP-1 Expression by Syk siRNA in Human Dermal Fibroblasts

Figure 10:
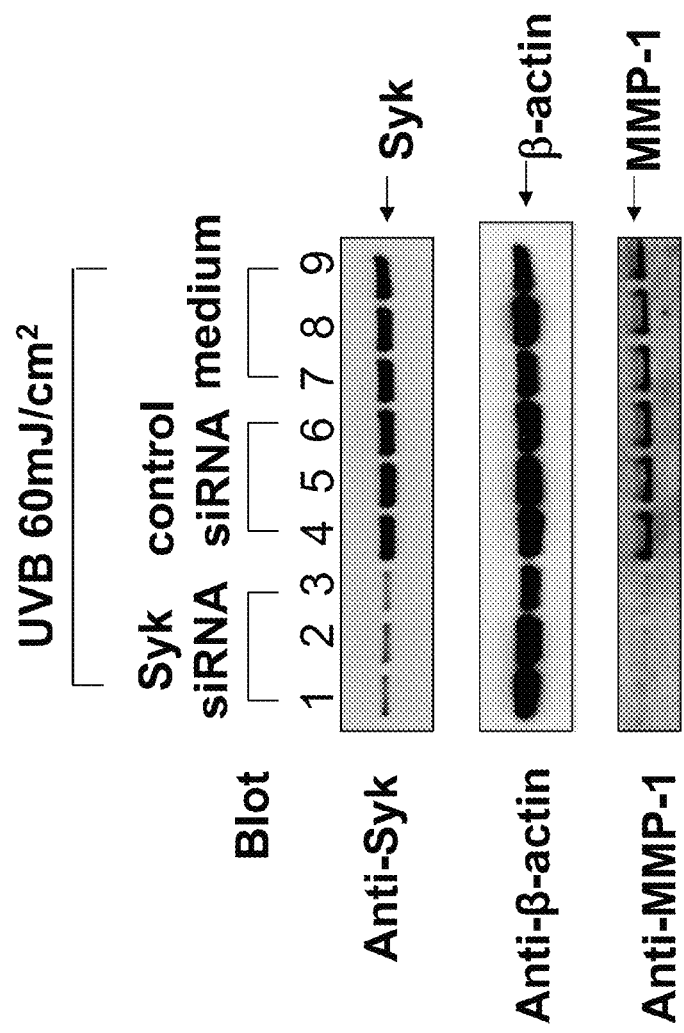
FIG. 10 illustrates the finding that Syk siRNA inhibits MMP-1 expression in human dermal fibroblasts (HDFs). HDFs were transfected with Syk cDNA 24 his before siRNA transfection. Lanes 1-3: HDFs transfected with Syk siRNA, Lanes 4-6: HDFs transfected with control siRNA, Lanes 7-9: HDFs with medium. HDF lysates were immunoblotted with anti-Syk antibody (upper panel). The same membrane was reblotted with anti-β-actin antibody (middle panel). Culture medium from each sample was immunoblotted with anti-MMP-1 antibody (lower panel).

To confirm the results shown in FIG. 9, either control siRNA or Syk siRNA was transfected into HDFs 24 hours after Syk cDNA transfection. 24 hours after transfection of siRNA cells were exposed to UVB (60 mJ/cm²), and after another 24 hours cell cultures were harvested for MMP-1 expression assay while cell lysates were used for Syk expression determination by western blot (FIG. 10). The results indicated that in contrast to control siRNA (lanes 4-6) and control medium (lanes 7-9), Syk siRNA (lanes 1-3) significantly inhibited MMP-1 expression (lower panel) by modulating Syk expression (upper panel). The middle panel shows results of the loading control by reblotting with anti-β-actin antibody.

Experimental Example 7

Effect of UVR on Syk Expression in Human Skin Fibroblasts

Figure 6:
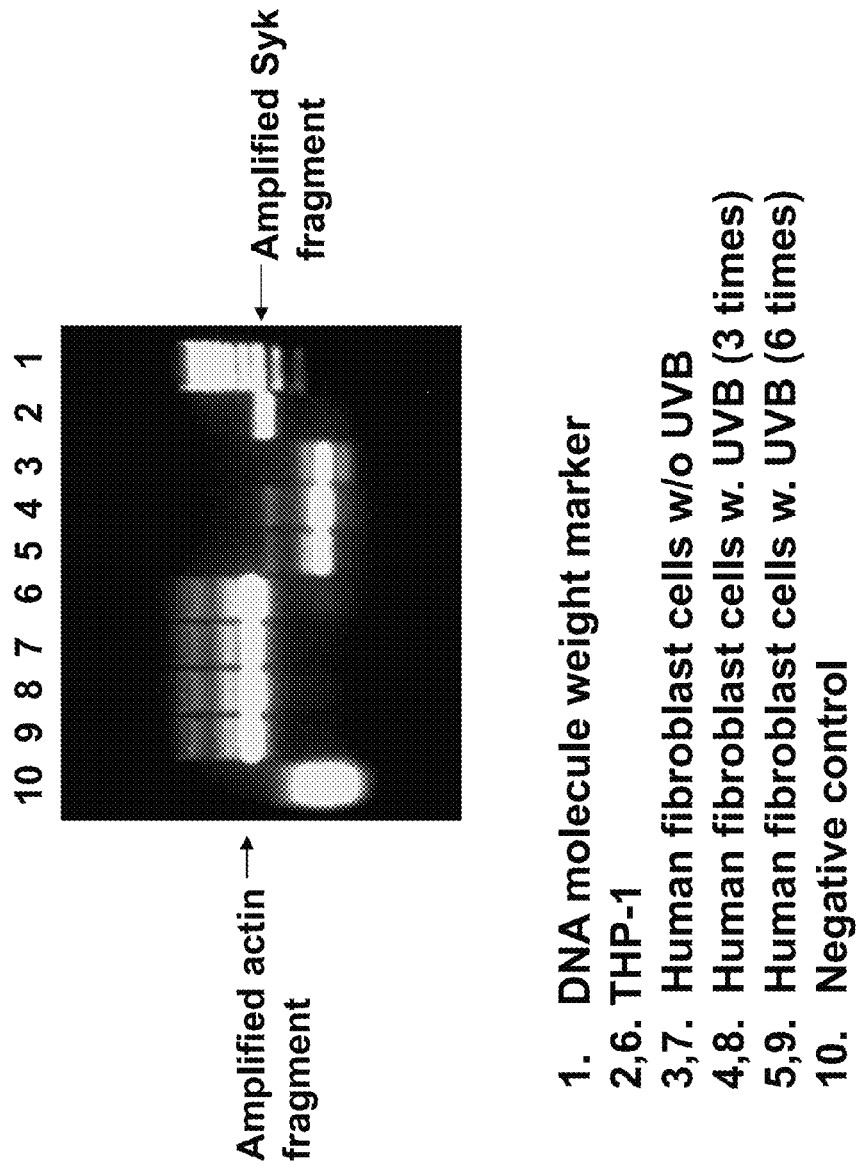
FIG. 6 is an image of a Western blot illustrating the analysis for Syk expression in human fibroblast cells exposed to UVB radiation. Lane 1 (far right) depicts a DNA molecular weight marker; lanes 2 and 6 depict human monocytic cells that express high levels of Syk kinase (THP-1 cells); lanes 3 and 7 depict human fibroblast (HB) cells that were not exposed to UVB radiation; lanes 4 and 8 depicts human fibroblast (HB) cells that were exposed to UVB radiation (60 mJ/cm$^2$) for three treatments; lanes 5 and 9 depicts human fibroblast cells that were exposed to UVB radiation (60 mJ/cm$^2$) for six treatments; lane 10 is a negative control. Protein loading control is demonstrated by an amplified actin fragment in lanes 6-9.

The effect of UV radiation (UVR) on Syk expression was studied in human skin fibroblasts. Since Syk kinase expression in normal human fibroblast cells is low, the reverse transcription polymerase chain reaction (RT-PCR) was used to detect Syk expression in those cells. Human fibroblast cells were exposed to UVB at 60 mJ/cm² once a day for either three or six days of treatment. The RT-PCR results showed that UVR enhanced the Syk expression in human fibroblast cells (FIG. 6).

In order to confirm this finding in vivo, the effect of UV on Syk expression in the hairless mouse was investigated in vivo. The skin of hairless mice was exposed to UVB 3 times a week for a duration of 10 weeks, as shown in Table 1. Following UVB exposure, expression of Syk kinase and MMP-13 protein in the skin of those mice were detected by Western Blot. It has been reported that mouse MMP-13 plays the similar role as MMP-1 in human fibroblasts. These data showed that both Syk kinase and MMP-13 expressions were enhanced by UV exposure (FIG. 3, FIG. 6, and FIG. 7). The data both in vitro (human fibroblast cells) and in vivo (skin of hairless mice) demonstrated that UVR enhanced both Syk and MMP-1 expressions in human and MMP-13 in mouse. As demonstrate elsewhere herein, a Syk specific inhibitor decreased MMP-1 expression in the human fibroblast cells with UV exposure (FIG. 4).

TABLE 1

Procedure and dosage of UV exposure in hairless mice

| Week | Weekly dose of UVB | Cumulative dose at the end of the experimental period | Weekly dose of UVB ($mJ/cm^2$) | Daily dose of UVB (three times per week) | Daily dose of UVB ($mJ/cm^2$) |
|---|---|---|---|---|---|
| 1 | 1 MED | 1 MED | 5 | 0.33 MED | 1.67 |
| 2 | 2 MED | 3 MED | 10 | 0.67 MED | 3.33 |
| 3-10 | 3 MED | 27 MED | 15 | 1 MED | 5 |

Experimental Example 8

Effect of UVR on Syk Activation in Human Dermal Fibroblasts

Figure 11A:
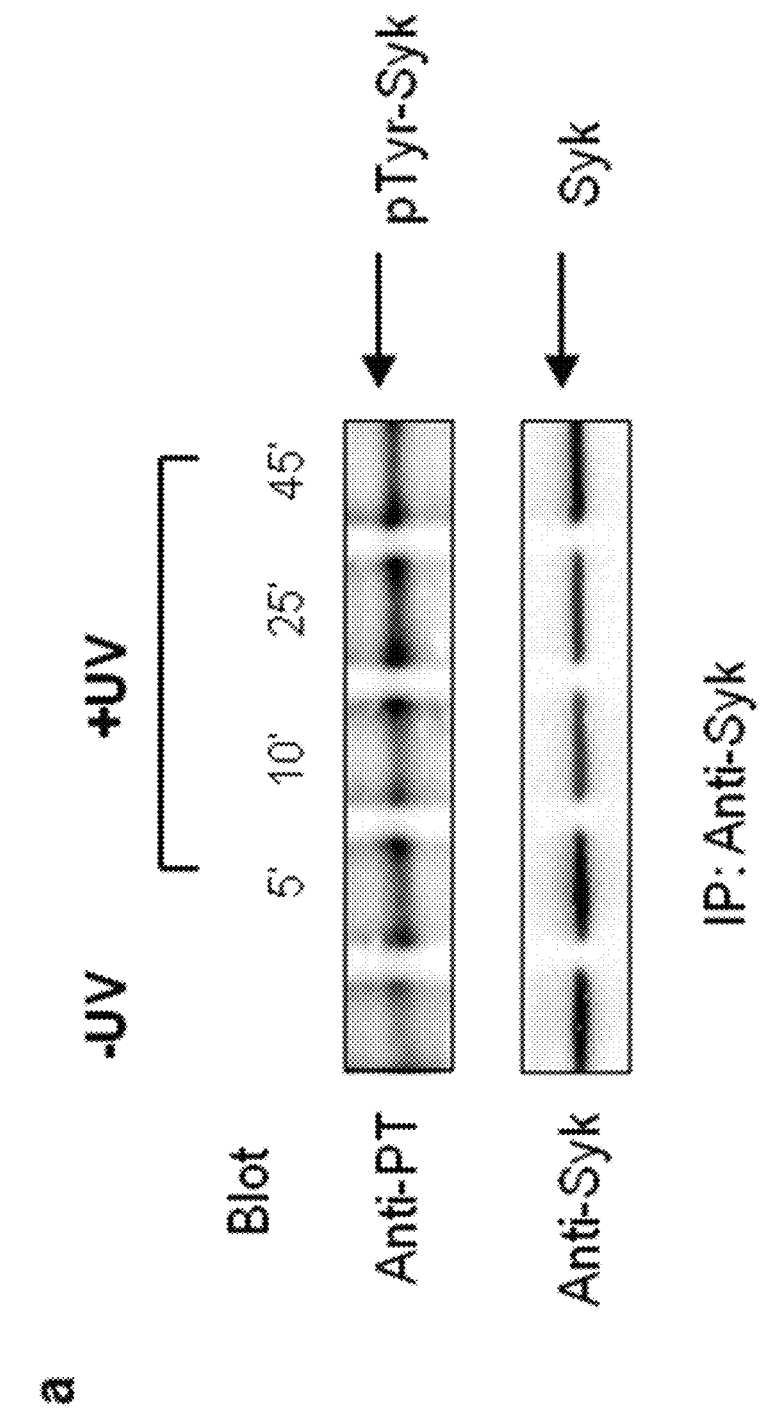
FIGS. 11A-11B, illustrates the finding that UV exposure enhances Syk tyrosine phosphorylation.
Figure 11B:
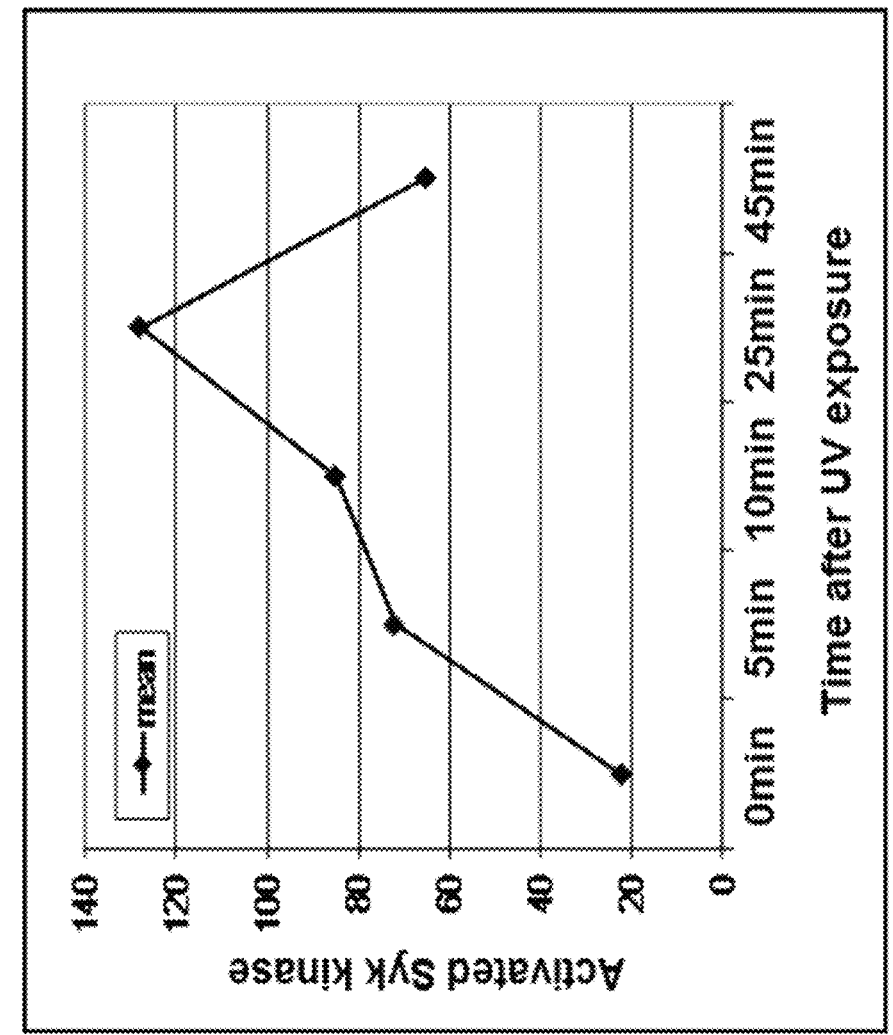

The effect of UVR on the dynamics of Syk activation was evaluated by transiently transfecting Syk cDNA into HDFs, due to the low inherent expression of Syk in normal HDFs. After UV exposure, cells were harvested at the indicated time points (FIG. 11). Cell lysates were immunoprecipitated with anti-Syk antibody and blotted with anti-phosphotyrosine antibody. The results indicated higher Syk tyrosine phosphorylation in cells exposed to UV vs, unexposed cells, suggesting enhanced Syk activation upon UV exposure (FIG. 11A). Syk tyrosine phosphorylation exhibited a maximum 25 min after UV exposure and its activation lasted for at least 45 min (FIGS. 11A and 11B).

Experimental Example 9

Effect of Syk on Activation of MAPKs in Human Dermal Fibroblasts Exposed to UVB

Figure 12C:
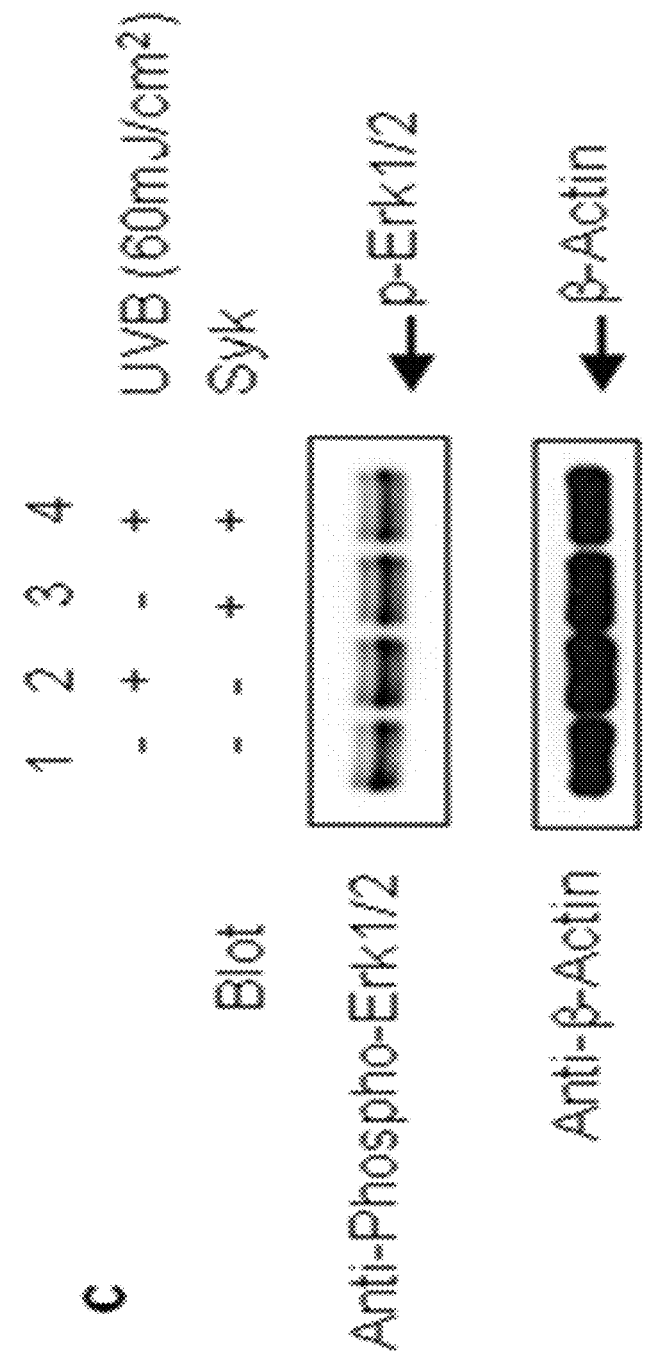

MAPKs are known to play an important role in UV induced signaling. One possible hypothesis is that Syk affects MMP-1 expression by modulating the activation of MAPKs. In order to test this hypothesis, HDFs were transiently transfected with Syk cDNA, and after UV exposure, cell lysates were blotted with anti-phospho-JNK, anti-phospho-p38, and anti-phospho-Erk1/2 antibodies, respectively. The results demonstrated that only JNK phosphorylation was dramatically enhanced in cells transfected with Syk vs. controls (lane 3 vs, lane 1 and lane 4 vs, lane 2 in FIG. 12A), Moreover, based on the result of reblotting with anti-JNK, the enhanced phospho-JNK was phospho-JNK1. The data also confirmed that UV exposure enhanced JNK activation (lane 2 vs. lane 1 and lane 4 vs. lane 3 in upper panel of FIG. 12A). However, in the anti-phospho-p38 blot, no signal change was observed in cells transfected with Syk vs. controls while, as anticipated, UV exposure increased p38 phosphorylation (lane 2 vs. lane 1 and lane 4 vs. lane 3 in FIG. 12B). In contrast to the anti-phospho-JNK and anti-phospho-p38 blots, no changes of Erk1/2 signal in the presence or absence of UV exposure or in the presence of elevated Syk levels were found (FIG. 12C). The combined results from FIGS. 12A-12C confirmed that both INK and p38 MAPKs, but not Erk1/2, play a role in UV induced signaling in HDFs, and demonstrate that only JNK1 is related with Syk activation. These data suggest that Syk might affect MMP-1 expression by modulating JNK1 activity, and thus play an important role in UV induced skin photo-damage.

Experimental Example 10

Effect of UV Exposure on Syk and MMP-13 Expression in the Skin of Hairless Mice

Figure 13A:
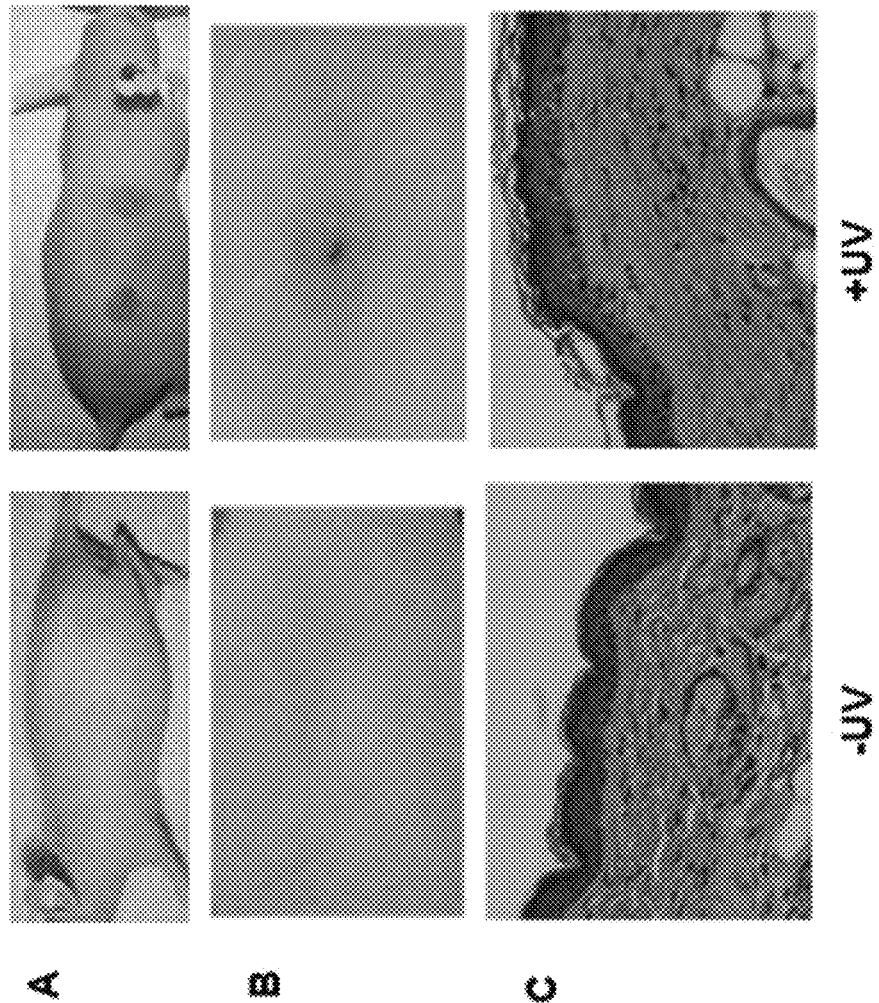
FIGS. 13A-13E, illustrates the altered expression of Syk and MMP-13 in hairless mice with UV exposure.

In order to confirm the findings in vivo, hairless mice were exposed to UVR for either 5 or 10 weeks as indicated in Table 1, Erythema was noted on the skin of hairless mice after UV exposure (Panel A and B of FIG. 13A). Hematoxylin and Eosin (H&E) stained images of skin sections revealed significant orthokeratosis of the stratum corneum in the skin of mice exposed to UV compared to control unexposed animals. The average thickness of the epidermis of the exposed mice was higher than that of the controls (Panel C of FIG. 13A). The epidermal thickness increased from 8.8 μm to 18.3 μm at the end of week 10. Syk and MMP-13 expression were measured in skin harvested from the mice after UV exposure.

Figure 13B:
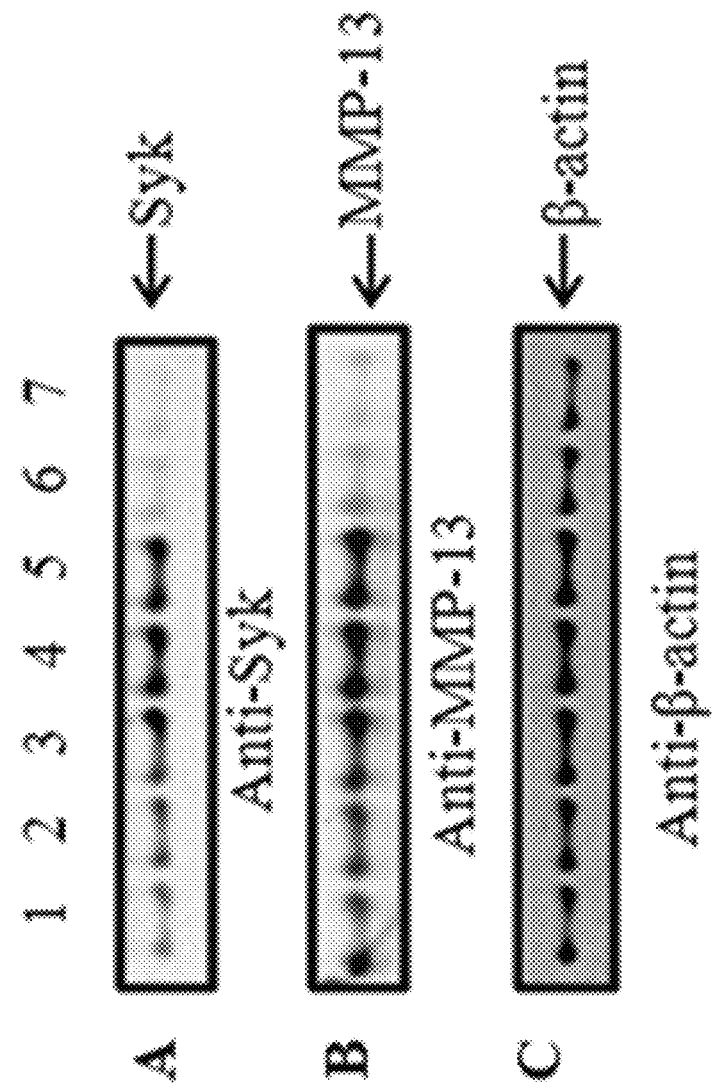
Figure 13C:
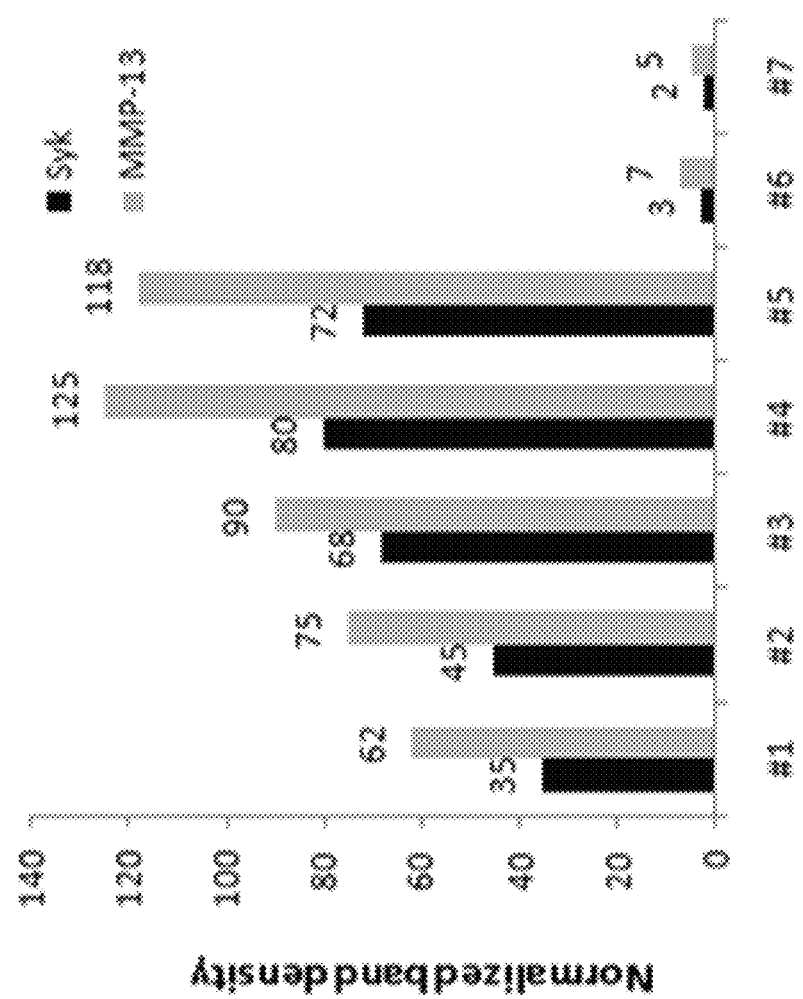
Figure 13D:
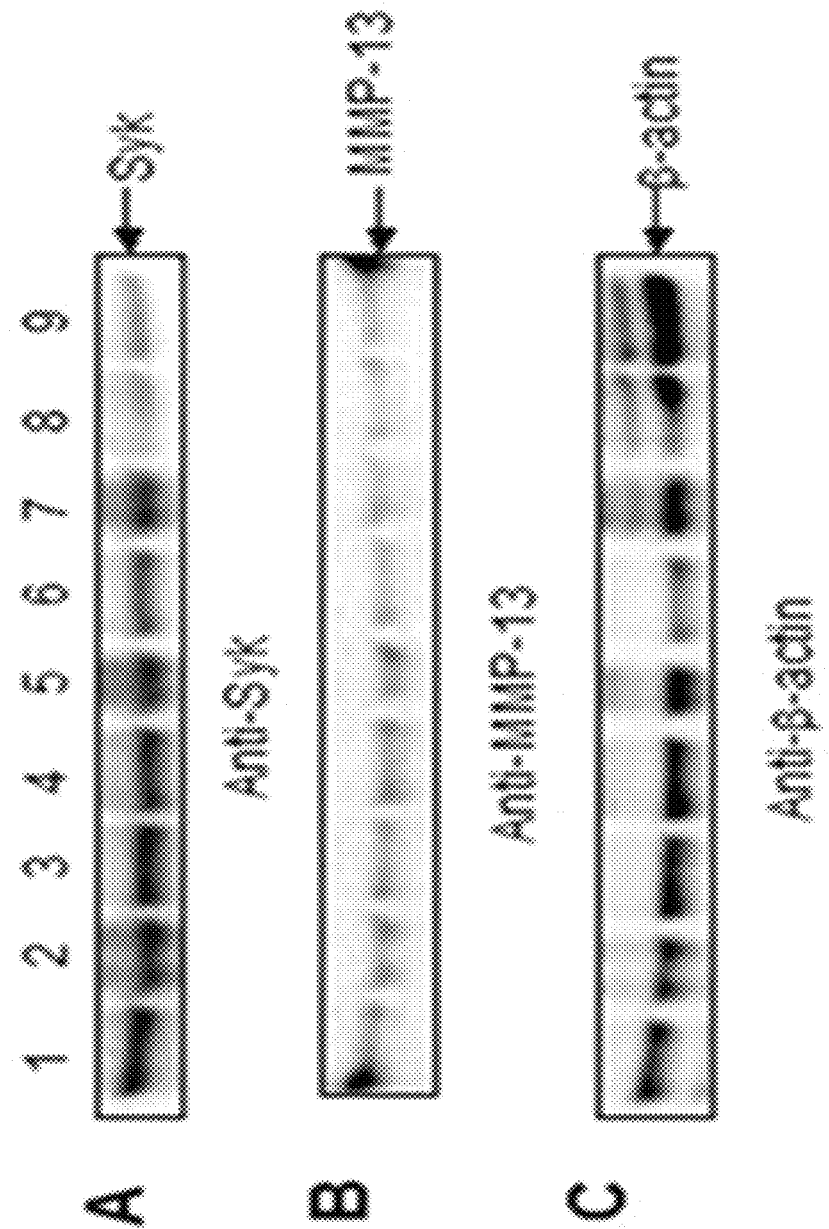
Figure 14:
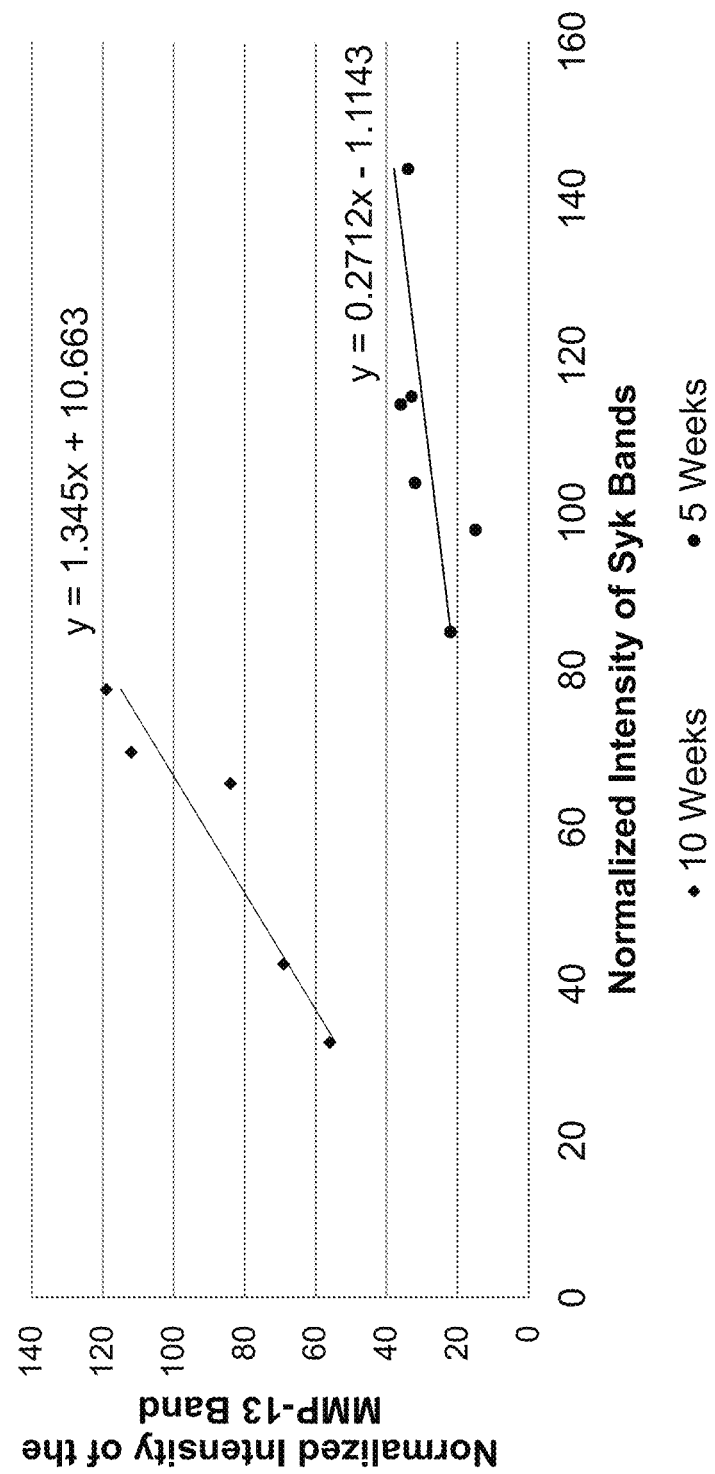
FIG. 14 is a graph illustrating the relationship between Syk expression and MMP-13 expression in the skin of hairless mice. Western blot results were quantified by image-density analysis. Expression levels of Syk and MMP-13 were normalized by the actin expression level for each sample, and are presented in a scatter plot. The smaller slope for the samples exposed to UV for 5 weeks compared to the samples exposed to UV for 10 weeks suggests that Syk expression is preceding MMP-13.
Figure 15:
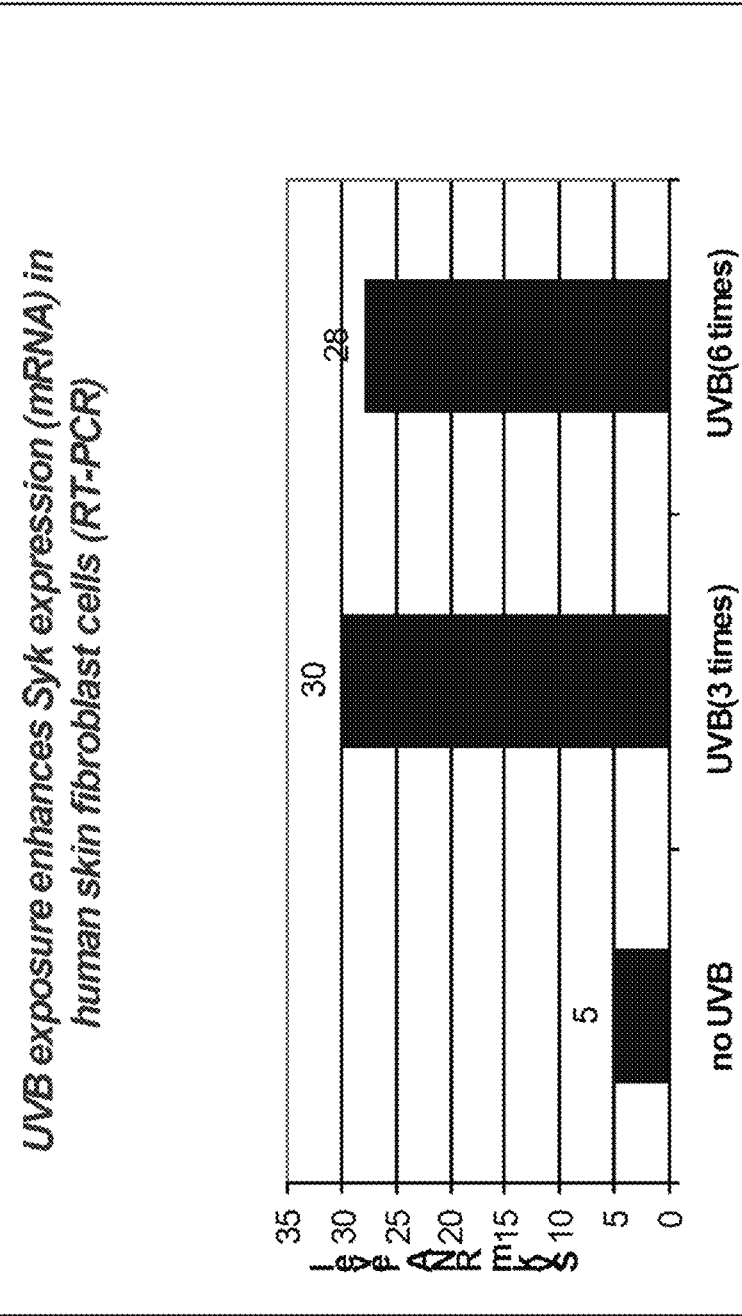
FIG. 15 is a bar graph illustrating the finding that UVB exposure enhances Syk expression (mRNA) in human skin fibroblast cells (RT-PCR).
Figure 17:
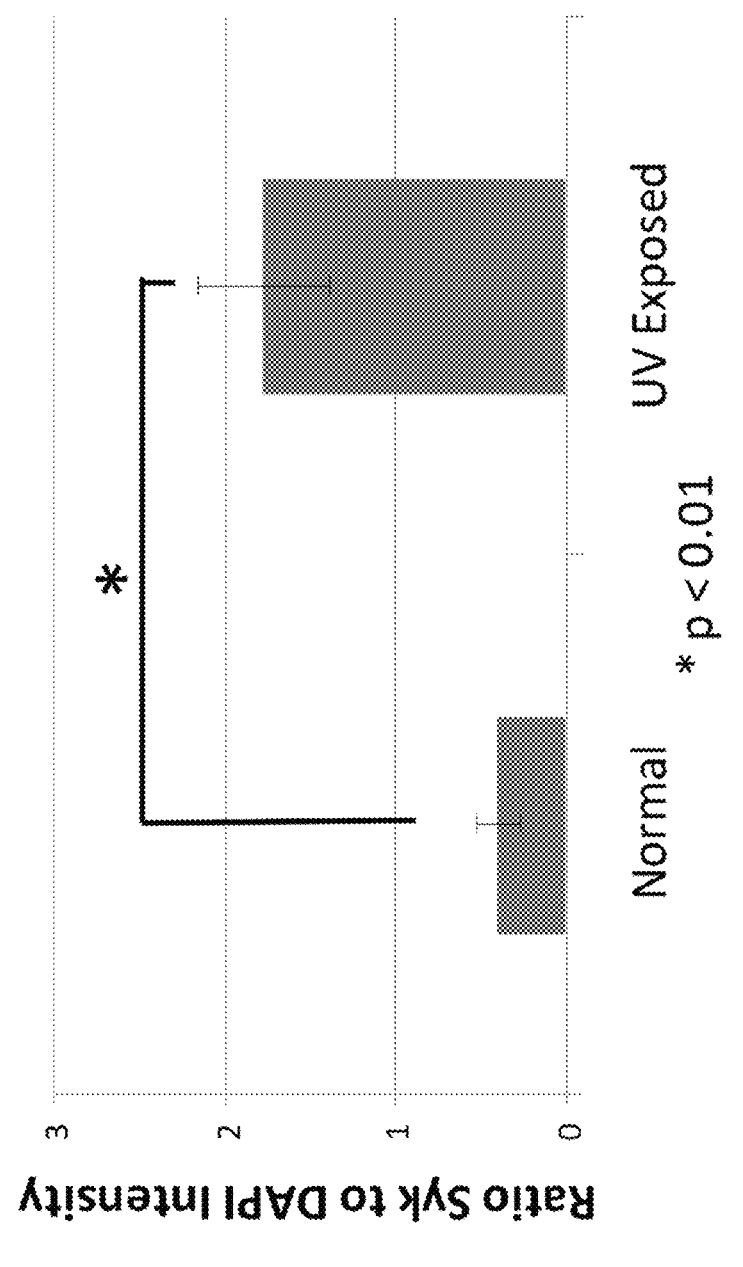
FIG. 17 is a bar graph comparing Syk expression in human skin with and without UV exposure.
Figure 18:
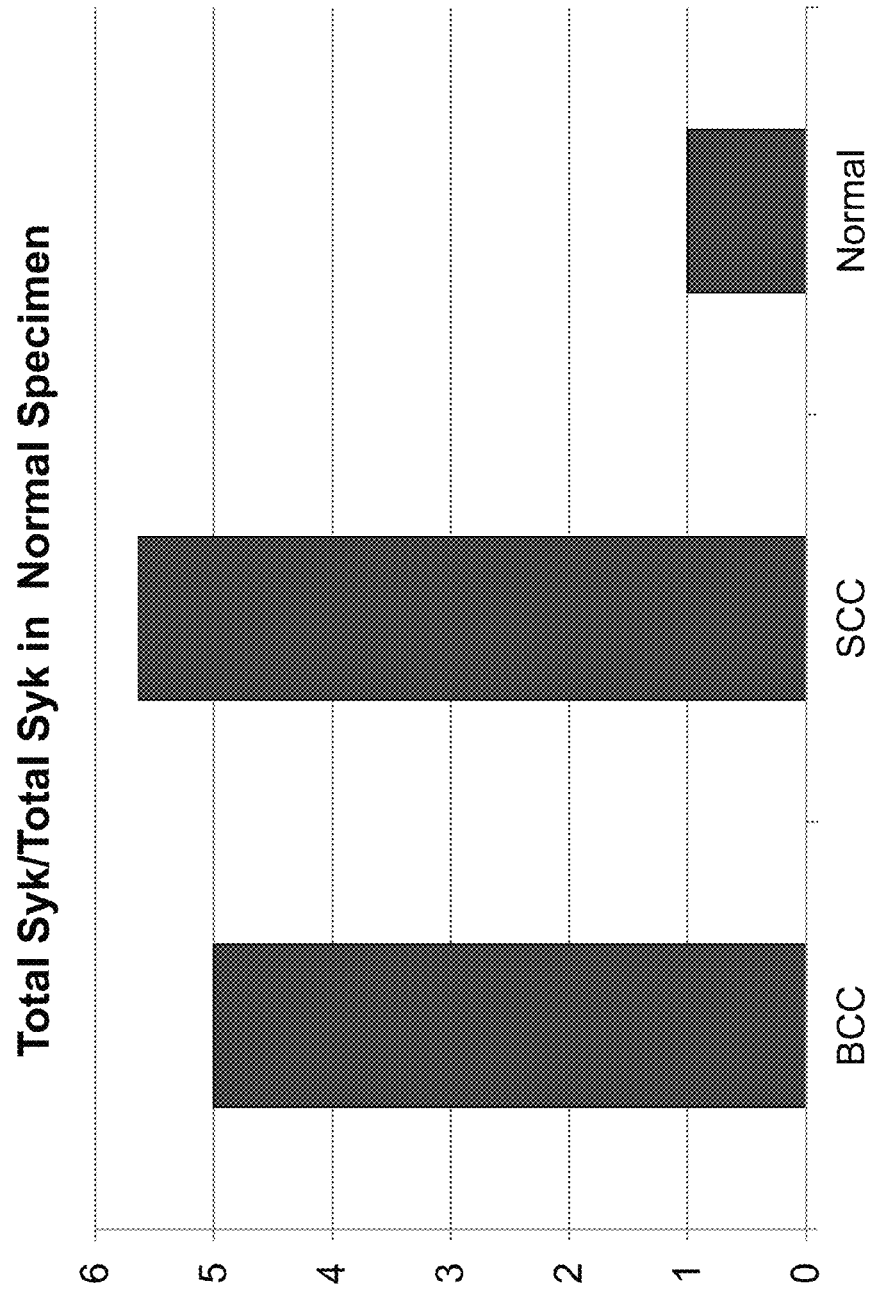
FIG. 18 is a bar graph comparing Syk expression in human biopsies.
Figure 19:
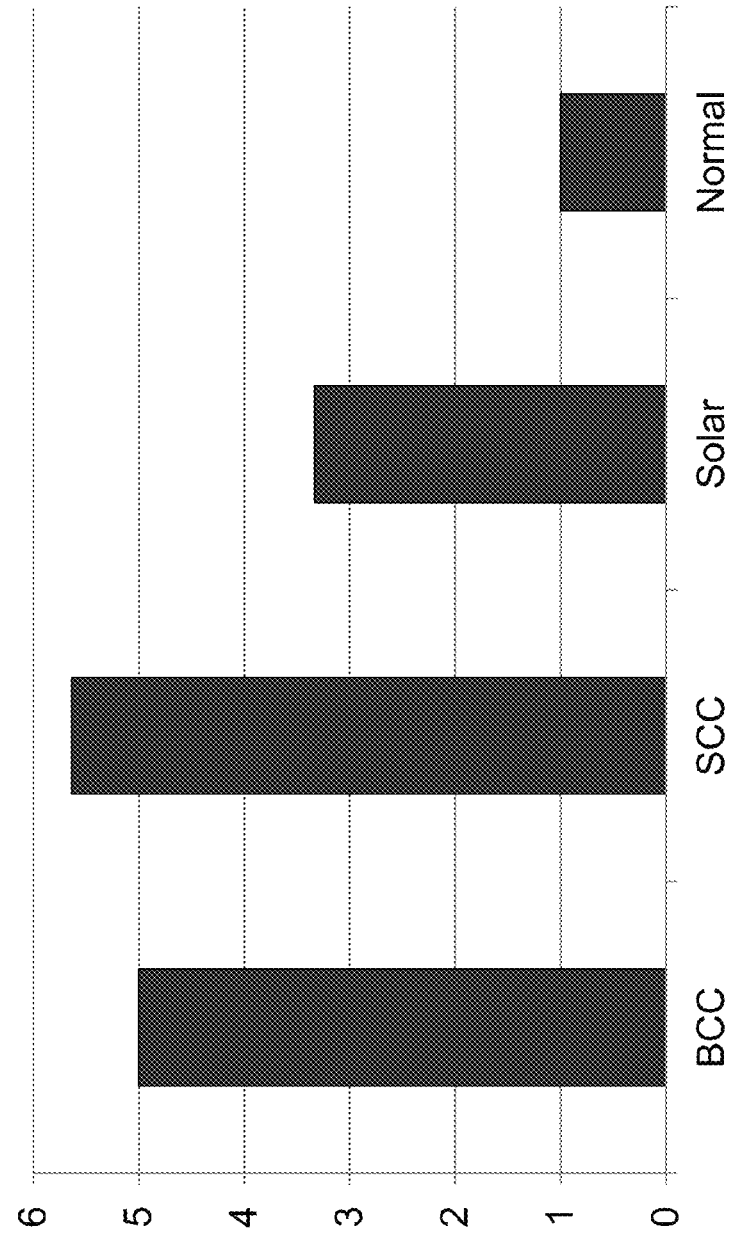
FIG. 19 is a bar graph comparing Syk expression in human biopsies.
Figure 20:
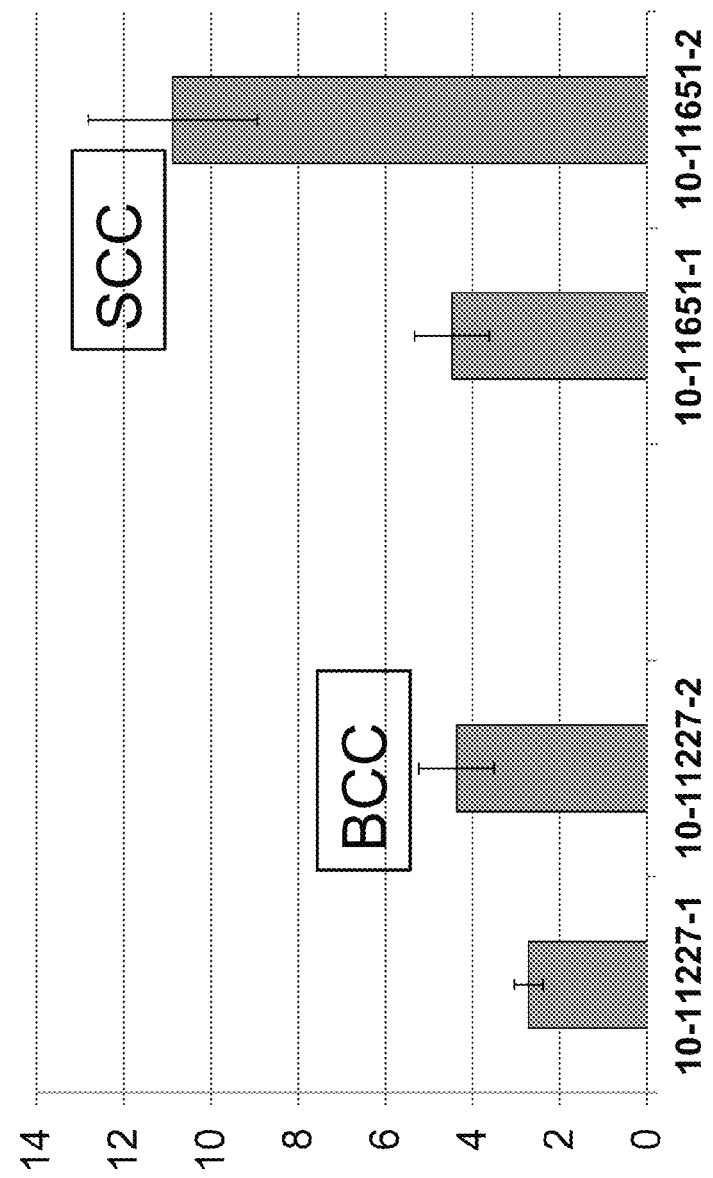
FIG. 20 is a bar graph comparing Syk expression in cancerous and normal samples of the same patient.

The results showed that Syk expression was dramatically enhanced in skin samples after either 5 or 10 weeks of UV exposure (Panel A of FIGS. 13B and 13D). However, MMP-13 expression was found to clearly increase only in the samples exposed to UV for 10 weeks (in panel B of FIG. 13B), and showed no significant increase in skin samples exposed to UV for 5 weeks. (Panel B of FIG. 13D). In panel C of FIGS. 13B and 13D, the same membranes were reblotted with anti-β-actin to determine the Loading of protein. These results demonstrate that Syk is altered earlier than MMP-13 in the skin of hairless mice after UV exposure, and suggest that Syk might be an earlier biomarker for UV induced photo-damage. FIG. 14 showed positive correlation between Syk and MMP-13 expression and demonstrated dose dependence of Syk and MMP-13; higher Syk levels result in higher MMP-13 expression in the skin of hairless mice exposed to UV. Therefore, Syk enhances expression of collagenase: MMP-1 in HDFs in vitro and MMP-13 in the skin of hairless mice in vivo.

Figure 13E:
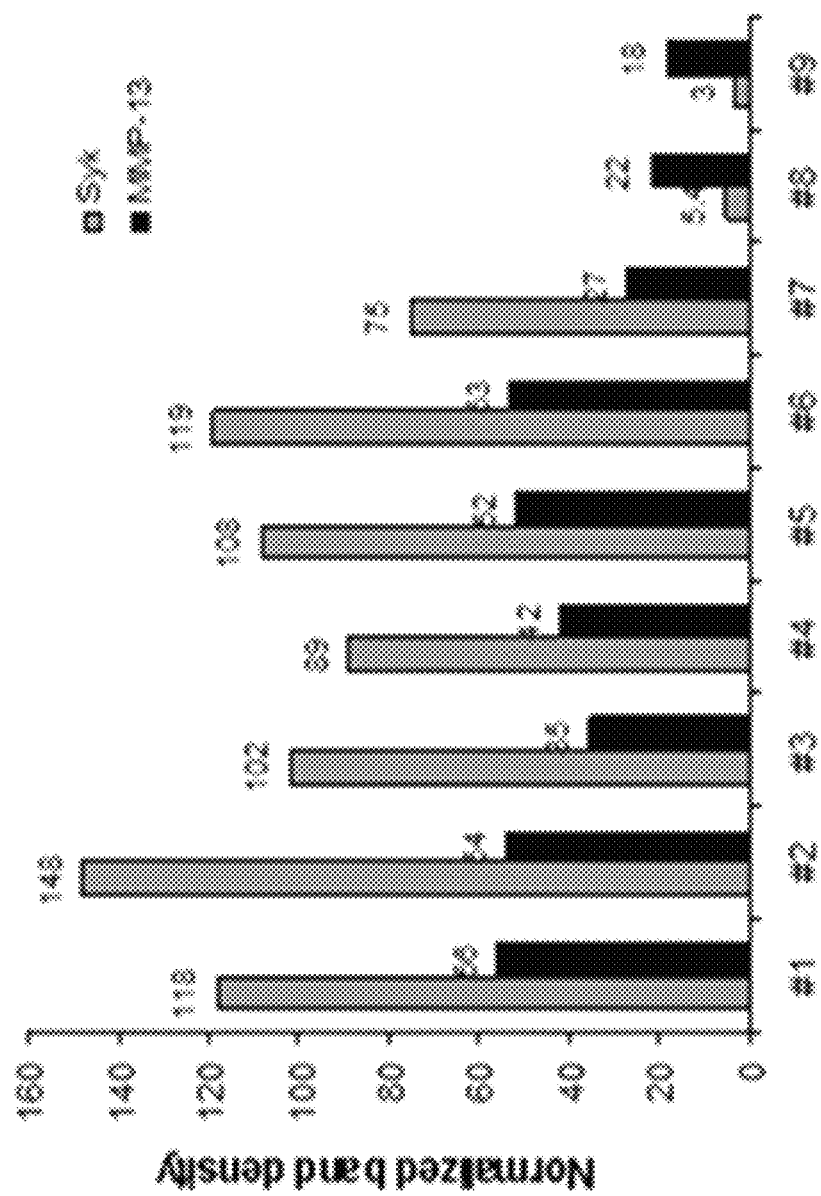

The in vivo results indicated that UV exposure enhances both Syk and MMP-13 expression in the skin of hairless mice exposed to UV for 10 weeks (FIGS. 13B and 13C). The data also demonstrated that Syk has a positive correlation with MMP-13 expression in the skin of hairless mice upon UV exposure (FIG. 14). This confirms the in vitro findings that Syk enhances MMP-1 expression in HDFs (FIG. 8). In skin samples of mice exposed to UV for 5 weeks, no significant alternation of MMP-13 expression was observed, while changes in Syk expression could still be clearly detected (FIGS. 13D and 13E). This suggested that Syk may be an earlier marker to MMP-1 for UV induced skin photo-damage, and could play an important role in the protection and remediation of UV induced skin photo-damage because collagen repair is a slow and lengthy process after collagen has been degraded by the activated MMPs.

The studies described herein shed light on the effect of Syk on MAPKs activation in human dermal fibroblasts exposed to UV. The data indicated that Syk only enhanced JNK phosphorylation (FIG. 12A), but not p38 (FIG. 12B) or Erk1/2 phosphorylation (FIG. 12C), although p38 was activated under the same conditions of UV exposure (FIG. 12B). This suggested that Syk may enhance MMP-1 expression by modulating JNK activation. In contrast to the clear effect of UV on the activation of stress-activated protein kinases (JNK and p38), Erk1/2 MAPK activation depended on the level and type of UV exposure. The response of Syk to lower levels of UVB exposure is important as it may relate to chronic UV damage by exposure at levels at or below minimal erythema dosages.

In conclusion, the studies described herein showed that UV exposure enhanced expression and activation of Syk kinase in human dermal fibroblasts and in the skin of hairless mice. Syk increased MMP-1 expression, and the results indicated that Syk may affect MMP-1 expression by modulating JNK activity in human dermal fibroblasts with UV exposure. The results suggested that Syk could be a useful therapeutic target and an earlier biomarker to MMP-1 for UV induced skin photo-damage.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of detecting and treating or protecting against ultraviolet radiation (UVR)-induced skin damage in a mammal, said method comprising the steps of:
   measuring a level of Syk kinase in a skin sample obtained from said mammal by performing an immunoassay for assessing the level of said Syk kinase in said sample, said immunoassay selected from the group consisting of: a western blot, ELISA, immunoprecipitation, immunohistochemistry, immunofluorescence, radioimmunoassay, dot blotting, and fluorescence-activated cell sorting (FACS) or a nucleic acid assay for assessing the level of a nucleic acid encoding said Syk kinase in said sample, said nucleic acid assay selected from the group consisting of: a northern blot, a Southern blot, in situ hybridization, PCR assay, RT-PCR assay, a probe-array-based assay, a gene-chip-based assay, and a microarray-based assay,
   comparing the level of said Syk kinase in said sample to a control level of Syk kinase in a control sample, wherein when the level of said Syk kinase in said sample is elevated compared to the level of Syk kinase in the control sample, Syk kinase is activated and said mammal is afflicted with UVR-induced skin damage, and
   administering to said mammal a therapeutically effective amount of a pharmaceutical composition comprising piceatannol or a salt thereof when the level of said Syk kinase in said sample is elevated compared to the level of Syk kinase in a control sample, thereby treating or protecting said mammal afflicted with UVR-induced skin damage.

2. The method of claim 1, wherein said mammal is selected from the group consisting of a mouse, rat, non-human primate, and human.

3. The method of claim 2, wherein said mammal is a human.

4. The method of claim 1, wherein said skin sample comprises skin tissue.

5. A method of identifying and treating a mammal at risk of developing UVR-induced skin damage, photoaging, or photocarcinogenesis, said method comprising the steps of:
   measuring a level of Syk kinase in a skin sample obtained from said mammal by performing an immunoassay for assessing the level of said Syk kinase in said sample, said immunoassay selected from the group consisting of: a western blot, ELISA, immunoprecipitation, immunohistochemistry, immunofluorescence, radioimmunoassay, dot blotting, and fluorescence-activated cell sorting (FACS) or a nucleic acid assay for assessing the level of a nucleic acid encoding said Syk kinase in said sample, said nucleic acid assay selected from the group consisting of: a northern blot, a Southern blot, in situ hybridization, PCR assay, RT-PCR assay, a probe-array-based assay, a gene-chip-based assay, and a microarray-based assay,
   comparing the level of said Syk kinase in said sample to a control level of Syk kinase in a control sample, wherein when the level of said Syk kinase in said sample is elevated compared to the level of Syk kinase in the control sample, Syk kinase is activated and said mammal is afflicted with UVR-induced skin damage, photoaging, or photocarcinogenesis, and
   administering to said mammal a therapeutically effective amount of a pharmaceutical composition comprising piceatannol or a salt thereof when the level of said Syk kinase in said sample is elevated compared to the level of Syk kinase in a control sample, thereby identifying and treating said mammal at risk of developing UVR-induced skin damage, photoaging, or photocarcinogenesis.

6. The method of claim 5, wherein said mammal is selected from the group consisting of a mouse, rat, non-human primate and human.

7. The method of claim 6, wherein said mammal is a human.

8. The method of claim 1, wherein said piceatannol or salt thereof is incorporated within a dermally-acting composition that further comprises a delivery vehicle.

9. The method of claim 8, wherein said delivery vehicle comprises a lipid component.

10. The method of claim 9, wherein said delivery vehicle comprises a liposome.

11. The method of claim 5, wherein said piceatannol or salt thereof is incorporated within a dermally-acting composition that further comprises a delivery vehicle.

12. The method of claim 11, wherein said delivery vehicle comprises a lipid component.

13. The method of claim 12, wherein said delivery vehicle comprises a liposome.

\* \* \* \* \*